US007060844B2

(12) United States Patent
Andrews et al.

(10) Patent No.: US 7,060,844 B2
(45) **Date of Patent: *Jun. 13, 2006**

(54) (3Z)-3-(2,3-DIHYDRO-1H-INDEN-1-YLIDENE)-1,3-DIHYDRO-2H-INDOL-2-ONES AS KINASE INHIBITORS

(75) Inventors: Steven W. Andrews, Longmont, CO (US); Xialing Guo, Irvine, CA (US); Zhen Zhu, Tustin, CA (US); Clarence E. Hull, III, Trabaco Canyon, CA (US); Julie A. Wurster, Irvine, CA (US); Shimiao Wang, Irvine, CA (US); Edward H. Wang, Dove Canyon, CA (US); Thomas Malone, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 375 days.

This patent is subject to a terminal disclaimer.

(21) Appl. No.: 10/405,577

(22) Filed: Apr. 1, 2003

(65) Prior Publication Data

US 2004/0019098 A1 Jan. 29, 2004

Related U.S. Application Data

(63) Continuation of application No. 10/116,309, filed on Apr. 3, 2002, now Pat. No. 6,541,504.

(51) Int. Cl.
*C07D 405/04* (2006.01)

(52) U.S. Cl. .................................................... 548/464

(58) Field of Classification Search ................. 548/464
See application file for complete search history.

(56) References Cited

U.S. PATENT DOCUMENTS

| | | | | |
|---|---|---|---|---|
| 4,966,849 | A | 10/1990 | Vallee et al. | |
| 5,217,999 | A | 6/1993 | Levitzki et al. | |
| 5,302,606 | A | 4/1994 | Spada et al. | |
| 5,330,992 | A | 7/1994 | Eissenstat et al. | |
| 5,792,783 | A | 8/1998 | Tang et al. | |
| 5,834,504 | A | 11/1998 | Tang et al. | |
| 5,883,113 | A | 3/1999 | Tang et al. | |
| 5,883,116 | A | 3/1999 | Tang et al. | |
| 5,886,020 | A | 3/1999 | Tang et al. | |
| 6,541,504 | B1 | 4/2003 | Andrews et al. | |
| 6,699,863 | B1 * | 3/2004 | Andrews et al. | 514/235.2 |
| 6,747,025 | B1 * | 6/2004 | Andrews et al. | 514/235.2 |
| 2004/0198802 | A1 * | 10/2004 | Andrews et al. | 514/414 |

FOREIGN PATENT DOCUMENTS

| | | |
|---|---|---|
| WO | WO 91/15495 | 10/1991 |
| WO | WO 92/20642 | 11/1992 |
| WO | WO 92/21660 | 12/1992 |
| WO | WO 94/03427 | 2/1994 |
| WO | WO 94/10202 | 5/1994 |
| WO | WO 94/14808 | 7/1994 |
| WO | WO99/10325 | 3/1999 |

OTHER PUBLICATIONS

Plowman et al, "Receptor Tyrosine Kinases as Targets for Drug Intervention", 1994, DN&P 7(6): 334-339.
Bolen, "Nonrecptor tyrosine protein kinases", 1993, Oncogen 8: 2025-2031.
Kendall et al, "Inhibition of vascular endothelial cell growth factor activity by an endogenously encoded soluble receptor", 1994, Proc. Natl'l Acad. Sci 90: 10705-10709.
Takano et al, "Inhibition of Angiogenesis by a Novel Diaminoanthraquinone that Inhibits Protein Kinase C.", 1993, Mol. Bio. Cell 4: 2072, p. 358A.
Kinsella et al, "Protein Kinase C Regulates Endothelial Cell Tube Formation on Basement Membrane Matrix, Matrigel", 1992, Experimental Cell Research, 199: 56-62.
Wright et al, "Inhibition of Angiogenesis In Vitro and In Ovo With an Inhibitor of Cellular Protein Kinases, MDL 27032", 1992, Journal of Cellular Phys. 152: 448-457.
Mariani et al, "Inhibition of angiogenesis by FCE 26806, a potent tyrosine kinase inhibitor",1994, Proc. Am. Assoc. Cancer Res. 35:2268; p. 381.
Kim et al, "Inhibition of vascular endothelial growth factor-induced angiogenesis suppresses tumor growth in vivo", Nature 362, 841-844, Apr. 29, 1993.
Jellinek et al, "Inhibition of Receptor Binding by High-Affinity RNA Ligands to Vascular Endothelial Growth Factor", Biochemistry 33: 10450-10456, 1994.

* cited by examiner

*Primary Examiner*—Kamal A. Saeed
*Assistant Examiner*—Rebecca Anderson
(74) *Attorney, Agent, or Firm*—Robert J. Baran; Brent A. Johnson; Martin A. Voet

(57) ABSTRACT

The present invention relates to organic molecules capable of modulating tyrosine kinase signal transduction in order to regulate, modulate and/or inhibit abnormal cell proliferation.

3 Claims, 1 Drawing Sheet

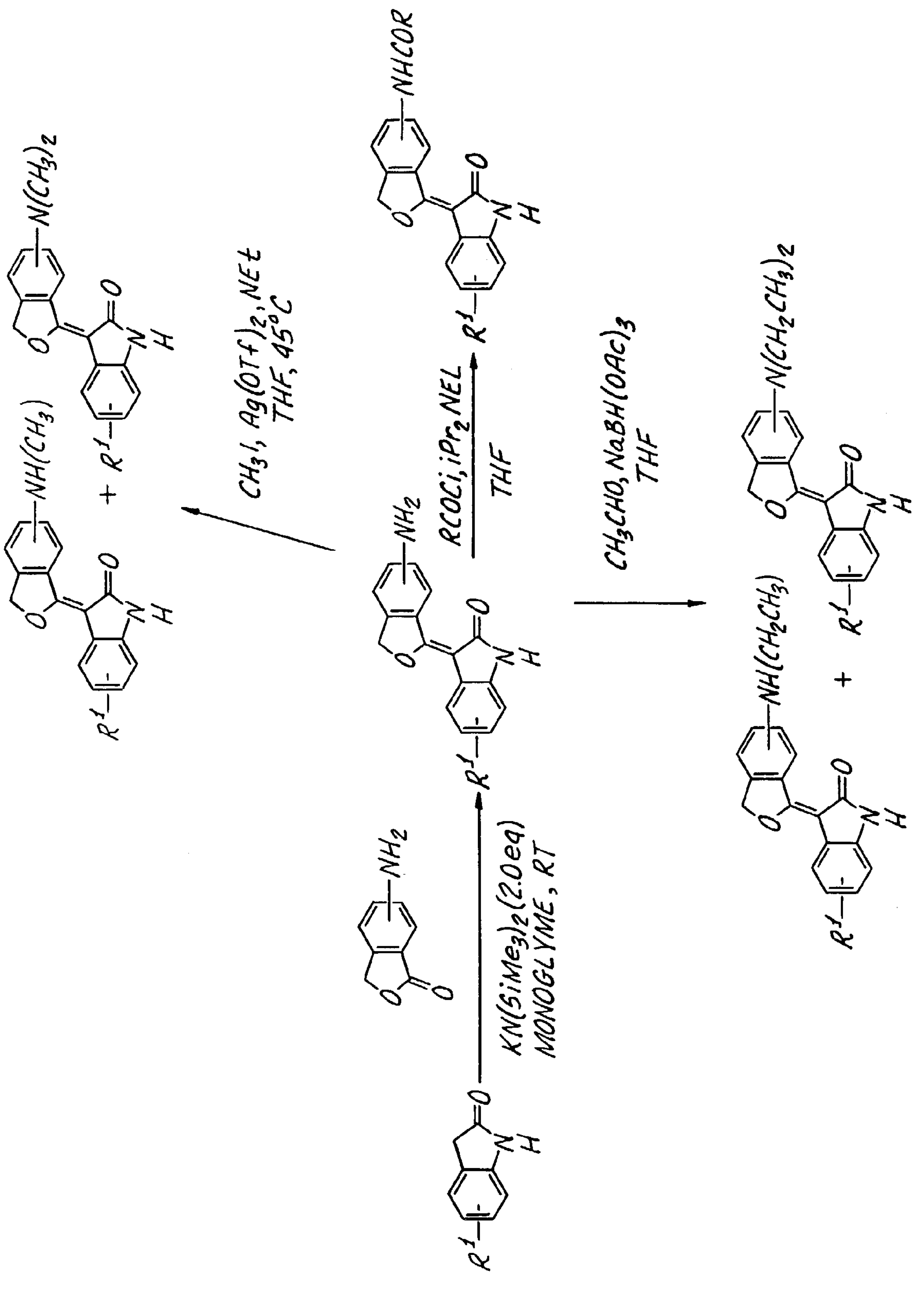
CH3I, Ag(OTf)2, NEt
THF, 45°C
RCOCl, iPr2NEt
THF
CH3CHO, NaBH(OAc)3
THF
KN(SiMe3)2 (2.0eq)
MONOGLYME, RT

(3Z)-3-(2,3-DIHYDRO-1H-INDEN-1-YLIDENE)-1,3-DIHYDRO-2H-INDOL-2-ONES AS KINASE INHIBITORS

CROSS REFERENCE TO RELATED APPLICATIONS

This patent application is a continuation in part of Ser. No. 10/116,309 which was filed Apr. 3, 2002 and issued as U.S. Pat. No. 6,541,504 on Apr. 1, 2003.

BACKGROUND OF THE INVENTION

1. Field of the Invention

The present invention relates to novel compounds capable of modulating, regulating and/or inhibiting tyrosine kinase signal transduction. The present invention is also directed to methods of regulating, modulating or inhibiting tyrosine kinases, whether of the receptor or non-receptor class, for the prevention and/or treatment of disorders related to unregulated tyrosine kinase signal transduction, including cell growth, metabolic, and blood vessel proliferative disorders.

2. Description of the Related Art

Protein tyrosine kinases (PTKs) comprise a large and diverse class of proteins having enzymatic activity. The PTKs play an important role in the control of cell growth and differentiation.

For example, receptor tyrosine kinase mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic homeostasis, and responses to the extracellular microenvironment).

With respect to receptor tyrosine kinases, it has been shown also that tyrosine phosphorylation sites function as high-affinity binding sites for SH2 (src homology) domains of signaling molecules. Several intracellular substrate proteins that associate with receptor tyrosine kinases (RTKs) have been identified. They may be divided into two principal groups: (1) substrates which have a catalytic domain; and (2) substrates which lack such domain but serve as adapters and associate with catalytically active molecules. The specificity of the interactions between receptors or proteins and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. These observations suggest that the function of each receptor tyrosine kinase is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

Aberrant expression or mutations in the PTKs have been shown to lead to either uncontrolled cell proliferation (e.g. malignant tumor growth) or to defects in key developmental processes. Consequently, the biomedical community has expended significant resources to discover the specific biological role of members of the PTK family, their function in differentiation processes, their involvement in tumorigenesis and in other diseases, the biochemical mechanisms underlying their signal transduction pathways activated upon ligand stimulation and the development of novel drugs.

Tyrosine kinases can be of the receptor-type (having extracellular, transmembrane and intracellular domains) or the non-receptor type (being wholly intracellular).

The RTKs comprise a large family of transmembrane receptors with diverse biological activities. The intrinsic function of RTKs is activated upon ligand binding, which results in phophorylation of the receptor and multiple cellular substrates, and subsequently in a variety of cellular responses.

At present, at least nineteen (19) distinct RTK subfamilies have been identified. One RTK subfamily, designated the HER subfamily, is believed to be comprised of EGFR, HER2, HER3 and HER4. Ligands to the Her subfamily of receptors include epithelial growth factor (EGF), TGF-α, amphiregulin, HB-EGF, betacellulin and heregulin.

A second family of RTKs, designated the insulin subfamily, is comprised of the INS-R, the IGF-1R and the IR-R. A third family, the "PDGF" subfamily includes the PDGF α and β receptors, CSFIR, c-kit and FLK-II. Another subfamily of RTKs, identified as the FLK family, is believed to be comprised of the Kinase insert Domain-Receptor fetal liver kinase-1 (KDR/FLK-1), the fetal liver kinase 4 (FLK-4) and the fms-like tyrosine kinase 1 (flt-1). Each of these receptors was initially believed to be receptors for hematopoietic growth factors. Two other subfamilies of RTKs have been designated as the FGF receptor family (FGFR1, FGFR2, FGFR3 and FGFR4) and the Met subfamily (c-met and Ron).

Because of the similarities between the PDGF and FLK subfamilies, the two subfamilies are often considered together. The known RTK subfamilies are identified in Plowman et al, 1994, DN&P 7(6): 334–339, which is incorporated herein by reference.

The non-receptor tyrosine kinases represent a collection of cellular enzymes which lack extracellular and transmembrane sequences. At present, over twenty-four individual non-receptor tyrosine kinases, comprising eleven (11) subfamilies (Src, Frk, Btk, Csk, Abl, Zap70, Fes/Fps, Fak, Jak, Ack and LIMK) have been identified. At present, the Src subfamily of non-receptor tyrosine kinases is comprised of the largest number of PTKs and include Src, Yes, Fyn, Lyn, Lck, Blk, Hck, Fgr and Yrk. The Src subfamily of enzymes has been linked to oncogenesis. A more detailed discussion of non-receptor tyrosine kinases is provided in Bolen, 1993, Oncogen 8: 2025–2031, which is incorporated herein by reference.

Many of the tyrosine kinases, whether an RTK or non-receptor tyrosine kinase, have been found to be involved in cellular signaling pathways leading to cellular signal cascades leading to pathogenic conditions, including cancer, psoriasis and hyper immune response.

In view of the surmised importance of PTKs to the control, regulation and modulation of cell proliferation the diseases and disorders associated with abnormal cell proliferation, many attempts have been made to identify receptor and non-receptor tyrosine kinase "inhibitors" using a variety of approaches, including the use of mutant ligands (U.S. Pat. No. 4,966,849), soluble receptors and antibodies (PCT Application No. WO 94/10202; Kendall & Thomas, 1994, Proc. Nat'l Acad. Sci 90: 10705–09; Kim, et al, 1993, Nature 362: 841–844), RNA ligands (Jellinek, et al, Biochemistry 33: 10450–56); Takano, et al, 1993, Mol. Bio. Cell 4:358A; Kinsella, et al, 1992, Exp. Cell Res. 199: 56–62; Wright, et al, 1992, J. Cellular Phys. 152: 448–57) and tyrosine kinase inhibitors (PCT Application Nos. WO 94/03427; WO 92/21660; WO 91/15495; WO 94/14808; U.S. Pat. No. 5,330,992; Mariani, et al, 1994, Proc. Am. Assoc. Cancer Res. 35: 2268).

More recently, attempts have been made to identify small molecules which act as tyrosine kinase inhibitors. For example, bis monocyclic, bicyclic or heterocyclic aryl compounds (PCT Application No. WO 92/20642), vinylene-azaindole derivatives (PCT Application No. WO 94/14808) and 1-cyclopropyl-4-pyridyl-quinolones (U.S. Pat. No. 5,330,992) have been described generally as tyrosine kinase inhibitors. Styryl compounds (U.S. Pat. No. 5,217,999), styryl-substituted pyridyl compounds (U.S. Pat. No. 5,302,606), certain quinazoline derivatives (EP Application No. 0 566 266 A1), seleoindoles and selenides (PCT Application No. WO 94/03427), tricyclic polyhydroxylic compounds (PCT Application No. WO 92/21660) and benzylphosphonic acid compounds (PCT Application No. WO 91/15495) have been described as compounds for use as tyrosine kinase inhibitors for use in the treatment of cancer.

The identification of effective small compounds which specifically inhibit signal transduction by modulating the activity of receptor and non-receptor tyrosine kinases to regulate and modulate abnormal or inappropriate cell proliferation is therefore desirable and one object of this invention.

Finally, certain small compounds are disclosed in U.S. Pat. Nos. 5,792,783; 5,834,504; 5,883,113; 5,883,116 and 5,886,020 as useful for the treatment of diseases related to unregulated TKS transduction. These patents are hereby incorporated by reference in its entirety for the purpose of disclosing starting materials and methods for the preparation thereof, screens and assays to determine a claimed compound's ability to modulate, regulate and/or inhibit cell proliferation, indications which are treatable with said compounds, formulations and routes of administration, effective dosages, etc.

BRIEF SUMMARY OF THE INVENTION

The present invention relates to organic molecules capable of modulating, regulating and/or inhibiting tyrosine kinase signal transduction. Such compounds are useful for the treatment of diseases related to unregulated TKS transduction, including cell proliferative diseases such as cancer, atherosclerosis, restenosis, metabolic diseases such as diabetes, inflammatory diseases such as psoriasis and chronic obstructive pulmonary disease, vascular proliferative disorders such as diabetic retinopathy, age-related macular degeneration and retinopathy of prematurity, autoimmune diseases and transplant rejection.

In one illustrative embodiment, the compounds of the present invention have the formula:

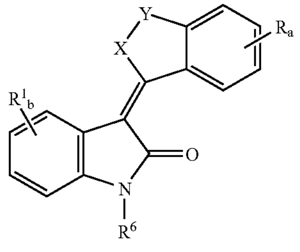

wherein X is O;

Y is $[C(R^2)_2]_c$;

$R^1$ is selected from the group consisting of halogen, aryl, $C_1$ to $C_8$ alkyl, $CF_3$, $OCF_3$, $OCF_2H$, $S(O)_fR^2$, $(CR^3R^4)_dC(O)OR^2$, $O(CR^3R^4)_eC(O)OR^2$, $NR^2(CR^3R^4)_dC(O)R^2$, $NR^2(CR^3R^4)_dC(O)OR^2$, $OP(O)(OR^2)_2$, $OC(O)OR^2$, $OCH_2O$, $NR^2(CH_2)_eN(R^2)_2$, $O(CH_2)_eN(R^2)_2$, $(CR^3R^4)_dCN$, $O(CR^3R^4)_eCN$, $(CR^3R^4)_dAr$, $NR^2(CR^3R^4)_dAr$, $O(CR^3R^4)_dAr$, $S(O)_f(CR^3R^4)_dAr$, $(CR^3R^4)_dSO_2R^2$, $(CR^3R^4)_dC(O)N(R^2)_2$, $NR^2(CR^3R^4)_dC(O)N(R^2)_2$, $O(CR^3R^4)_dC(O)N(R^2)_2$, $S(O)_f(CR^3R^4)_eC(O)N(R^2)_2$, $(CR^3R^4)_dOR^2$, $NR^2(CR^3R^4)_cOR^2$, $O(CR^3R^4)_eOR^2$, $S(O)_f(CR^3R^4)_dOR^2$, $C(O)(CR^3R^4)_dR^3$, $NR^2C(O)(CR^3R^4)_dR^3$, $OC(O)(CR^3R^4)_dN(R^2)_2$, $C(O)(CR^3R^4)_dN(R^2)_2 NR^2C(O)(CR^3R^4)_dN(R^2)_2$, $OC(O)(CR^3R^4)_dN(R^2)_2$, $(CR^3R^4)_dR^3$, $NR^2(CR^3R^4)_dR^3$, $O(CR^3R^4)_dR^3$, $S(O)_f(CR^3R^4)_dR^3$, $(CR^3R^4)_dN(R^2)_2$, $NR^2(CR^3R^4)_eN(R^2)_2$, $O(CR^3R^4)_eN(R^2)_2$, $S(O)_f(CR^3R^4)_dN(R^2)_2$, $N(R^5)_2$, $OR^5$, $C(O)R^5$, $S(O)_fR^5$;

$R^2$ is selected from the group consisting of hydrogen, $C_1$ to $C_8$ alkyl, $C_1$ to $C_8$ alkenyl, $C_1$ to $C_8$ alkynyl, $C_1$ to $C_4$ alkylol, lower alkylphenyl, phenyl, $(CR^3R^4)_dAr$, $(CR^3R^4)_dC(O)OR^2$, $(CR^3R^4)_dSO_2R^2$, $(CR^3R^4)_dOR^2$, $(CR^3R^4)_dOSO_2R$, $(CR^3R^4)_dP(O)(OR^2)_2$, $(CR^3R^4)_dR^2$, $(CR^3R^4)_eN(R^2)_2$, $(CR^3R^4)_eNR^2C(O)N(R^2)_2$; $N(R^2)_2$ may form a 3–7 membered heterocyclic ring, for example, pyrrolidine, 3-fluoropyrrolidine, piperidine, 4-fluoropiperidine, N-methylpiperazine, morpholine, 2,6-dimethylmorpholine, thiomorpholine. Said heterocyclic ring may be substituted with one or more of $R^3$;

$[C(R^2)_2[_c$ may form a 3–7 membered carbocyclic or heterocyclic ring;

R is selected from the group consisting of halogen, $C_1$ to $C_8$ alkyl, $CF_3$, $OCF_3$, $OCF_2H$, $(CR^3R^4)_dCN$, $NR^2(CR^3R^4)_eCN$, $O(CR^3R^4)_eCN$, $S(O)_fR^2$, $(CR^3R^4)_dC(O)OR^2$, $NR^2(CR^3R^4)_dC(O)OR^2$, $O(CR^3R^4)_dC(O)OR^2$, $S(O)_f(CR^3R^4)_dC(O)OR^2$, $(CR^3R^4)_dAr$, $NR^2(CR^3R^4)_dAr$, $O(CR^3R^4)_dAr$, $S(O)_f(CR^3R^4)_dAr$, $(CR^3R^4)_dSO_2R^2$, $NR^2$, $(CR^3R^4)_dS(O)_fR^2$, $O(CR^3R^4)_dS(O)_fR^2$, $S(O)_f(CR^3R^4)_eS(O)_fR^2$, $(CR^3R^4)_dC(O)N(R^2)_2$, $NR^2(CR^3R^4)_dC(O)N(R^2)_2$, $O(CR^3R^4)_dC(O)N(R^2)_2$, $S(O)_f(CR^3R^4)_eC(O)N(R^2)_2$, $(CR^3R^4)_dOR^2$, $NR^2(CR^3R^4)_eOR^2$, $O(CR^3R^4)_eOR^2$, $S(O)_f(CR^3R^4)_dOR^2$, $(CR^3R^4)_dOSO_2R^2$, $NR^2(CR^3R^4)_eOSO_2R^2$, $O(CR^3R^4)_eOSO_2R^2$, $S(O)_f(CR^3R^4)OSO_2R^2(CR^3R^4)_dP(O)(OR^2)_2$, $NR^2(CR^3R^4)_dP(O)(OR^2)_2$, $O(CR^3R^4)_dP(O)(OR^2)_2$, $S(O)_f(CR^3R^4)_eP(O)(OR^2)_2$, $C(O)(CR^3R^4)_dR^3$, $NR^2C(O)(CR^3R^4)_dR^3$, $OC(O)(CR^3R^4)_dN(R^2)_2$, $C(O)(CR^3R^4)_dN(R^2)_2$, $NR^2C(O)(CR^3R^4)_dN(R^2)_2$, $OC(O)(CR^3R^4)_dN(R^2)_2$, $(CR^3R^4)_dR^3$, $NR^2(CR^3R^4)_dR^3$, $O(CR^3R^4)_dR^3$, $S(O)_f(CR^3R^4)_dR^3$, $HNC(O)R^2$, $HN—C(O)OR^2$, $(CR^3R^4)_dN(R^2)_2$, $NR^2(CR^3R^4)_eN(R^2)_2$, $O(CR^3R^4)_eN(R^2)_2$, $S(O)_f(CR^3R^4)_dN(R^2)_2$, $OP(O)(R^2)_2$, $OC(O)OR^2$, $OCH_2O$, HN—CH=CH, $—N(COR^2)CH_2CH_2$, HC=N—NH, N=CH—S, $(CR^3R^4)_dC{=}C(CR^3R^4)_dR^2$, $(CR^3R^4)_dC{=}C(CR^3R^4)_dOR^2$, $(CR^3R^4)_dC{=}C(CR^3R^4)_dN(R^2)_2$, $(CR^3R^4)_dCC(CR^3R^4)_dR^2$, $(CR^3R^4)_dCC(CR^3R^4)_eOR^2$, $(CR^3R^4)_dCC(CR^3R^4)_eN(R^2)_2$, $(CR^3R^4)_dC(O)(CR^3R^4)_dR^2$, $(CR^3R^4)_dC(O)(CR^3R^4)_dOR^2$, $(CR^3R^4)_dC(O)(CR^3R^4)_dN(R^2)_2$, $R^3$ and $R^4$ may be selected from the group consisting of H, F, hydroxy, and $C_1$–$C_4$ alkyl or $CR^3R^4$ may represent a carbocyclic or heterocyclic ring of from 3 to 6 carbons, alternatively $(CR^3R^4)_d$ and $(CR^3R^4)_e$ may form a 3–7 membered carbocyclic or heterocyclic ring, preferably $R^3$ and $R^4$ are H, F, $CH_3$ or hydroxy;

$R^5$ is Ar—$R^1_b$ $R^6$ is selected from hydrogen, $C_1$–$C_8$ alkyl, hydroxyl methyl and phenyl;

b is 0 or an integer of from 1 to 2;

a is 0 or an integer of from 1 to 3;

c is an integer of from 1 to 2;

d is 0 or an integer of from 1 to 5;

e is an integer of from 1 to 4;

f is 0 or an integer of from 1 to 2, and further provided said alkyl or aryl radicals may be substituted with one or two halo, hydroxy, lower alkyloxy, lower alkyl amino or cycloalkylamino radicals wherein the cycloalkyl ring can include an enchained oxygen, sulfur or additional nitrogen atom and may be substituted with one or two halo or lower alkyl radicals;

and pharmaceutically acceptable salts thereof.

BRIEF DESCRIPTION OF THE DRAWING FIGURES

The FIG. shows a schematic of the preparation of the compounds of Examples 1 through 27.

DETAILED DESCRIPTION OF THE INVENTION

In one embodiment of the present invention $R^1$ is selected from the group consisting of H, i.e. b is 0; $CH_3$, F and Cl; preferably $R^1$ is H, F or Cl.

Preferably, a is 0 or R is selected from the group consisting of $NHCOR^7$ and $N(R^7)_2$ wherein $R^7$ is selected from the group consisting of hydrogen, $C_1$ to $C_4$ alkyl and phenyl, wherein said alkyl or phenyl may be substituted with hydroxy, methylol or amino substituents and more preferably $R^7$ is selected from the group consisting of hydrogen, methyl, ethyl, hydroxypropyl, and aminomethylol phenyl.

Preferably $R^6$ is H.

Preferably c is 1.

In another preferred embodiment of the present invention $R^1$ is selected from the group consisting of H, i.e. b is 0, F and Cl.

Preferably, a is 1 and R is selected from the group consisting of $(CR^3R^4)_dN(R^2)_2$, $NR^2(CR^3R^4)_dN(R^2)_2$, $O(CR^3R^4)_dN(R^2)_2$, $(CR^3R^4)_dCC(CR^3R^4)_dN(R^2)_2$, $NR^2C(O)(CR^3R^4)_dN(R^2)_2$.

Preferably $R^6$ is H.

Preferably c is 1.

In particular, the compounds of the present invention are selected from the compounds of Tables 1, 3, 4, 5 and 6 below.

TABLE 1

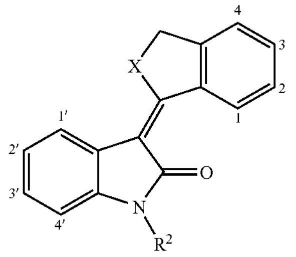

| Example Number | $R^2$ | 1 | 2 | 3 | 4 | 1' | 2' | 3' | 4' | X |
|---|---|---|---|---|---|---|---|---|---|---|
| Example 1 | H | H | H | H | H | H | H | H | H | O |
| Example 2 | H | H | H | H | H | H | Cl | H | H | O |
| Example 3 | H | H | H | H | H | $CH_3$ | H | H | H | O |
| Example 4 | H | H | H | H | H | H | F | H | H | O |
| Example 5 | H | H | $NH_2$ | H | H | H | H | H | H | O |
| Example 6 | H | H | $NHCOCH_3$ | H | H | H | H | H | H | O |
| Example 7 | H | H | $NHCOCH_2CH_2CH_3$ | H | H | H | H | H | H | O |
| Example 8 | H | H | NHCO-cyclopropyl | H | H | H | H | H | H | O |
| Example 9 | H | H | $NHCOCH_2CH_2CH_2Cl$ | H | H | H | H | H | H | O |
| Example 10 | H | H | $NHCOCH_2Ph$-4-$OCH_3$ | H | H | H | H | H | H | O |
| Example 11 | H | H | $NHCH_2CH_3$ | H | H | H | H | H | H | O |
| Example 12 | H | H | H | $NH_2$ | H | H | H | H | H | O |
| Example 13 | H | H | NHCOPh-3-$NH_2$,6-$CH_2OH$ | H | H | H | H | H | H | O |
| Example 14 | H | H | $NHCH_2CH_2CH_2OH$ | H | H | H | H | H | H | O |
| Example 15 | H | H | H | $NHCH_2CH_3$ | H | H | H | H | H | O |
| Example 16 | H | H | $NH_2$ | H | H | H | Cl | H | H | O |
| Example 17 | H | H | H | $NH_2$ | H | H | Cl | H | H | O |
| Example 18 | H | H | H | $NHCOCH_3$ | H | H | H | H | H | O |
| Example 19 | H | H | H | $NHCOCH_3$ | H | H | Cl | H | H | O |
| Example 20 | H | H | $NHCOCH_3$ | H | H | H | Cl | H | H | O |
| Example 21 | H | H | $N(CH_3)_2$ | H | H | H | H | H | H | O |
| Example 22 | H | H | $NHCH_3$ | H | H | H | H | H | H | O |
| Example 23 | H | H | H | $N(CH_3)_2$ | H | H | H | H | H | O |
| Example 24 | H | H | H | $NHCH_3$ | H | H | H | H | H | O |
| Example 26 | H | H | $NHCOCH_2CH_2CH_2Cl$ | H | H | H | H | H | H | O |
| Example 27 | H | H | $N(CH_2CH_3)_2$ | H | H | H | H | H | H | O |

The present invention is further directed to pharmaceutical compositions comprising a pharmaceutically effective amount of the above-described compounds and a pharmaceutically acceptable carrier or excipient. Such a composition is believed to modulate signal transduction by a tyrosine kinase, either by inhibition of catalytic activity, affinity to ATP or ability to interact with a substrate.

More particularly, the compositions of the present invention may be included in methods for treating diseases comprising proliferation, fibrotic or metabolic disorders, for example cancer, fibrosis, psoriasis, atherosclerosis, arthritis, and other disorders related to abnormal vasculogenesis and/or angiogenesis, such as diabetic retinopathy.

The following defined terms are used throughout this specification:

"Ac" refers to acetyl.

"Ar" refers to aryl.

"Tf" refers to triflate.

"Me" refers to methyl.

"Et" refers to ethyl.

"tBu" refers to t-butyl.

"iPr" refers to I-propyl.

"Ph" refers to phenyl.

"Pharmaceutically acceptable salt" refers to those salts which retain the biological effectiveness and properties of the free bases and which are obtained by reaction with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Certain "pharmaceutically acceptable salts" are the salts of free acid, e.g. the sodium salt of a carboxylic acid.

"Alkyl" refers to a straight-chain, branched or cyclic saturated aliphatic hydrocarbon. Preferably, the alkyl group has 1 to 12 carbons. More preferably, it is a lower alkyl of from 1 to 8 carbons, most preferably 1 to 4 carbons. Typical alkyl groups include methyl, ethyl, propyl, isopropyl, butyl, isobutyl, tertiary butyl, pentyl, hexyl and the like. The alkyl group may be optionally substituted with one or more substituents are selected from the group consisting of hydroxyl, cyano, alkoxy, =O, =S, $NO_2$, halogen, dimethyl amino, and SH.

"Alkenyl" refers to a straight-chain, branched or cyclic unsaturated hydrocarbon group containing at least one carbon-carbon double bond. Preferably, the alkenyl group has 1 to 12 carbons. More preferably it is a lower alkenyl of from 1 to 8 carbons, most preferably 1 to 4 carbons. The alkenyl group may be optionally substituted with one or more substituents selected from the group consisting of hydroxyl, cyano, alkoxy, =O, =S, $NO_2$, halogen, dimethyl amino, and SH.

"Alkynyl" refers to a straight-chain, branched or cyclic unsaturated hydrocarbon containing at least one carbon-carbon triple bond. Preferably, the alkynyl group has 1 to 12 carbons. More preferably it is a lower alkynyl of from 1 to 8 carbons, most preferably 1 to 4 carbons. The alkynyl group may be optionally substituted with one or more substituents selected from the group consisting of hydroxyl, cyano, alkoxy, =O, =S, $NO_2$, halogen, dimethyl amino, and SH.

"Alkoxyl" refers to an "O-alkyl" group.

"Aryl" refers to an aromatic group which has at least one ring having a conjugated pi electron system and includes carbocyclic aryl, heterocyclic aryl and biaryl groups. The aryl group may be optionally substituted with one or more substituents selected from the group consisting of halogen, trihalomethyl, hydroxyl, SH, OH, $NO_2$, amine, thioether, cyano, alkoxy, alkyl, and amino.

"Alkaryl" refers to an alkyl that is covalently joined to an aryl group. Preferably, the alkyl is a lower alkyl.

"Carbocyclic aryl" refers to an aryl group wherein the ring atoms are carbon.

"Heterocyclic aryl" refers to an aryl group having from 1 to 4 heteroatoms as ring atoms, the remainder of the ring atoms being carbon. Heteroatoms include oxygen, sulfur, and nitrogen. Thus, heterocyclic aryl groups include furanyl, thienyl, pyridyl, pyrrolyl, N-lower alkyl pyrrolo, pyrimidyl, pyrazinyl, imidazolyl, tetrazoyl and the like.

"Hydrocarbyl" refers to a hydrocarbon radical having only carbon and hydrogen atoms. Preferably, the hydrocarbyl radical has from 1 to 20 carbon atoms, more preferably from 1 to 12 carbon atoms and most preferably from 1 to 8 carbon atoms.

"Substituted hydrocarbyl" refers to a hydrocarbyl radical wherein one or more, but not all, of the hydrogen and/or the carbon atoms are replaced by a halogen, nitrogen, oxygen, sulfur or phosphorus atom or a radical including a halogen, nitrogen, oxygen, sulfur or phosphorus atom, e.g. fluoro, chloro, cyano, nitro, hydroxyl, phosphate, thiol, etc.

"Amide" refers to —C(O)—NH—R' or —NH—C(O)R', wherein R' is alkyl, aryl, alkylaryl or hydrogen.

"Thioamide" refers to —C(S)—NH—R' or —NH—C(S)R', wherein R' is alkyl, aryl, alkylaryl or hydrogen.

"Amine" refers to a —N(R")R'" group, wherein R" and R'" are independently selected from the group consisting of alkyl, aryl, and alkylaryl.

"Thioether" refers to —S—R", wherein R" is alkyl, aryl, or alkylaryl.

"Sulfonyl" refers to $—S(O)_2—R''''$, where R"" is aryl, C(CN)=C-aryl, $CH_2CN$, alkyaryl, sulfonamide, NH-alkyl, NH-alkylaryl, or NH-aryl.

The present invention relates to compounds capable of regulating and/or modulating tyrosine kinase signal transduction and more particularly receptor and non-receptor tyrosine kinase signal transduction.

Receptor tyrosine kinase mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic effects and responses to the extracellular microenvironment).

It has been shown that tyrosine phosphorylation sites in growth factor receptors function as high-affinity binding sites for SH2 (src homology) domains of signaling molecules. Several intracellular substrate proteins that associate with receptor tyrosine kinases have been identified. They may be divided into two principal groups: (1) substrates which have a catalytic domain; and (2) substrates which lack such domain but serve as adapters and associate with catalytically active molecules. The specificity of the interactions between receptors and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. These observations suggest that the function of each receptor tyrosine kinase is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

Tyrosine kinase signal transduction results in, among other responses, cell proliferation, differentiation and metabolism. Abnormal cell proliferation may result in a wide array of disorders and diseases, including the development of neoplasia such as carcinoma, sarcoma, leukemia, glioblastoma, hemangioma, psoriasis, arteriosclerosis, arthritis and diabetic retinopathy (or other disorders related to uncontrolled angiogenesis and/or vasculogenesis, e.g. macular degeneration).

This invention is therefore directed to compounds which regulate, modulate and/or inhibit tyrosine kinase signal transduction by affecting the enzymatic activity of the RTKs and/or the non-receptor tyrosine kinases and interfering with the signal transduced by such proteins. More particularly, the present invention is directed to compounds which regulate, modulate and/or inhibit the RTK and/or non-receptor tyrosine kinase mediated signal transduction pathways as a therapeutic approach to cure many kinds of solid tumors, including but not limited to carcinoma, sarcoma, leukemia, erythroblastoma, glioblastoma, meningioma, astrocytoma, melanoma and myoblastoma. Indications may include, but are not limited to brain cancers, bladder cancers, ovarian cancers, gastric cancers, pancreas cancers, colon cancers, blood cancers, lung cancers and bone cancers.

Biological data for the compounds of the present invention was generated by use of the following assays.

VEGF Stimulated $Ca^{++}$ Signal in Vitro

Automated FLIPR (Fluorometric Imaging Plate Reader) technology was used to screen for inhibitors of VEGF induced increases in intracellular calcium levels in fluorescent dye loaded endothelial cells. HUVEC (human umbilical vein endothelial cells) (Clonetics) were seeded in 96-well fibronectin coated black-walled plates overnight @ 37° C./5% $CO_2$. Cells were loaded with calcium indicator Fluo-4 for 45 minutes at 37° C. Cells were washed 4 times (Original Cell Wash, Labsystems) to remove extracellular dye. For screening, cells were pre-incubated with test agents for 30 minutes at a single concentration (10 uM) or at concentrations ranging from 0.01 to 10.0 uM, followed by VEGF stimulation (5 ng/mL). Changes in fluorescence at 516 nm were measured simultaneously in all 96 wells using a cooled CCD camera. Data were generated by determining max-min fluorescence levels for unstimulated, stimulated, and drug treated samples. $IC_{50}$ values for test compounds were calculated from % inhibition of VEGF stimulated responses in the absence of inhibitor.

Protocol for KDR Assay:

The cytoplasmic domain of the human VEGF receptor (VEGFR-2) was expressed as a Histidine-tagged fusion protein following infection of insect cells using an engineered baculovirus. His-VEGFR-2 was purified to homogeneity, as determined by SDS-PAGE, using nickel resin chromatography. Kinase assays were performed in 96 well microtiter plates that were coated overnight with 30 μg of poly-Glu-Tyr (4:1) in 10 mM Phosphate Buffered Saline (PBS), pH 7.2–7.4. The plates were incubated with 1% BSA and then washed four times with PBS prior to starting the reaction. Reactions were carried out in 120 μL reaction volumes containing 3.6 μM ATP in kinase buffer (50 mM Hepes pH 7.4, 20 mM $MgCl_2$, 0.1 mM $MnCl_2$ and 0.2 mM $Na_3VO_4$). Test compounds were reconstituted in 100% DMSO and added to the reaction to give a final DMSO concentration of 5%. Reactions were initiated by the addition 0.5 ng of purified protein. Following a ten minute incubation at 25° C., the reactions were washed four times with PBS containing 0.05% Tween-20. 100 μl of a monoclonal anti-phosphotyrosine antibody-peroxidase conjugate was diluted 1:10000 in PBS-Tween-20 and added to the wells for 30 minutes. Following four washes with PBS-Tween-20, 100 μl of 0-Phenylenediamine Dihydrochloride in Phosphate-citrate buffer, containing urea hydrogen peroxide, was added to the wells for 7 minutes as a colorimetric substrate for the peroxidase. The reaction was terminated by the addition of 100 μl of 2.5N $H_2SO_4$ to each well and read using a microplate ELISA reader set at 492 nm. $IC_{50}$ values for compound inhibition were calculated directly from graphs of optical density (arbitrary units) versus compound concentration following subtraction of blank values.

The results of said assays are set forth in Table 2, below.

TABLE 2

In vitro VEGF Inhibition

| Example Number | VEGF mean $IC_{50}$(μM) (Cell based assay, $Ca^{++}$) | VEGF (% inhibition @ 10 uM) (Cell based assay, $Ca^{++}$) | VEGF mean $IC_{50}$(μM) (Kinase assay, KDr with BSA) |
|---|---|---|---|
| Example 1 | 0.11 | 99 | |
| Example 2 | 0.05 | 98 | |
| Example 3 | 0.685 | 95 | |
| Example 4 | 0.055 | 99 | 0.073 |
| Example 5 | 0.04 | 98 | 0.13 |
| Example 6 | 1.225 | 97 | 1.11 |
| Example 7 | | 5 | 9.78 |
| Example 8 | | 48 | 0.85 |
| Example 9 | | 35 | 3.25 |
| Example 10 | | 50 | 8.02 |
| Example 11 | 0.78 | 99 | 0.66 |
| Example 12 | 0.04 | 98 | 0.065 |
| Example 13 | 2.095 | 99 | 1.34 |
| Example 14 | 0.85 | 100 | 0.64 |
| Example 15 | 0.051 | 95 | 0.037 |
| Example 16 | 0.06 | 99 | 0.015 |
| Example 17 | 0.055 | 98 | 0.139 |
| Example 18 | 0.04 | 97 | 0.063 |
| Example 19 | 0.05 | 99 | 0.066 |
| Example 20 | 0.097 | 99 | 0.39 |
| Example 21 | 1.31 | 94 | 1.69 |
| Example 22 | 0.29 | 96 | 0.17 |
| Example 23 | 0.096 | 96 | 0.043 |
| Example 24 | 0.073 | 98 | 0.061 |
| Example 25 | | | |
| Example 26 | | | |
| Example 27 | | | |

As shown in Table 2, above, the compounds of Examples 1–6, 11–24 and 16–20 are preferred as they show % inhibition of VEGF>90% or VEGF $IC_{50}$<1.0 μM in either the cell or kinase assay.

EXAMPLES

Example 1

3-(3H-isobenzofuran-1-ylidene)-1,3-dihydro-indol-2-one

To a suspension of sodium hydride (6.0 g, 150 mmol, 60% in mineral oil) in 300 mL DMF was added oxindole (10.0 g, 75.1 mmol) in 50 mL DMF over 8 min. After stirring for 15 min at room temperature, a solution of phthalide (13.1 g, 97.6 mmol) in 50 mL DMF was added over 1 min. The mixture was stirred for 1.25 h, then poured into 1100 mL $H_2O$. Addition of 4% aqueous HCl solution gave a yellow solid which was filtered and rinsed with $H_2O$ to give the title compound (8.75 g, 47%).

$^1H$ NMR (500 MHz, DMSO-D6) δ 10.41 (s, 1 H), 9.65 (d, J=8.1 Hz, 1 H), 7.83 (d, J=7.6 Hz, 1 H), 7.65 (m, 2H), 7.55 (m, 1 H), 7.10 (ddd, J=7.6, 7.6, 1.0 Hz, 1 H), 6.95 (ddd, J=7.6, 7.6, 1.0 Hz, 1 H), 6.81 (d, J=7.6 Hz, 1 H), 5.81 (s, 2 H).

Example 2

5-Chloro-3-(3H-isobenzofuran-1-ylidene)-1,3-dihydro-indol-2-one

To a solution containing 5-chlorooxindole (0.30 g, 1.79 mmol) and phthalide (0.312 g, 2.33 mmol) in 6.0 mL of dimethylformamide (DMF) was added 3.76 mL of sodium hexamethyldisilazane (1.0 M in tetrahydrofuran (THF)) over 1 min. The solution was stirred at room temperature for 25 min and then 85 mg (0.634 mmol) phthalide was added. After an additional 20 min at room temperature the mixture was poured into 70 mL of 4% aqueous HCl solution to give a yellow solid. The aqueous mixture was extracted with EtOAc and the organic phase washed with saturated $NaHCO_3$, brine and then dried with $Na_2SO_4$. After removal of the solvent in vacuo, the solid residue was recrystallized from MeOH/EtOAc to afford the title (141 mg, 28%) compound as a yellow solid.

$^1H$ NMR (500 MHz, DMSO-D6) δ ppm 5.87 (s, 2 H) 6.84 (d, J=8.30 Hz, 1 H) 7.16 (dd, J=8.18, 2.32 Hz, 1 H) 7.60 (m, 1 H) 7.70 (m, 2 H) 7.82 (d, J=2.20 Hz, 1 H) 9.65 (d, J=8.06 Hz, 1 H) 10.58 (s, 1 H).

Example 3

3-(3H-Isobenzofuran-1-ylidene)-4-methyl-1,3-dihydro-indol-2-one

To a solution containing 4-methyloxindole (0.15 g, 1.02 mmol) and phthalide (0.178 g, 1.33 mmol) in 3.0 mL DMF was added 2.14 mL of sodium hexamethyldisilazane (1.0 M in tetrahydrofuran (THF)) over 1 min. The solution was stirred at room temperature for 30 min and then poured into 50 mL of 4% HCl to give a yellow solid. The aqueous mixture was extracted with EtOAc and the organic phase washed with saturated $NaHCO_3$, $H_2O$, dilute HCl, brine and the solution dried with $Na_2SO_4$. The solvent was removed in vacuo and the solid obtained was purified by chromatography (silica gel, $CHCl_3$/EtOAc, 7:3). The solid obtained was recrystallized from EtOAc/hexanes to afford the title compounds (3.8 mg) as a yellow solid.

$^1H$ NMR (500 MHz, $CDCl_3$) δ ppm 2.58 (s, 3 H) 5.62 (s, 2 H) 6.70 (d, J=7.81 Hz, 1 H) 6.86 (d, J=7.32 Hz, 1 H) 7.07 (t, J=7.57 Hz, 1 H) 7.45 (m, 1 H) 7.56 (m, 2H) 7.68 (s, 1 H) 9.70 (d, J=6.83 Hz, 1 H).

Example 4

5-Fluoro-3-(3H-isobenzofuran-1-ylidene)-1,3-dihydro-indol-2-one

To a solution at 0° C. containing 5-fluorooxindole (0.30 g, 1.99 mmol) and phthalide (0.400 g, 2.98 mmol) in 5.0 mL DMF was added 4.2 mL of sodium hexamethyldisilazane (1.0 M in THF) over 5 min. The solution was stirred at room temperature for 3 h and then quenched into cold 1.0 M aqueous HCl solution to give a yellow solid. The solid was collected and then purified by chromatography (silica gel, hexanes/EtOAc, 4:1) to afford the title compound (32 mg, 6%) as a yellow solid.

$^1H$ NMR (500 MHz, DMSO-$d_6$) δ ppm 5.83 (s, 2 H) 6.78 (dd, J=8.42, 4.39 Hz, 1 H) 6.93 (m, 1 H) 7.57 (m, 2 H) 7.68 (m, 2 H) 9.64 (d, J=8.05 Hz, 1 H) 10.44 (s, 1 H)

Example 5

3-(6-Amino-3H-isobenzofuran-1-ylidene)-1,3-dihydro-indol-2-one

To a solution containing oxindole (0.5 g, 3.76 mmol) in 7.5 mL DMF was added 7.51 mL of sodium hexamethyldisilazane (1.0 M in THF) over 3 min. After stirring 10 min at room temperature, a solution of 6-aminophthalide (0.672 g, 4.51 mmol) in 4.0 mL DMF was added over 3 min. The reaction was stirred for 50 min at room temperature and then poured into 4% HCl to give a yellow solid. The solid was filtered to a wet cake and then partitioned between EtOAc and saturated $NaHCO_3$. Then the mixture was heated to dissolve the solid. The organic phase was washed with $H_2O$, brine and then dried with $Na_2SO_4$. The solvent was removed in vacuo and the resultant solid triturated with $CHCl_3$ to afford the title compound (445 mg, 45%) as a yellow solid.

$^1H$ NMR (500 MHz, DMSO-D6) δ ppm 5.39 (s, 2 H) 5.61 (s, 2 H) 6.80 (d, J=7.32 Hz, 1 H) 6.89 (dd, J=8.06, 2.20 Hz, 1 H) 6.93 (td, J=7.57, 0.98 Hz, 1 H) 7.08 (td, J=7.69, 1.22 Hz, 1 H) 7.28 (d, J=8.30 Hz, 1 H) 7.82 (d, J=7.32 Hz, 1 H) 8.86 (d, J=1.95 Hz, 1 H) 10.32 (s, 1 H).

Example 6

[3-(2-Oxo-1,2-dihydro-indol-3-ylidene)-1,3-dihydro-isobenzofuran-5-yl]-acetamide To a solution of 3-(6-Amino-3H-isobenzofuran-1-ylidene)-1,3-dihydro-indol-2-one (50.0 mg, 0.189 mmol) and N,N-diisopropylethylamine (98.8 µL, 0.567 mmol) in 2.0 mL THF was added acetyl chloride (13.4 µL, 0.189 mmol). After stirring at room temperature for 1 h, the slurry was partitioned between $NaHCO_3$ solution and EtOAc (warmed to dissolve solid). The organic phase was washed with $H_2O$, 4% aqueous HCl solution, $H_2O$, saturated $NaHCO_3$, brine and dried with $Na_2SO_4$. After concentrating in vacuo the residue was triturated with EtOAc to give the title compound (47.4 mg, 82%) as a yellow solid.

$^1H$ NMR (500 MHz, DMSO-D6) δ ppm 2.09 (s, 3 H) 5.75 (s, 2 H) 6.83 (d, J=7.81 Hz, 1 H) 6.96 (td, J=7.57, 0.98 Hz, 1 H) 7.11 (td, J=7.69, 1.22 Hz, 1 H) 7.57 (d, J=8.30 Hz, 1 H) 7.83 (d, J=7.81 Hz, 1 H) 8.10 (dd, J=8.30, 1.95 Hz, 1 H) 9.59 (d, J=1.95 Hz, 1 H) 10.29 (s, 1 H) 10.41 (s, 1 H).

Example 7

N-[3-(2-Oxo-1,2-dihydro-indol-3-ylidene)-1,3-dihydro-isobenzofuran-5-yl]-butyramide To a solution of 3-(6-Amino-3H-isobenzofuran-1-ylidene)-1,3-dihydro-indol-2-one (50.0 mg, 0.189 mmol) and N,N-diisopropylethylamine (98.8 µL, 0.567 mmol) in 2.0 mL THF was added butyryl chloride (19.6 µL, 0.189 mmol). After stirring at room temperature for 1 h, the slurry was filtered and rinsed with MEOH and EtOAc/hexanes (1:1) to afford the title compound (46.2 mg, 73%) as a yellow solid.

$^1H$ NMR (500 MHz, DMSO-D6) δ ppm 0.93 (t, J=7.57 Hz, 3 H) 1.63 (m, 2 H) 2.34 (t, J=7.32 Hz, 2 H) 5.75 (s, 2 H) 6.83 (d, J=7.81 Hz, 1 H) 6.96 (m, 1 H) 7.11 (td, J=7.57, 1.46 Hz, 1 H) 7.57 (d, J=8.30 Hz, 1 H) 7.83 (d, J=7.32 Hz, 1 H) 8.11 (dd, J=8.30, 1.46 Hz, 1 H) 9.61 (d, J=1.95 Hz, 1 H) 10.23 (s, 1 H) 10.40 (s, 1 H).

Example 8

Cyclopropanecarboxylic acid [3-(2-oxo-1,2-dihydro-indol-3-ylidene)-1,3-dihydro-isobenzofuran-5-yl]-amide To a solution of 3-(6-Amino-3H-isobenzofuran-1-ylidene)-1,3-dihydro-indol-2-one (50.0 mg, 0.189 mmol) and N,N-diisopropylethylamine (98.8 μL, 0.567 mmol) in 2.0 mL THF was added cyclopropane carbonyl chloride (17.2 μL, 0.189 mmol). After stirring at room temperature for 1 h, the slurry was warmed briefly, stirred 10 min at room temperature, filtered and rinsed with MeOH and EtOAc/hexanes (1:1) to afford the title compound (44.7 mg, 71%) as a yellow solid.

$^1H$ NMR (500 MHz, DMSO-D6) δ ppm 0.82 (m, 4 H) 1.89 (m, 1 H) 5.75 (s, 2 H) 6.83 (d, J=7.32 Hz, 1 H) 6.96 (m, 1 H) 7.12 (m, 1 H) 7.57 (d, J=8.30 Hz, 1 H) 7.83 (d, J=7.32 Hz, 1 H) 8.08 (d, J=8.30 Hz, 1 H) 9.63 (d, J=1.46 Hz, 1 H) 10.40 (s, 1 H) 10.54 (s, 1 H).

Example 9

4-Chloro-N-[3-(2-oxo-1,2-dihydro-indol-3-ylidene)-1,3-dihydro-isobenzofuran-5-yl]-butyramide To a solution of 3-(6-Amino-3H-isobenzofuran-1-ylidene)-1,3-dihydro-indol-2-one (50.0 mg, 0.189 mmol) and N,N-diisopropylethylamine (98.8 μL, 0.567 mmol) in 2.0 mL THF was added 4-chlorobutyryl chloride (21.2 μL, 0.189 mmol). After stirring at room temperature for 1 h, the slurry was filtered and rinsed with MeOH and EtOAc/hexanes (1:1) to afford the title compound (58.8 mg, 84%) as a yellow solid.

$^1H$ NMR (500 MHz, DMSO-D6) δ ppm 2.06 (m, 2 H) 2.54 (t, J=7.32 Hz, 2 H) 3.72 (t, J=6.35 Hz, 2 H) 5.75 (s, 2 H) 6.83 (d, J=7.32 Hz, 1 H) 6.96 (m, 1 H) 7.12 (td, J=7.69, 1.22 Hz, 1 H) 7.58 (d, J=8.30 Hz, 1 H) 7.83 (d, J=7.32 Hz, 1 H) 8.10 (dd, J=8.30, 1.46 Hz, 1 H) 9.63 (d, J=1.95 Hz, 1 H) 10.34 (s, 1 H) 10.40 (s, 1 H).

Example 10

2-(4-Methoxy-phenyl)-N-[3-(2-oxo-1,2-dihydro-indol-3-ylidene)-1,3-dihydro-isobenzofuran-5-yl]-acetamide To a solution of 3-(6-Amino-3H-isobenzofuran-1-ylidene)-1,3-dihydro-indol-2-one (50.0 mg, 0.189 mmol) and N,N-diisopropylethylamine (98.8 μL, 0.567 mmol) in 2.0 mL THF was added 4-methoxyphenylacetyl chloride (28.9 μL, 0.189 mmol). After stirring at room temperature for 1 h, the slurry was warmed briefly, stirred 10 min at room temperature, filtered and rinsed with MeOH and EtOAc/hexanes (1:1) to afford the title compound (48.3 mg, 62%) as a yellow solid.

$^1H$ NMR (500 MHz, DMSO-D6) δ ppm 3.62 (s, 2 H) 3.73 (s, 3 H) 5.75 (s, 2 H) 6.83 (d, J=7.81 Hz, 1 H) 6.90 (m, 2 H) 6.96 (td, J=7.57, 0.98 Hz, 1 H) 7.12 (td, J=7.57, 0.98 Hz, 1 H) 7.28 (m, 2 H) 7.57 (d, J=8.79 Hz, 1 H) 7.83 (d, J=7.32 Hz, 1 H) 8.11 (dd, J=8.30, 1.95 Hz, 1 H) 9.63 (d, J=1.46 Hz, 1 H) 10.40 (s, 1 H) 10.47 (s, 1 H).

Example 11

3-(6-Ethylamino-3H-isobenzofuran-1-ylidene)-1,3-dihydro-indol-2-one

A mixture of 3-(6-Amino-3H-isobenzofuran-1-ylidene)-1,3-dihydro-indol-2-one (50.0 mg, 0.189 mmol), acetaldehyde (10.0 mg, 0.227 mmol), and sodium triacetoxyborohydride (52.1 mg, 0.246 mmol) was stirred at room temperature for 2.5 h. The reaction was then partitioned between EtOAc and $H_2O$. The organic phase was washed with $H_2O$, brine and then dried with $Na_2SO_4$. The solvent was removed in vacuo and the residue recrystallized from EtOAc/hexanes to afford the title compound (21.6 mg, 39%) as a yellow solid.

$^1H$ NMR (500 MHz, DMSO-D6) δ ppm 1.22 (t, J=7.08 Hz, 3 H) 3.12 (m, 2 H) 5.63 (s, 2 H) 5.91 (t, J=5.37 Hz, 1 H) 6.82 (d, J=7.32 Hz, 1 H) 6.92 (m, 2 H) 7.09 (m, 1 H) 7.32 (d, J=8.30 Hz, 1 H) 7.82 (d, J=7.32 Hz, 1 H) 8.94 (d, J=1.95 Hz, 1 H) 10.28 (s, 1 H).

Example 12

3-(5-Amino-3H-isobenzofuran-1-ylidene)-1,3-dihydro-indol-2-one

To a solution containing oxindole (0.5 g, 3.76 mmol) in 7.5 mL DMF was added 7.51 mL of sodium hexamethyldisilazane (1.0 M in THF) over 3 min. After stirring 10 min at room temperature, a solution of 5-aminophthalide (0.672 g, 4.51 mmol) in 4.0 mL DMF was added over 3 min. The reaction was stirred for 30 min at room temperature and then poured into 4% aqueous HCl solution to give a yellow cloudy solution. After stirring the mixture 3 min, the solution was made basic by adding saturated $NaHCO_3$. The yellow solid was filtered, washed with $H_2O$, and then dissolved in $CHCl_3$/MeOH. The solvent was removed in vacuo and the solid purified by chromatography (silica gel, $CHCl_3$/MeOH, 95:5) to give the title compound (345 mg, 35%) as a yellow solid.

$^1H$ NMR (500 MHz, DMSO-D6) δ ppm 5.60 (s, 2 H) 6.27 (s, 2 H) 6.67 (m, 2 H) 6.78 (d, J=7.32 Hz, 1 H) 6.89 (m, 1 H) 7.01 (td, J=7.57, 1.46 Hz, 1 H) 7.74 (d, J=7.32 Hz, 1 H) 9.33 (d, J=9.28 Hz, 1 H) 10.19 (s, 1 H).

Example 13

5-Amino-2-hydroxymethyl-N-[3-(2-oxo-1,2-dihydro-indol-3-ylidene)-1,3-dihydro-isobenzofuran-5-yl]-benzamide To a solution containing oxindole (1.5 g, 11.3 mmol) in 23 mL DMF was added 22.54 mL of sodium hexamethyldisilazane (1.0 M in THF) over 5 min. After stirring 5 min at rt, a solution of 6-aminophthalide (2.017 g, 13.5 mmol) in 11.0 mL DMF was added over 4 min. The reaction was stirred for 30 min at room temperature and then quenched into 4% aqueous HCl solution. The aqueous solution was neutralized to pH 6 with 1 M NaOH and then made basic with saturated $NaHCO_3$. The solid was filtered and washed with $H_2O$ and then partitioned between EtOAc and saturated $NaHCO_3$ (heated to dissolve the solid). The organic phase was washed with $H_2O$, brine and then dried with $Na_2SO_4$. The solvent was removed in vacuo and the solid triturated with $CHCl_3$.

The yellow solid was filtered (1.2 g) (Example 5) and the filtrate concentrated in vacuo. The solid (0.88 g) obtained from the filtrate was purified by chromatography ($CHCl_3$/MeOH, 96:4) to afford the lower $R_f$ product, which after trituration with $CHCl_3$, gave the title compound (7.6 mg) as a yellow solid.

$^1$H NMR (500 MHz, DMSO-D6) δ ppm 4.48 (d, J=5.37 Hz, 2 H) 5.13 (t, J=5.37 Hz, 1 H) 5.27 (s, 2 H) 5.78 (s, 2 H) 6.66 (dd, J=8.30, 2.44 Hz, 1 H) 6.83 (m, 2 H) 6.96 (t, J=7.57 Hz, 1 H) 7.12 (t, J=7.57 Hz, 1 H) 7.16 (d, J=8.30 Hz, 1 H) 7.62 (d, J=8.30 Hz, 1 H) 7.84 (d, J=7.81 Hz, 1 H) 8.04 (d, J=8.30 Hz, 1 H) 9.83 (s, 1 H) 10.35 (s, 1 H) 10.70 (s, 1 H).

Example 14

3-[6-(3-Hydroxy-propylamino)-3H-isobenzofuran-1-ylidene]-1,3-dihydro-indol-2-one A mixture of 3-(6-Amino-3H-isobenzofuran-1-ylidene)-1,3-dihydro-indol-2-one (25.0 mg, 0.095 mmol), 3-bromo-1-propanol (85.5 μL, 0.946 mmol), and silver sulfate (59.0 mg, 0.189 mmol) in 0.8 mL DMF was heated at 120° C. for 1.5 h. The mixture was partitioned between EtOAc and $H_2O$ and the organic layer separated from the silver salts. The solution was washed with $H_2O$, brine and then dried with $Na_2SO_4$. Concentrating the solution in vacuo gave a residue which was purified by chromatography (silica gel, $CHCl_3$/MeOH, 96:4) to give the title compound (3 mg, 10%) as a yellow solid.

$^1$H NMR (500 MHz, $CDCl_3$) δ ppm 1.92 (m, 2 H) 3.23 (t, J=6.59 Hz, 1 H) 3.71 (q, J=5.86 Hz, 2 H) 4.09 (t, J=6.35 Hz, 2 H) 5.72 (s, 2 H) 6.88 (d, J=7.32 Hz, 1 H) 7.07 (t, J=7.32 Hz, 1 H) 7.20 (m, 1 H) 7.38 (dd, J=7.81, 1.95 Hz, 1 H) 7.47 (s, 1 H) 7.51 (d, J=7.81 Hz, 1 H) 7.98 (d, J=7.81 Hz, 1 H) 8.57 (s, 1 H) 9.82 (d, J=2.44 Hz, 1 H).

Example 15

3-(5-Ethylamino-3H-isobenzofuran-1-ylidene)-1,3-dihydro-indol-2-one

A mixture of 3-(5-Amino-3H-isobenzofuran-1-ylidene)-1,3-dihydro-indol-2-one (50.0 mg, 0.189 mmol), acetaldehyde (10.0 mg, 0.227 mmol), and sodium triacetoxyborohydride (52.1 mg, 0.246 mmol) was stirred at room temperature for 50.5 h. The reaction was then partitioned between EtOAc and $H_2O$. The organic phase was washed with $H_2O$, brine and then dried with $Na_2SO_4$. The solvent was removed in vacuo and the solid chromatographed ($CHCl_3$/MeOH, 97.5:2.5) to afford the title compound (14.1 mg, 25%) as a yellow solid.

$^1$H NMR (500 MHz, $CDCl_3$) δ ppm 1.31 (t, J=7.08 Hz, 3 H) 3.26 (m, 2 H) 4.25 (t, J=4.64 Hz, 1 H) 5.56 (s, 2 H) 6.53 (s, 1 H) 6.68 (dd, J=8.79, 1.95 Hz, 1 H) 6.85 (d, J=7.81 Hz, 1 H) 7.02 (td, J=7.57, 0.98 Hz, 1 H) 7.09 (td, J=7.57, 0.98 Hz, 1 H) 7.47 (s, 1 H) 7.93 (d, J=7.81 Hz, 1 H) 9.51 (d, J=8.79 Hz, 1 H).

Example 16

3-(6-Amino-3H-isobenzofuran-1-ylidene)-5-chloro-1,3-dihydro-indol-2-one

To a solution of 5-chlorooxindole (0.629 g, 3.78 mmol) in 10.0 mL monoglyme was added 7.51 mL sodium hexamethyldisilazane (1.0 M in THF) over 3 min. After stirring at room temperature for 8 min, a slurry of 6-aminophthalide (0.561 g, 3.78 mmol) in 4.0 mL of monoglyme was added in one portion. The mixture was stirred for 40 min and then quenched into 100 mL of 4% aqueous HCl solution. The yellow solid was filtered and then partitioned between EtOAc and saturated $NaHCO_3$ (heated to dissolve the solid). The organic phase was washed with $H_2O$, brine and then dried with $Na_2SO_4$. The solvent was removed in vacuo and the residue was triturated with MeOH to give the title compound (439 mg, 39%) as a yellow solid.

$^1$H NMR (500 MHz, DMSO-D6) δ ppm 5.44 (s, 2 H) 5.66 (s, 2 H) 6.81 (d, J=8.30 Hz, 1 H) 6.92 (dd, J=8.30, 1.95 Hz, 1 H) 7.12 (dd, J=8.05, 2.20 Hz, 1 H) 7.31 (d, J=8.30 Hz, 1 H) 7.79 (d, J=1.95 Hz, 1 H) 8.83 (d, J=1.95 Hz, 1 H) 10.48 (s, 1 H).

Example 17

3-(5-Amino-3H-isobenzofuran-1-ylidene)-5-chloro-1,3-dihydro-indol-2-one

To a solution of 5-chlorooxindole (0.629 g, 3.78 mmol) in 10.0 mL monoglyme was added 7.51 mL sodium hexamethyldisilazane (1.0 M in THF) over 3 min. After stirring at room temperature for 8 min, a solution of 5-aminophthalide (0.561 g, 3.78 mmol) in 3.0 mL of DMF was added over 1 min. The mixture was stirred for 40 min and then quenched into 4% aqueous HCl solution. The aqueous solution was neutralized to pH 7 with 1 M NaOH and then made basic with saturated $NaHCO_3$. The solid was filtered and washed with $H_2O$ and then partitioned between EtOAc and saturated $NaHCO_3$ (heated to dissolve the solid). The organic phase was washed with $H_2O$, brine and then dried with $Na_2SO_4$. The solvent was removed in vacuo and the residue triturated with MeOH to give the title compound (353 mg, 31%) as a yellow solid.

$^1$H NMR (500 MHz, DMSO-D6) δ ppm 5.64 (s, 2 H) 6.39 (s, 2 H) 6.68 (m, 2 H) 6.77 (d, J=8.30 Hz, 1 H) 7.03 (dd, J=8.05, 2.20 Hz, 1 H) 7.70 (d, J=1.95 Hz, 1 H) 9.31 (m, 1 H) 10.34 (s, 1 H).

Example 18

N-[1-(2-Oxo-1,2-dihydro-indol-3-ylidene)-1,3-dihydro-isobenzofuran-5-yl]-acetamide To a solution of 3-(5-Amino-3H-isobenzofuran-1-ylidene)-1,3-dihydro-indol-2-one (50.0 mg, 0.189 mmol) and N,N-diisopropylethylamine (98.8 μL, 0.567 mmol) in 2.0 mL THF was added acetyl chloride (13.4 μL, 0.189 mmol). After stirring at room temperature for 3 h, the mixture was concentrated in vacuo and the solid triturated with MeOH. Filtering the mixture and rinsing with MeOH and hexanes/EtOAc (7:3) afforded the title compound (42.2 mg, 73%) as a yellow solid.

$^1$H NMR (500 MHz, DMSO-D6) δ ppm 2.12 (s, 3 H) 5.77 (s, 2 H) 6.82 (d, J=7.32 Hz, 1 H) 6.94 (td, J=7.57, 0.98 Hz, 1 H) 7.08 (td, J=7.57, 0.98 Hz, 1 H) 7.54 (dd, J=8.79, 1.95 Hz, 1 H) 7.80 (d, J=7.32 Hz, 1 H) 8.09 (s, 1 H) 9.55 (d, J=8.79 Hz, 1 H) 10.37 (s, 1 H) 10.43 (s, 1 H).

Example 19

N-[1-(5-Chloro-2-oxo-1,2-dihydro-indol-3-ylidene)-1,3-dihydro-isobenzofuran-5-yl]-acetamide To a solution of 3-(5-Amino-3H-isobenzofuran-1-ylidene)-5-chloro-1,3-dihydro-indol-2-one (56.5 mg, 0.189 mmol) and N,N-diisopropylethylamine (98.8 μL, 0.567 mmol) in 2.5 mL THF was added acetyl chloride (13.4 μL, 0.189 mmol). After stirring at room temperature for 3 h, the mixture was concentrated in vacuo and the solid triturated with MeOH. Filtering the mixture and rinsing with MeOH and hexanes/EtOAc (7:3) afforded the title compound (55.9 mg, 87%) as a yellow solid.

$^1$H NMR (500 MHz, DMSO-D6) δ ppm 2.12 (s, 3 H) 5.82 (s, 2 H) 6.82 (d, J=7.81 Hz, 1 H) 7.12 (dd, J=8.30, 2.44 Hz, 1 H) 7.56 (dd, J=8.54, 1.71 Hz, 1 H) 7.76 (d, J=2.44 Hz, 1 H) 8.10 (s, 1 H) 9.52 (d, J=8.79 Hz, 1 H) 10.46 (s, 1 H) 10.52 (s, 1 H).

Example 20

N-[3-(5-Chloro-2-oxo-1,2-dihydro-indol-3-ylidene)-1,3-dihydro-isobenzofuran-5-yl]-acetamide To a solution of 3-(6-Amino-3H-isobenzofuran-1-ylidene)-5-chloro-1,3-dihydro-indol-2-one (56.5 mg, 0.189 mmol) and N,N-diisopropylethylamine (98.8 μL, 0.567 mmol) in 2.5 mL THF was added acetyl chloride (13.4 μL, 0.189 mmol). After stirring at room temperature for 3 h, the mixture was filtered and rinsed with isopropanol and hexanes/EtOAc (7:3) to give the title compound (46.9 mg, 73%) as a yellow solid.

$^1$H NMR (500 MHz, DMSO-D6) δ ppm 2.09 (s, 3 H) 5.79 (s, 2 H) 6.83 (d, J=8.30 Hz, 1 H) 7.15 (dd, J=8.30, 1.95 Hz, 1 H) 7.60 (d, J=8.30 Hz, 1 H) 7.80 (d, J=1.95 Hz, 1 H) 8.11 (dd, J=8.30, 1.95 Hz, 1 H) 9.58 (d, J=1.95 Hz, 1 H) 10.29 (s, 1 H) 10.55 (s, 1 H).

Example 21 and Example 22

3-(6-Dimethylamino-3H-isobenzofuran-1-ylidene)-1,3-dihydro-indol-2-one and 3-(6-Methylamino-3H-isobenzofuran-1-ylidene)-1,3-dihydro-indol-2-one To a solution of 3-(6-Amino-3H-isobenzofuran-1-ylidene)-1,3-dihydro-indol-2-one (50.0 mg, 0.189 mmol) and N,N-diisopropylethylamine (65.8 μL, 0.378 mmol) in 2.0 mL THF was added iodomethane (12.9 μL, 0.208 mmol). After stirring at room temperature for 21 h, silver triflate (53.4 mg, 0.208 mmol) was added and the mixture heated at 45° C. for 16 h. The mixture was partitioned between EtOAc and saturated $NaHCO_3$ and the organic separated. The organic layer was washed with $H_2O$, brine and then dried with $Na_2SO_4$. The solution was evaporated in vacuo and the residue purified by chromatography (silica gel, 2% MeOH/$CHCl_3$) to give 3-(6-Dimethylamino-3H-isobenzofuran-1-ylidene)-1,3-dihydro-indol-2-one (3.6 mg) as a yellow solid.

$^1$H NMR (500 MHz, $CDCl_3$) δ ppm 3.08 (s, 6 H) 5.62 (s, 2 H) 6.86 (d, J=7.81 Hz, 1 H) 6.97 (dd, J=8.30, 2.44 Hz, 1 H) 7.05 (td, J=7.57, 0.98 Hz, 1 H) 7.14 (td, J=7.57, 1.46 Hz, 1 H) 7.30 (d, J=8.30 Hz, 1 H) 7.62 (s, 1 H) 8.00 (d, J=6.83 Hz, 1 H) 9.31 (d, J=2.44 Hz, 1 H) and 3-(6-Methylamino-3H-isobenzofuran-1-ylidene)-1,3-dihydro-indol-2-one (6.3 mg) as a yellow solid.

$^1$H NMR (500 MHz, $CDCl_3$) δ ppm 2.96 (s, 3 H) 4.02 (s, 1 H) 5.60 (s, 2 H) 6.84 (m, 2 H) 7.05 (td, J=7.57, 0.98 Hz, 1 H) 7.14 (td, J=7.57, 1.46 Hz, 1 H) 7.24 (obsc d, 1 H) 7.52 (s, 1 H) 7.99 (d, J=7.81 Hz, 1 H) 9.10 (d, J=2.44 Hz, 1 H).

Example 23 and Example 24

3-(5-Dimethylamino-3H-isobenzofuran-1-ylidene)-1,3-dihydro-indol-2-one and 3-(5-Methylamino-3H-isobenzofuran-1-ylidene)-1,3-dihydro-indol-2-one To a solution of 3-(5-Amino-3H-isobenzofuran-1-ylidene)-1,3-dihydro-indol-2-one (50.0 mg, 0.189 mmol) and N,N-diisopropylethylamine (65.8 μL, 0.378 mmol) in 2.0 mL THF was added iodomethane (12.9 μL, 0.208 mmol). After stirring at room temperature for 21 h, silver triflate (53.4 mg, 0.208 mmol) was added and the mixture heated at 45° C. for 16 h. The mixture was partitioned between EtOAc and saturated $NaHCO_3$ and the organic separated. The organic layer was washed with $H_2O$, brine and then dried with $Na_2SO_4$. The solution was evaporated in vacuo and chromatographed with 2% MeOH/$CHCl_3$ to give 3-(5-Dimethylamino-3H-isobenzofuran-1-ylidene)-1,3-dihydro-indol-2-one (1.2 mg) as a yellow-orange solid and 3-(5-Methylamino-3H-isobenzofuran-1-ylidene)-1,3-dihydro-indol-2-one (8.9 mg) as an orange solid.

Example 23

$^1$H NMR (500 MHz, $CDCl_3$) δ ppm 3.10 (s, 6 H) 5.59 (s, 2 H) 6.62 (d, J=2.44 Hz, 1 H) 6.81 (dd, J=8.79, 2.44 Hz, 1 H) 6.85 (d, J=7.32 Hz, 1 H) 7.02 (td, J=7.57, 1.46 Hz, 1 H) 7.09 (td, J=7.57, 0.98 Hz, 1 H) 7.47 (s, 1 H) 7.93 (d, J=7.32 Hz, 1 H) 9.54 (d, J=9.28 Hz, 1 H);

Example 24

$^1$H NMR (500 MHz, DMSO-$d_6$) δ ppm 2.79 (s, 3 H) 5.63 (s, 2 H) 6.65 (s, 1 H) 6.69 (dd, J=9.03, 2.20 Hz, 1 H) 6.78 (d, J=7.81 Hz, 1 H) 6.85 (br, 1 H) 6.89 (t, J=7.08 Hz, 1 H) 7.01 (m, 1 H) 7.75 (d, J=7.81 Hz, 1 H) 9.38 (d, J=8.79 Hz, 1 H) 10.20 (s, 1 H) LR MS (EI): 278 ($M^+$)

Example 26

4-Chloro-N-[3-(2-oxo-1,2-dihydro-indol-3-ylidene)-1,3-dihydro-isobenzofuran-5-yl]-butyramide To a solution of 3-(6-Amino-3H-isobenzofuran-1-ylidene)-1,3-dihydro-indol-2-one (50.0 mg, 0.189 mmol) and N,N-diisopropylethylamine (98.8 μL, 0.567 mmol) in 2.0 mL THF was added 4-chlorobutyryl chloride (21.2 μL, 0.189 mmol). After stirring at room temperature for 1 h, the slurry was filtered and rinsed with MeOH and EtOAc/hexanes (1:1) to afford the title compound (58.8 mg, 84%) as a yellow solid.

$^1$H NMR (500 MHz, DMSO-D6) δ ppm 2.06 (m, 2 H) 2.54 (t, J=7.32 Hz, 2 H) 3.72 (t, J=6.35 Hz, 2 H) 5.75 (s, 2 H) 6.83 (d, J=7.32 Hz, 1 H) 6.96 (m, 1 H) 7.12 (td, J=7.69, 1.22 Hz, 1 H) 7.58 (d, J=8.30 Hz, 1 H) 7.83 (d, J=7.32 Hz, 1 H) 8.10 (dd, J=8.30, 1.46 Hz, 1 H) 9.63 (d, J=1.95 Hz, 1 H) 10.34 (s, 1 H) 10.40 (s, 1 H)

Example 11 and Example 27

3-(6-Ethylamino-3H-isobenzofuran-1-ylidene)-1,3-dihydro-indol-2-one and 3-(6-Diethylamino-3H-isobenzofuran-1-ylidene)-1,3-dihydro-indol-2-one A mixture of 3-(6-Amino-3H-isobenzofuran-1-ylidene)-1,3-dihydro-indol-2-one (581 mg, 2.20 mmol), acetaldehyde (116 mg, 2.64 mmol), and sodium triacetoxyborohydride (606 mg, 2.86 mmol) was stirred at room temperature for 3 h. The reaction was then partitioned between ethyl acetate and $H_2O$. The organic phase was washed with dilute aqueous $NaHCO_3$ solution, $H_2O$, brine and then dried with $Na_2SO_4$. The solvent was removed in vacuo and the residue was dissolved in $CHCl_3$/MeOH and purified by chromatography (silica gel, hexanes/EtOAc, 7:3) to give 3-(6-Ethylamino-3H-isobenzofuran-1-ylidene)-1,3-dihydro-indol-2-one (395.1 mg, 61%) as a yellow solid and 3-(6-Diethylamino-3H-isobenzofuran-1-ylidene)-1,3-dihydro-indol-2-one (32.9 mg, 5%) as a yellow solid.

Example 27

$^1$H NMR (500 MHz, DMSO-D6) δ ppm 1.15 (t, J=7.08 Hz, 6 H) 3.42 (q, J=7.16 Hz, 4 H) 5.66 (s, 2 H) 6.84 (d, J=7.81 Hz, 1 H) 6.95 (t, J=7.57 Hz, 1 H) 7.00 (dd, J=8.54, 2.20 Hz, 1 H) 7.10 (t, J=7.57 Hz, 1 H) 7.40 (d, J=8.30 Hz, 1 H) 7.83 (d, J=7.81 Hz, 1 H) 9.22 (d, J=2.44 Hz, 1 H) 10.28 (s, 1 H).

The compounds of Tables 3, 4 and 5 are prepared by procedures analogous to the procedures used to prepare the compounds of Examples 1 through 27 and as specifically set forth in Examples 28 through 134. These compounds, like the compounds of Examples 1 through 27, show activity as VEGF inhibitors.

TABLE 3

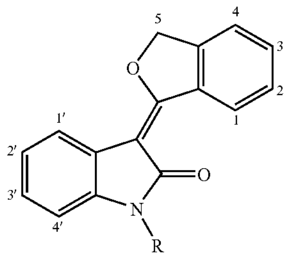

| Example Number | 1 | 2 | 3 | 4 | 5 | 1' | 2' | 3' | 4' | R |
|---|---|---|---|---|---|---|---|---|---|---|
| 28 | H | H | H | H | H, H | H | OMe | H | H | H |
| 29 | H | 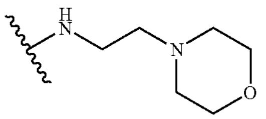 | H | H | H, H | H | H | H | H | H |
| 30 | H | $NHCOCH_2Br$ | H | H | H, H | H | Cl | H | H | H |
| 31 | H | 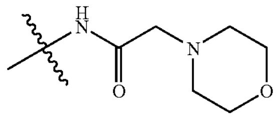 | H | H | H, H | H | Cl | H | H | H |
| 32 | H | 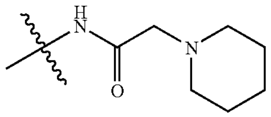 | H | H | H, H | H | Cl | H | H | H |
| 33 | H | 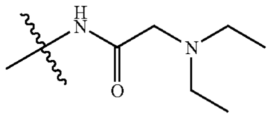 | H | H | H, H | H | Cl | H | H | H |
| 34 | H | 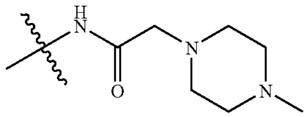 | H | H | H, H | H | Cl | H | H | H |
| 35 | H | $NHCO_2C(CH_3)_3$ | H | H | H, H | H | H | H | H | H |
| 36 | H | $NHCO_2C(CH_3)_3$ | H | H | H, H | H | Cl | H | H | H |
| 37 | H | 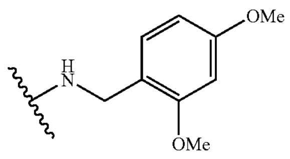 | H | H | H, H | H | H | H | H | H |

TABLE 3-continued
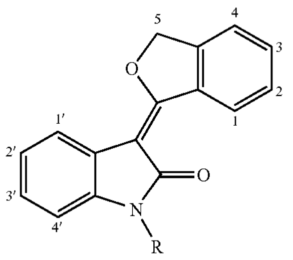
| Example Number | 1 | 2 | 3 | 4 | 5 | 1' | 2' | 3' | 4' | R |
|---|---|---|---|---|---|---|---|---|---|---|
| 38 | H | 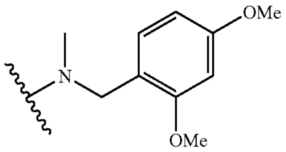 | H | H | H, H | H | H | H | H | —$CH_2OH$ |
| 39 | H | $NHCH_3$ | H | H | H, H | H | H | H | H | —$CH_2OH$ |
| 40 | H | $NMe_2$ | H | H | H, H | H | H | H | H | —$CH_2OH$ |
| 41 | H | $NHSO_2CH_3$ | H | H | H, H | H | Cl | H | H | H |
| 42 | H | $NHCOCH{=}CH_2$ | H | H | H, H | H | Cl | H | H | H |
TABLE 4
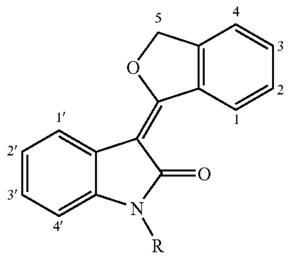
| Example Number | 1 | 2 | 3 | 4 | 5 | 1' | 2' | 3' | 4' | R |
|---|---|---|---|---|---|---|---|---|---|---|
| 43 | H | H | $NH_2$ | H | H, H | H | H | F | H | H |
| 44 | H | H | $NH_2$ | H | H, H | H | F | H | H | H |
| 45 | H | H | $NH(CH_2)_2Cl$ | H | H, H | H | H | H | H | H |
| 46 | H | H | $NH(CH_2)_2Cl$ | H | H, H | H | H | F | H | H |
| 47 | H | H | $NH(CH_2)_2Cl$ | H | H, H | H | F | H | H | H |
| 48 | H | H | 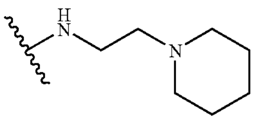 | H | H, H | H | H | H | H | H |
| 49 | H | H | 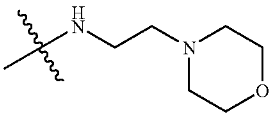 | H | H, H | H | H | H | H | H |
| 50 | H | H | 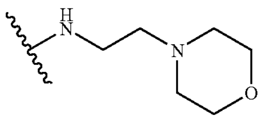 | H | H, H | H | H | F | H | H |

TABLE 4-continued
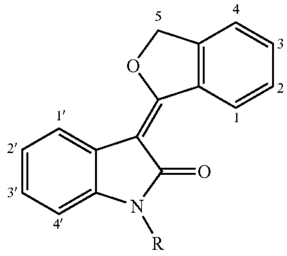
| Example Number | 1 | 2 | 3 | 4 | 5 | 1' | 2' | 3' | 4' | R |
|---|---|---|---|---|---|---|---|---|---|---|
| 51 | H | H | 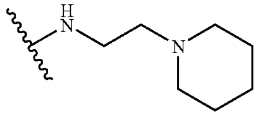 | H | H, H | H | H | F | H | H |
| 52 | H | H | 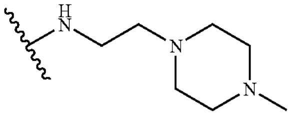 | H | H, H | H | H | H | H | H |
| 53 | H | H | 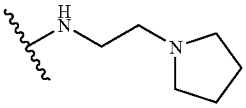 | H | H, H | H | H | H | H | H |
| 54 | H | H | 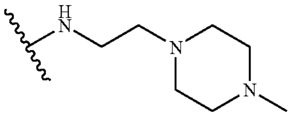 | H | H, H | H | H | F | H | H |
| 55 | H | H | 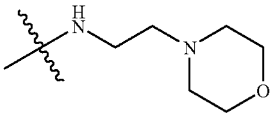 | H | H, H | H | F | H | H | H |
| 56 | H | H | 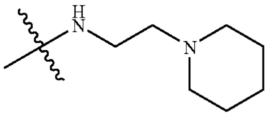 | H | H, H | H | F | H | H | H |
| 57 | H | H | 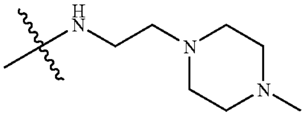 | H | H, H | H | F | H | H | H |
| 58 | H | H | 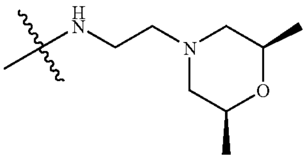 | H | H, H | H | H | H | H | H |
| 59 | H | H | 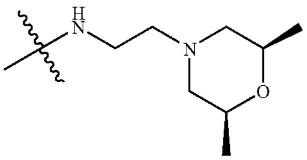 | H | H, H | H | F | H | H | H |

TABLE 4-continued
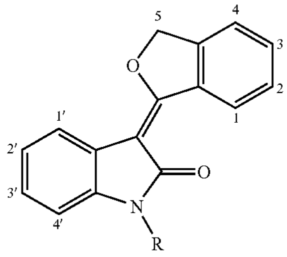
| Example Number | 1 | 2 | 3 | 4 | 5 | 1' | 2' | 3' | 4' | R |
|---|---|---|---|---|---|---|---|---|---|---|
| 60 | H | H | 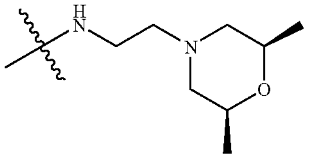 | H | H, H | H | H | F | H | H |
| 61 | H | H | 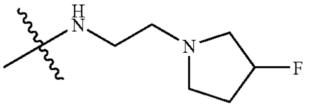 | H | H, H | H | H | H | H | H |
| 62 | H | H | 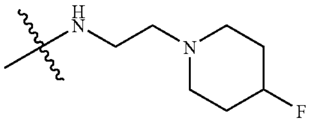 | H | H, H | H | H | H | H | H |
| 63 | H | H | 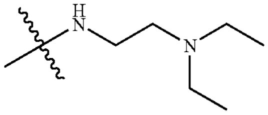 | H | H, H | H | F | H | H | H |
| 64 | H | H | 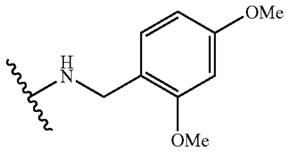 | H | H, H | H | H | H | H | H |
| 65 | H | H | 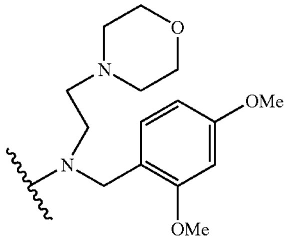 | H | H, H | H | H | H | H | H |
| 66 | H | H | 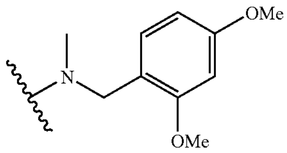 | H | H, H | H | H | F | H | H |

TABLE 4-continued
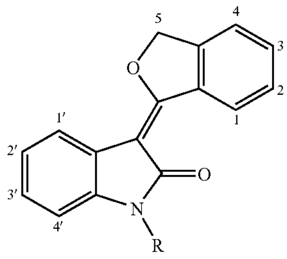
| Example Number | 1 | 2 | 3 | 4 | 5 | 1' | 2' | 3' | 4' | R |
|---|---|---|---|---|---|---|---|---|---|---|
| 67 | H | H | 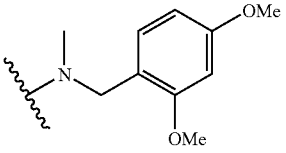 | H | H, H | H | H | H | H | H |
| 68 | H | H | 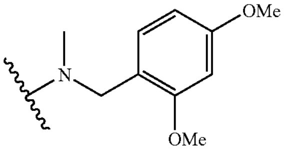 | H | H, H | H | Cl | H | H | H |
| 69 | H | H | 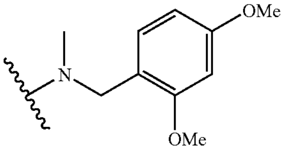 | H | H, H | H | H | H | F | H |
| 70 | H | H | 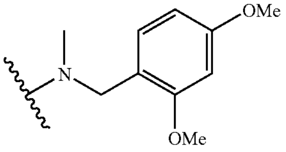 | H | H, H | H | F | H | H | H |
| 71 | H | H | 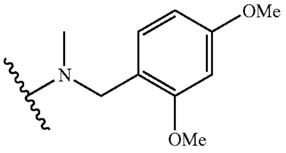 | H | H, H | H | H | Cl | H | H |
| 72 | H | H | $NHCH_3$ | H | H, H | H | H | F | H | H |
| 73 | H | H | $NHCH_3$ | H | H, H | H | F | H | H | H |
| 74 | H | H | $NHCH_3$ | H | H, H | H | Cl | H | H | H |
| 75 | H | H | $NHCH_3$ | H | H, H | H | H | Cl | H | H |
| 76 | H | H | $NHCH_3$ | H | H, H | H | H | H | F | H |
| 77 | H | H | $N(CH_3)_2$ | H | H, H | H | Cl | H | H | H |
| 78 | H | H | $NHC(C_6H_5)_3$ | H | H, H | H | Cl | H | H | H |
| 79 | H | H | $N(CH_2C_6H_5)_2$ | H | H, H | H | Cl | H | H | H |
| 80 | H | H | 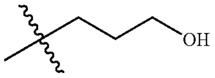 | H | H, H | H | H | H | H | H |
| 81 | H | H | 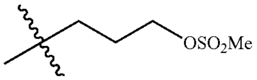 | H | H, H | H | H | H | H | H |

TABLE 4-continued
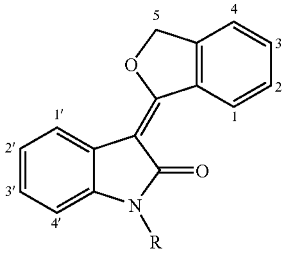
| Example Number | 1 | 2 | 3 | 4 | 5 | 1' | 2' | 3' | 4' | R |
|---|---|---|---|---|---|---|---|---|---|---|
| 82 | H | H | 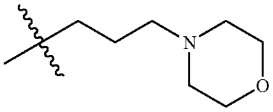 | H | H, H | H | H | H | H | H |
| 83 | H | H | 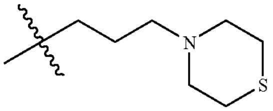 | H | H, H | H | H | H | H | H |
| 84 | H | H | 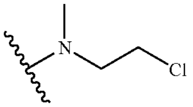 | H | H, H | H | H | H | H | H |
| 85 | H | H | 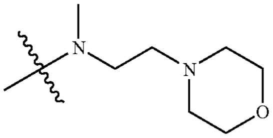 | H | H, H | H | H | H | H | H |
| 86 | H | H | 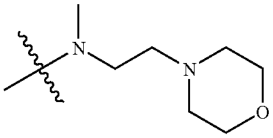 | H | H, H | H | F | H | H | H |
| 87 | H | H | 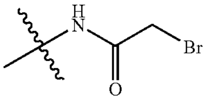 | H | H, H | H | Cl | H | H | H |
| 88 | H | H | 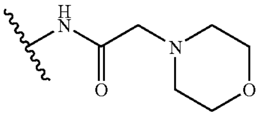 | H | H, H | H | Cl | H | H | H |
| 89 | H | H | 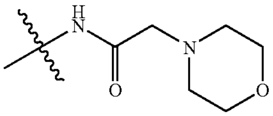 | H | H, H | H | H | H | H | H |
| 90 | H | H | 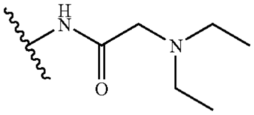 | H | H, H | H | Cl | H | H | H |

TABLE 4-continued
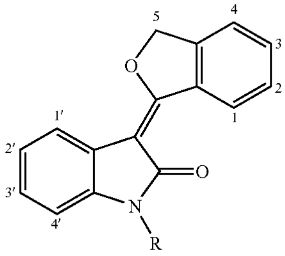
| Example Number | 1 | 2 | 3 | 4 | 5 | 1' | 2' | 3' | 4' | R |
|---|---|---|---|---|---|---|---|---|---|---|
| 91 | H | H | 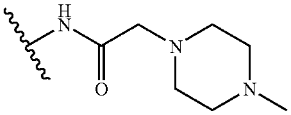 | H | H, H | H | Cl | H | H | H |
| 92 | H | H | 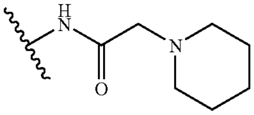 | H | H, H | H | Cl | H | H | H |
| 93 | H | H | $NH(CH_2)_2OH$ | H | H, H | H | H | H | H | H |
| 94 | H | H | $NH(CH_2)_2OH$ | H | H, H | H | H | F | H | H |
| 95 | H | H | $NH(CH_2)_2OCOCH_3$ | H | H, H | H | H | H | H | H |
| 96 | H | H | $NH(CH_2)_2OCOCH_3$ | H | H, H | H | H | F | H | H |
| 97 | H | H | 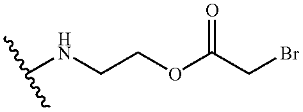 | H | H, H | H | H | H | H | H |
| 98 | H | H | 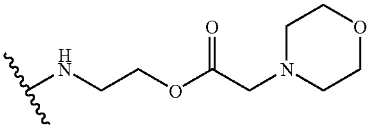 | H | H, H | H | H | H | H | H |
| 99 | H | H | 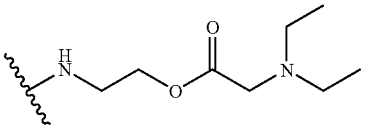 | H | H, H | H | H | H | H | H |
| 100 | H | H | 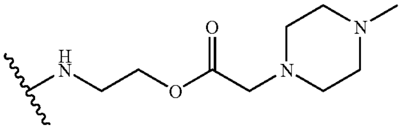 | H | H, H | H | H | H | H | H |
| 101 | H | H | 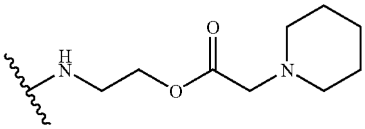 | H | H, H | H | H | H | H | H |
| 102 | H | H | Br | H | H, H | H | H | H | H | H |
| 103 | H | H | 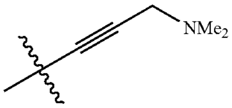 | H | H, H | H | H | H | H | H |

TABLE 4-continued
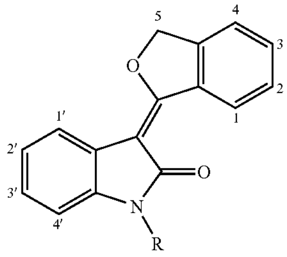
| Example Number | 1 | 2 | 3 | 4 | 5 | 1' | 2' | 3' | 4' | R |
|---|---|---|---|---|---|---|---|---|---|---|
| 104 | H | H | 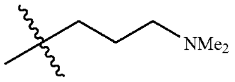 | H | H, H | H | H | H | H | H |
| 135 | H | H | 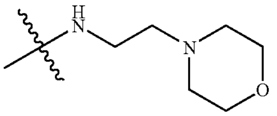 | H | H, H | H | Cl | H | H | H |
TABLE 5
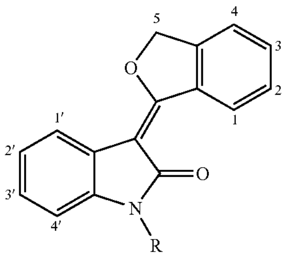
| Example Number | 1 | 2 | 3 | 4 | 5 | 1' | 2' | 3' | 4' | R |
|---|---|---|---|---|---|---|---|---|---|---|
| 105 | H | H | H | H | $-(CH_2)_2NH(CH_2)_2-$ | H | H | H | H | H |
| 106 | H | H | H | H | $-CH_2COOH$ | H | H | H | H | H |
| 107 | H | H | H | H | $-CH_2COOH$ | H | Cl | H | H | H |
| 108 | H | H | H | H | $-CH_2COOH$ | H | H | F | H | H |
| 109 | H | H | H | H | $-CH_2CH_2OH$ | H | H | H | H | H |
| 110 | H | H | H | H | $-(CH_2)_2OSO_2CH_3$ | H | H | H | H | H |
| 111 | H | H | H | H | 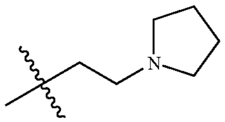 | H | H | H | H | H |
| 112 | H | H | H | H | 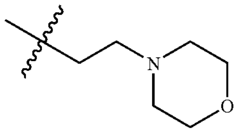 | H | H | H | H | H |
| 113 | H | H | H | H | 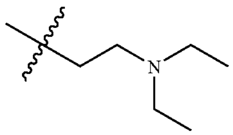 | H | H | H | H | H |

TABLE 5-continued
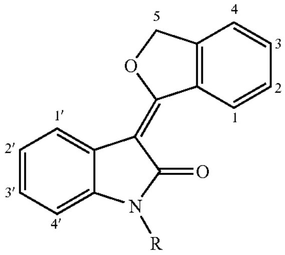
| Example Number | 1 | 2 | 3 | 4 | 5 | 1' | 2' | 3' | 4' | R |
|---|---|---|---|---|---|---|---|---|---|---|
| 114 | H | H | H | H | 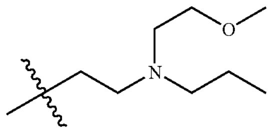 | H | H | H | H | H |
| 115 | H | H | H | H | 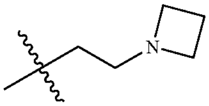 | H | H | H | H | H |
| 116 | H | H | H | H | $—CH_2N(CH_3)_2$ | H | H | H | H | H |
| 117 | H | H | H | H | $—CH_2NCO$ | H | H | H | H | H |
| 118 | H | H | H | H | $—CH_2NHCONH_2$ | H | H | H | H | H |
| 119 | H | H | H | H | $—CH_2NHCO_2C_2H_5$ | H | H | H | H | H |
| 120 | H | H | H | H | 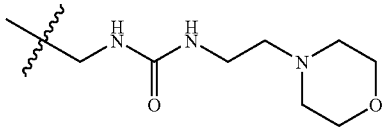 | H | H | H | H | H |
| 121 | H | H | H | H | 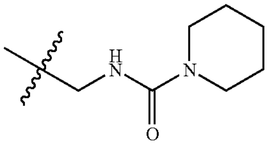 | H | H | H | H | H |
| 122 | H | H | H | H | 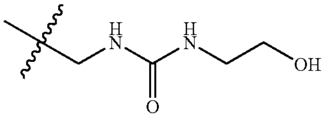 | H | H | H | H | H |
| 123 | H | H | H | H | 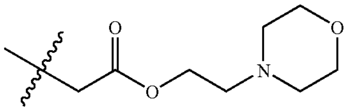 | H | H | H | H | H |
| 124 | H | H | H | H | 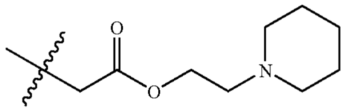 | H | H | F | H | H |
| 125 | H | H | H | H | $—CH_2CO_2CH_3$ | H | H | F | H | H |
| 126 | H | H | H | H | —COOH | H | H | H | H | H |
| 127 | H | H | H | H | 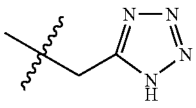 | H | H | H | H | H |
| 128 | H | H | H | H | $—CH_2CONH_2$ | H | H | H | H | H |
| 129 | H | H | H | H | Me | H | H | H | H | H |

TABLE 5-continued
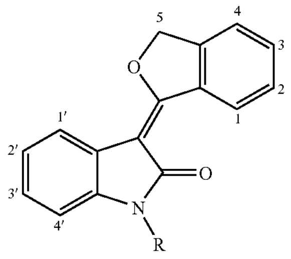
| Example Number | 1 | 2 | 3 | 4 | 5 | 1' | 2' | 3' | 4' | R |
|---|---|---|---|---|---|---|---|---|---|---|
| 130 | H | H | H | H | 2*x*Me | H | H | H | H | H |
| 131 | H | H | OMe | H | —$CH_2COOH$ | H | H | H | H | H |
| 132 | H | OMe | H | H | —$CH_2COOH$ | H | H | H | H | H |
| 133 | H | H | H | H | —$CH_2COONa$ | H | H | H | H | H |
| 134 | H | H | H | H | —$CH_2COONa$ | H | H | F | H | H |
TABLE 6
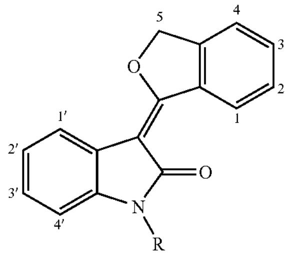
| Example Number | 1 | 2 | 3 | 4 | 5 | 1' | 2' | 3'4' | R | |
|---|---|---|---|---|---|---|---|---|---|---|
| 136 | H | H | 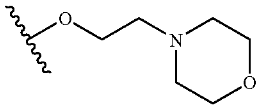 | H | H, H | H | OMe | F | H | H |
| 137 | H | H | 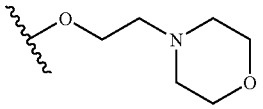 | H | H, H | H | F | H | H | H |
| 138 | H | H | 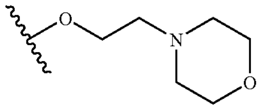 | H | H, H | H | Cl | H | H | H |
| 139 | H | H | 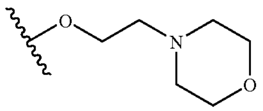 | H | H, H | H | 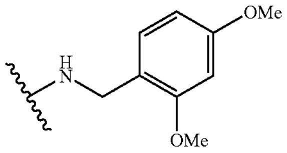 | F | H | H |

Example 28

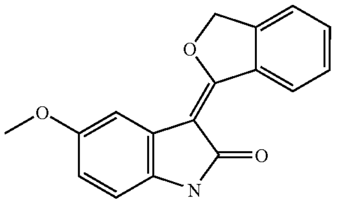

3-(3H-Isobenzofuran-1-ylidene)-5-methoxy-1,3-dihydro-indol-2-one

To a stirred solution of 5-methoxyoxindole (100 mg, 0.61 mmol) in anhydrous THF (5 ml) under nitrogen was added 1.0M LiHMDS/THF solution (1.3 ml, 1.3 mmol). The mixture was stirred at room temperature for 10 minutes, and phthalide (74 mg, 0.55 mmol) was added. The mixture was stirred at room temperature for 5 hours and was then poured into a mixture of THF (10 ml) and 2M HCl (10 ml). The mixture was heated at 45° C. for 30 minutes, cooled to room temperature, and poured into water (125 ml). The resulting solid was separated, washed with water and dried under vacuum to give 3-(3H-Isobenzofuran-1-ylidene)-5-methoxy-1,3-dihydro-indol-2-one (70 mg, 46%).

$^1$H NMR (500 MHz, DMSO-$d_6$) δ ppm 3.69 (s, 3 H) 5.76 (s, 2 H) 6.67 (m, 2 H) 7.41 (s, 1 H) 7.51 (m, 1 H) 7.61 (m, 2 H) 9.62 (d, J=8.30 Hz, 1 H) 10.19 (s, 1 H)

Preparation 1

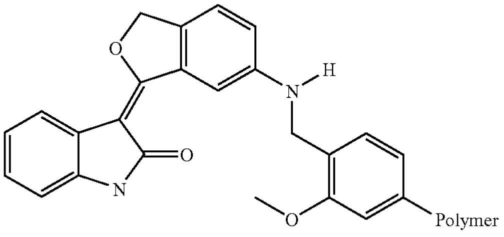

3-[6-(2-Morpholin-4-yl-ethylamino)-3-isobenzofuran-1-ylidene]-1,3-dihydro-indol-2-one-6-bonding to 4-formyl-3-methoxyphenoxymethyl resin To a mixture of 3-(6-amino-3H-isobenzofuran-1-ylidene)-1,3-dihydro-indol-2-one (0.5 g, 1.89 mmol), 4-formyl-3-methoxyphenoxymethyl resin (1.1 g, 1.26 mmole) in 1% AcOH/DMF (21 ml) was added sodium triacetoxyborohydride (2.7 g, 12.6 mmol). The resulting mixture was gently stirred at room temperature for 48 hours. The resin was separated, and washed with DMF, MeOH, and $CHCl_3$, alternately. Removal of the solvent provided 3-[6-(2-morpholin-4-yl-ethylamino)-3-isobenzofuran-1-ylidene]-1,3-dihydro-indol-2-one-6-bound to 4-formyl-3-methoxyphenoxymethyl resin (1.1 g).

Preparation 2

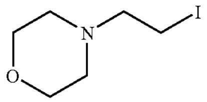

Preparation of 4-(2-Iodo-ethyl)-morpholine

A mixture of 4-(2-chloro-ethyl)-morpholine hydrochloride (5 g, 26.9 mmole), and sodium iodide (20 g, 134.4 mmole) in acetone (50 ml) was refluxed for 16 hours. After cooled to room temperature, the reaction was partitioned between $CHCl_3$ and brine. The aqueous layer was extracted with $CHCl_3$ (2×25 ml). The combined organic layers were washed with brine, and dried over anhydrous $Mg_2SO4$. Removal of the solvent gave 4-(2-iodo-ethyl)-morpholine as a pale yellowish oil (3.84 g, 59%).

$^1$H NMR (500 MHz, $CDCl_3$) δ ppm 2.51 (brs, 4 H) 2.74 (t, J=7.81 Hz, 2 H) 3.22 (t, J=7.81 Hz, 2 H) 3.73 (t, J=4.39 Hz, 4 H)

Example 29

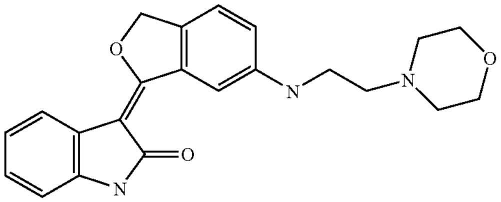

3-[6-(2-Morpholin-4-yl-ethylamino)-3-isobenzofuran-1-ylidene]-1,3-dihydro-indol-2-one A mixture of 3-[6-(2-morpholin-4-yl-ethylamino)-3-isobenzofuran-1-ylidene]-1,3-dihydro-indol-2-one-6-bonding to 4-formyl-3-methoxyphenoxymethyl resin (200 mg, 0.182 mmol), 4-(2-iodo-ethyl)-morpholine (660 mg, 2.72 mmol), N,N-diisopropylethylamine (0.94 ml, 5.44 mmol) in 1,4-dioxane was heated at 106° C. under nitrogen for 16 hours. The resulting resin was separated, and washed with DMF, MeOH, and $CHCl_3$, alternately. The washed resin was then mixed with 10% trifluoroacetic acid in $CH_2Cl_2$ (5 ml), and stirred at room temperature for 1 hour. The resulting mixture was poured into a mixture of $CHCl_3$, and saturated aqueous $NaHCO_3$ solution. The aqueous layer was extracted with $CHCl_3$. The combined organic layers were washed with brine, dried over anhydrous $MgSO_4$. Purification of the mixture by preparative silica gel TLC, eluted with 9:1 $CHCl_3$/MeOH, led to 3-[6-(2-Morpholin-4-yl-ethylamino)-3-isobenzofuran-1-ylidene]-1,3-dihydro-indol-2-one as a yellow solid (32 mg, 14%).

$^1$H NMR (500 MHz, $CDCl_3$) δ ppm 2.44 (br s, 4 H) 2.62 (t, J=5.61 Hz, 2 H) 3.25 (t, J=5.86 Hz, 2 H) 3.68 (t, J=4.64 Hz, 4 H) 5.53 (s, 2 H) 6.80 (m, 2 H) 6.98 (td, J=7.69, 1.22 Hz, 1 H) 7.08 (td, J=7.57, 1.46 Hz, 1 H) 7.18 (d, J=8.30 Hz, 1 H) 7.47 (s, 1 H) 7.92 (d, J=7.81 Hz, 1 H) 9.03 (d, J=2.44 Hz, 1 H)

Example 30

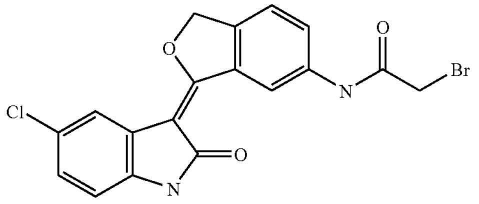

2-Bromo-N-[3-(5-chloro-2-oxo-1,2-dihydro-indol-3-ylidene)-1,3-dihydro-isobenzofuran-5-yl]-acetamide To a stirred suspension of 3-(6-amino-3H-isobenzofuran-1-ylidene)-5-chloro-1,3-dihydro-indol-2-one (300 mg, 1.0 mmol) in THF (15 ml), was added bromoacetic anhydride (311 mg, 1.2 mmol). The mixture was stirred for 1 hour and was poured into water (150 ml). The solid was filtered, washed with water and dried under vacuum to give 2-bromo-N-[3-(5-chloro-2-oxo-1,2-dihydro-indol-3-ylidene)-1,3-dihydro-isobenzofuran-5-yl]-acetamide as a yellow solid (396 mg, 94%).

$^1$H NMR (500 MHz, DMSO-$d_6$) δ ppm 4.10 (s, 2 H) 5.81 (s, 2 H) 6.84 (d, J=8.30 Hz, 1 H) 7.16 (dd, J=8.06, 2.20 Hz, 1 H) 7.65 (d, J=8.30 Hz, 1 H) 7.81 (d, J=1.95 Hz, 1 H) 8.14 (d, J=8.30 Hz, 1 H) 9.64 (s, 1 H) 10.57 (s, 1 H) 10.75 (s, 1 H).

Example 31

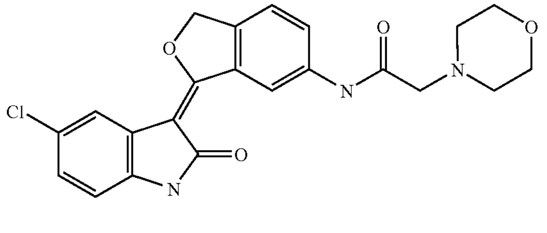

N-[3-(5-Chloro-2-oxo-1,2-dihydro-indol-3-ylidene)-1,3-dihydro-isobenzofuran-5-yl]-2-morpholin-4-yl-acetamide A mixture of 2-bromo-N-[3-(5-chloro-2-oxo-1,2-dihydro-indol-3-ylidene)-1,3-dihydro-isobenzofuran-5-yl]-acetamide (63 mg, 0.15 mmol) in morpholine (1 ml) was stirred at 40° C. under nitrogen for 40 minutes. The mixture was poured into water (75 ml). The solid was filtered, washed with water and dried under vacuum to give N-[3-(5-chloro-2-oxo-1,2-dihydro-indol-3-ylidene)-1,3-dihydro-isobenzofuran-5-yl]-2-morpholin-4-yl-acetamide as a yellow solid (60 mg, 94%).

$^1$H NMR (300 MHz, DMSO-$d_6$) δ ppm 2.55 (m, 4 H) 3.19 (s, 2 H) 3.65 (m, 4 H) 5.81 (s, 2 H) 6.84 (d, J=8.21 Hz, 1 H) 7.16 (dd, J=8.21, 2.35 Hz, 1 H) 7.62 (d, J=8.21 Hz, 1 H) 7.81 (d, J=2.05 Hz, 1 H) 8.06 (dd, J=8.21, 1.76 Hz, 1 H) 9.66 (d, J=1.76 Hz, 1 H) 10.07 (s, 1 H) 10.53 (s, 1 H).

The following Example 32 through 34 were prepared using the experiment procedure described in Example 31, but with the appropriate reagent, reaction conditions and reactant substitutions that will be readily realized by those of ordinary skill in this art without the exercise of undue experimentation Example 32

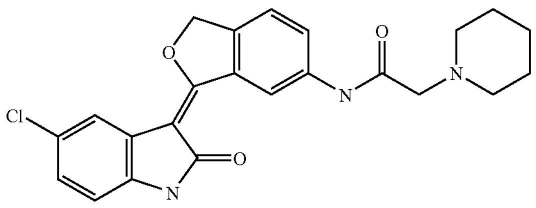

N-[3-(5-Chloro-2-oxo-1,2-dihydro-indol-3-ylidene)-1,3-dihydro-isobenzofuran-5-yl]-2-piperidin-1-yl-acetamide $^1$H NMR (300 MHz, DMSO-$d_6$) δ ppm 1.41 (brs, 2H) 1.58 (m, 4 H) 2.47(brs, 4 H) 3.12 (s, 2 H) 5.81 (s, 2 H) 6.84 (d, J=8.21 Hz, 1 H) 7.16 (dd, J=8.21, 2.35 Hz, 1 H) 7.62 (d, J=8.21 Hz, 1 H) 7.81 (d, J=2.05 Hz, 1 H) 8.08 (dd, J=8.21, 1.76 Hz, 1 H) 9.65 (d, J=1.76 Hz, 1 H) 9.96 (s, 1 H).

Example 33

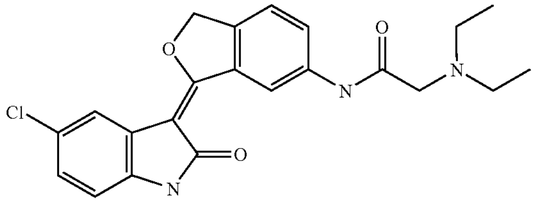

N-[3-(5-Chloro-2-oxo-1,2-dihydro-indol-3-ylidene)-1,3-dihydro-isobenzofuran-5-yl]-2-diethylamino-acetamide $^1$H NMR (300 MHz, DMSO-$d_6$) δ ppm 1.03 (t, J=7.04 Hz, 6 H) 2.62 (q, J=7.23 Hz, 4 H) 3.19 (s, 2 H) 5.79 (s, 2 H) 6.82 (d, J=8.21 Hz, 1 H) 7.14 (dd, J=8.36, 2.20 Hz, 1 H) 7.61 (d, J=8.21 Hz, 1 H) 7.79 (d, J=2.05 Hz, 1 H) 8.06 (dd, J=8.35, 1.61 Hz, 1 H) 9.63 (d, J=1.47 Hz, 1 H) 9.88 (s, 1 H) 10.50 (s, 1 H)

Example 34

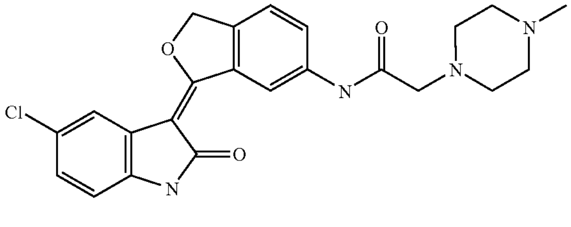

N-[3-(5-Chloro-2-oxo-1,2-dihydro-indol-3-ylidene)-1,3-dihydro-isobenzofuran-5-yl]-2-(4-methyl-piperazin-1-yl)-acetamide $^1$H NMR (300 MHz, DMSO-$d_6$) δ ppm 2.18 (s, 3 H) 2.39 (brs, 4 H) 2.55 (brs, 4 H) 3.16 (s, 2 H) 5.80 (s, 2 H) 6.84 (d, J=8.21 Hz, 1 H) 7.16 (dd, J=8.21, 2.05 Hz, 1 H) 7.62 (d, J=8.21 Hz, 1 H) 7.80 (d, J=2.05 Hz, 1 H) 8.08 (dd, J=8.50, 1.76 Hz, 1 H) 9.64 (d, J=1.76 Hz, 1 H) 9.99 (s, 1 H) 10.54 (s, 1 H).

Example 35

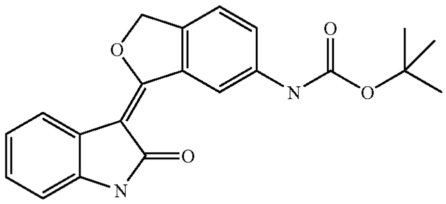

[3-(2-Oxo-1,2-dihydro-indol-3-ylidene)-1,3-dihydro-isobenzofuran-5-yl]-carbamic acid t-butyl ester To a stirred suspension of 3-(6-amino-3H-isobenzofuran-1-ylidene)-1,3-dihydro-indol-2-one (500 mg, 1.89 mmol) and triethylamine (574 mg, 5.67 mmol) in MeOH (30 ml), was added 1M di-tert-butyl dicarbonate solution in THF (3.8 ml, 3.8 mmol). The mixture was heated at 60° C. for 4 hours, and then cooled to room temperature. After stored in refrigerator, the solid was separated, washed with MeOH and dried under vacuum to give [3-(2-oxo-1,2-dihydro-indol-3-ylidene)-1,3-dihydro-isobenzofuran-5-yl]-carbamic acid t-butyl ester as a yellow solid (250 mg, 36%).

$^1$H NMR (500 MHz, DMSO-$d_6$) δ ppm 1.50 (s, 9 H) 5.73 (s, 2 H) 6.83 (d, J=7.81 Hz, 1 H) 6.95 (t, J=7.57 Hz, 1 H) 7.11 (t, J=7.57 Hz, 1 H) 7.52 (d, J=8.30 Hz, 1 H) 7.69 (d, J=7.81 Hz, 1 H) 7.83 (d, J=7.81 Hz, 1 H) 9.59 (s, 1 H) 9.69 (s, 1 H) 10.33 (s, 1 H); LR MS (EI): 364 ($M^+$).

The following Example 36 was prepared using the experiment procedure described in Example 35, but with the appropriate reagent, reaction conditions and reactant substitutions that will be readily realized by those of ordinary skill in this art without the exercise of undue experimentation Example 36

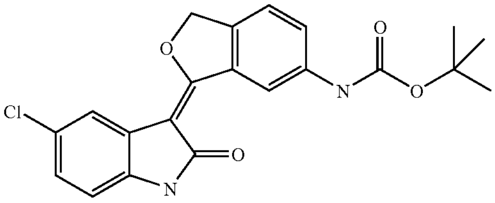

[3-(5-Chloro-2-oxo-1,2-dihydro-indol-3-ylidene)-1,3-dihydro-isobenzofuran-5-yl]-carbamic acid t-butyl ester $^1$H NMR (500 MHz, DMSO-$d_6$) δ ppm 1.50 (s, 9 H) 5.77 (s, 2 H) 6.83 (d, J=8.30 Hz, 1 H) 7.15 (dd, J=8.30, 2.44 Hz, 1 H) 7.55 (d, J=8.30 Hz, 1 H) 7.71 (d, J=7.81 Hz, 1 H) 7.80 (d, J=2.44 Hz, 1 H) 9.62 (s, 1 H) 9.68 (s, 1 H) 10.48 (s, 1 H); LR MS (EI): 398 ($M^+$) 400 (M+2).

Example 37

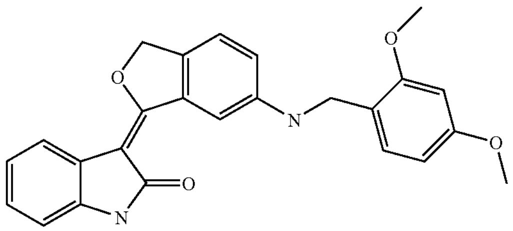

3-[6-(2,4-Dimethoxy-benzylamino)-3H-isobenzofuran-1-ylidene]-1,3-dihydro-indol-2-one To a stirred solution of 3-(6-amino-3H-isobenzofuran-1-ylidene)-1,3-dihydro-indol-2-one (1 g, 3.79 mmol) and 2,4-dimethoxybenzaldehyde (0.75 g, 4.54 mmol) in 1% AcOH/DMF (30 ml), was added sodium triacetoxyborohydride (3.2 g, 15.1 mmol). The mixture was stirred at room temperature for 16 hours, diluted with $CHCl_3$ (200 ml), washed with saturated aqueous $NaHCO_3$ solution (200 ml) and water (2×200 ml), dried over anhydrous $Na_2SO_4$. Removal of the solvent provided the crude product. Recrystallization of the crude product from MeOH resulted in 3-[6-(2,4-dimethoxy-benzylamino)-3H-isobenzofuran-1-ylidene]-1,3-dihydro-indol-2-one as a bright yellow solid (1.3 g, 83%).

$^1$H NMR (500 MHz, DMSO-$d_6$) δ ppm 3.73 (s, 3 H) 3.83 (s, 3 H) 4.21 (d, J=5.86 Hz, 2 H) 5.62 (s, 2 H) 6.23 (t, J=5.86 Hz, 1 H) 6.44 (dd, J=8.54, 2.20 Hz, 1 H) 6.57 (d, J=2.44 Hz, 1 H) 6.81 (d, J=7.32 Hz, 1 H) 6.91 (m, 2 H) 7.08 (m, 1 H) 7.23 (d, J=8.30 Hz, 1 H) 7.29 (d, J=8.30 Hz, 1 H) 7.82 (d, J=7.81 Hz, 1 H) 9.00 (d, J=2.44 Hz, 1 H) 10.30 (s, 1 H); LR MS (EI): 414 ($M^+$).

Example 38

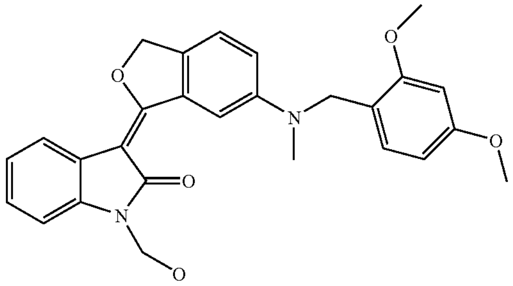

3-{6-[(2,4-Dimethoxy-benzyl)-methyl-amino]-3H-isobenzofuran-1-ylidene}-1-hydroxymethyl-1,3-dihydro-indol-2-one To a stirred suspension of 3-[6-(2,4-dimethoxy-benzylamino)-3H-isobenzofuran-1-ylidene]-1,3-dihydro-indol-2-one (1 g, 2.41 mmol) and 37% formaldehyde aqueous solution (2 ml, 27 mmol) in acetonitrile (30 ml), was added sodium cyanoborohydride (606 mg, 9.64 mmol). The mixture was stirred at room temperature for 2 hours, and 10% AcOH aqueous solution (30 ml) was added. The mixture was continuously stirred for another 10 minutes. The yellow precipitate separated, washed with MeOH and dried under vacuum to give a crude product. Recrystallization of the crude product with MeOH led to 3-{6-[(2,4-dimethoxy-benzyl)-methyl-amino]-3H-isobenzofuran-1-ylidene}-1-hydroxymethyl-1,3-dihydro-indol-2-one as yellow needles (0.9 g, 82%).

$^1$H NMR (500 MHz, DMSO-$d_6$) δ ppm 3.06 (s, 3 H) 3.72 (s, 3 H) 3.82 (s, 3 H) 4.53 (s, 2 H) 5.20 (d, J=6.83 Hz, 2 H) 5.70 (s, 2 H) 6.15 (t, J=7.32 Hz, 1 H) 6.42 (dd, J=8.54, 2.20 Hz, 1 H) 6.59 (d, J=2.44 Hz, 1 H) 6.90 (d, J=8.30 Hz, 1 H) 7.00 (dd, J=8.30, 2.44 Hz, 1 H) 7.04 (m, 1 H) 7.09 (d, J=7.81 Hz, 1 H) 7.19 (m, 1 H) 7.40 (d, J=8.30 Hz, 1 H) 7.91 (d, J=7.81 Hz, 1 H) 9.27 (d, J=2.44 Hz, 1 H); LR MS (FAB+): 459 (M+1).

Example 39

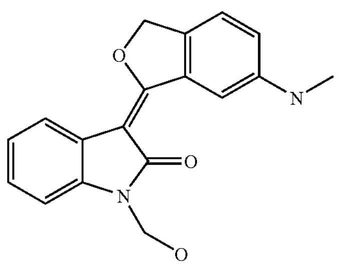

1-Hydroxymethyl-3-(6-methylamino-3H-isobenzofuran-1-ylidene)-1,3-dihydro-indol-2-one A solution of 3-{6-[(2,4-dimethoxy-benzyl)-methyl-amino]-3H-isobenzofuran-1-ylidene}-1-hydroxymethyl-1,3-dihydro-indol-2-one (600 mg, 1.31 mmol) in a mixture of THF (20 ml) and 2M HCl aqueous solution (20 ml) was heated at 50° C. for 16 hours. The mixture was concentrated, and then partitioned between $CHCl_3$ (200 ml) and saturated $NaHCO_3$ solution (200 ml). The aqueous layer was extracted with $CHCl_3$ (2×100 ml). The combined organic layers were washed with water (100 ml), dried over anhydrous $Na_2SO_4$, and evaporated to give a dark brown oil as a crude product. Purification of the crude product by silica gel column chromatography, eluted with a gradient of MeOH in EtOAc, yielded 1-hydroxymethyl-3-(6-methylamino-3H-isobenzofuran-1-ylidene)-1,3-dihydro-indol-2-one as a yellow solid (25 mg, 6%).

$^1$H NMR (500 MHz, DMSO-$d_6$) δ ppm 2.77 (d, J=4.88 Hz, 3 H) 5.21 (d, J=6.83 Hz, 2 H) 5.68 (s, 2 H) 6.04 (q, J=4.72 Hz, 1 H) 6.15 (t, J=6.83 Hz, 1 H) 6.92 (dd, J=8.30, 2.44 Hz, 1 H) 7.04 (t, J=7.57 Hz, 1 H) 7.09 (d, J=7.32 Hz, 1 H) 7.19 (t, J=7.08 Hz, 1 H) 7.35 (d, J=8.30 Hz, 1 H) 7.91 (d, J=7.32 Hz, 1 H) 8.95 (d, J=2.44 Hz, 1 H); LR MS (EI): 308 ($M^+$).

Example 40

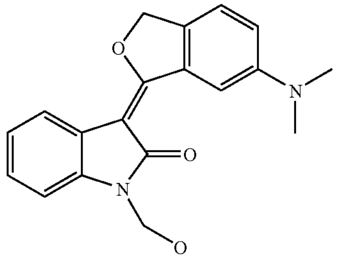

3-(6-Dimethylamino-3H-isobenzofuran-1-ylidene)-1-hydroxymethyl-1,3-dihydro-indol-2-one To a suspension of 3-(6-amino-3H-isobenzofuran-1-ylidene)-1,3-dihydro-indol-2-one (100 mg, 0.378 mmole) were added saturated formaldehyde aqueous solution, and sodium cyanoborohydride (300 mg, 4.77 mmole). The resulting mixture was stirred at room temperature for 1 hour, and then was acidified with 10% AcOH aqueous solution. After stirred for another 10 minutes, the reaction was partitioned between $CHCl_3$ and saturated $NaHCO_3$ aqueous solution. The aqueous layer was extracted with $CHCl_3$ (2×5 ml). The combined organic layers were washed with brine, and then dried over anhydrous $MgSO_4$. Removal of the solvent afforded a crude product. Recrystallization of the crude product from MeOH led to 3-(6-dimethylamino-3H-isobenzofuran-1-ylidene)-1-hydroxymethyl-1,3-dihydro-indol-2-one as a yellow solid (90 mg, 74%).

$^1$H NMR (500 MHz, $CDCl_3$) δ ppm 3.06 (s, 6 H) 5.41 (s, 2 H) 5.59 (s, 2 H) 6.98 (brs, 1 H) 7.04 (d, J=7.81 Hz, 1 H) 7.07 (td, J=7.69, 1.22 Hz, 1 H) 7.19 (td, J=7.69, 1.22 Hz, 1 H) 7.27 (d, J=8.30 Hz, 1 H) 7.99 (d, J=7.32 Hz, 1 H) 9.22 (s, 1 H).

Example 41

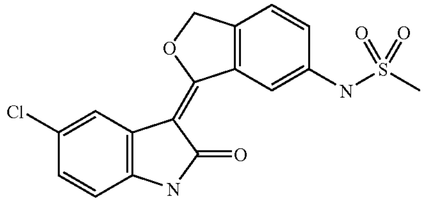

N-[3-(5-Chloro-2-oxo-1,2-dihydro-indol-3-ylidene)-1,3-dihydro-isobenzofuran-5-yl]-methanesulfonamide A mixture of 3-(6-amino-3H-isobenzofuran-1-ylidene)-5-chloro-1,3-dihydro-indol-2-one (100 mg, 0.33 mmol), pyridine (1 ml) and methanesulfonyl chloride (76 mg, 0.66 mmol) in THF (3.5 ml) was stirred for 16 hours, and was then poured into water (100 ml). The solid was filtered, washed with water and dried under vacuum to give a crude product. The crude product was triturated with MeOH/water to provide N-[3-(5-chloro-2-oxo-1,2-dihydro-indol-3-ylidene)-1,3-dihydro-isobenzofuran-5-yl]-methanesulfonamide as a yellow solid (100 mg, 81%).

$^1$H NMR (500 MHz, DMSO-$d_6$) δ ppm 3.09 (s, 3 H) 5.80 (s, 2 H) 6.84 (d, J=8.30 Hz, 1 H) 7.16 (m, 1 H) 7.49 (dd, J=8.30, 1.95 Hz, 1 H) 7.64 (d, J=8.30 Hz, 1 H) 7.80 (d, J=1.95 Hz, 1 H) 9.56 (d, J=1.95 Hz, 1 H) 10.08 (s, 1 H) 10.53 (s, 1 H).

Example 42

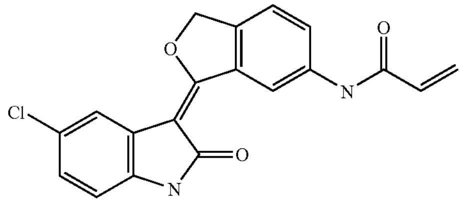

N-[3-(5-Chloro-2-oxo-1,2-dihydro-indol-3-ylidene)-1,3-dihydro-isobenzofuran-5-yl]-acrylamide To a stirred mixture of 3-(6-amino-3H-isobenzofuran-1-ylidene)-5-chloro-1,3-dihydro-indol-2-one (300 mg, 1.0 mmol) and triethylamine (0.41 ml, 3.0 mmol) in THF (10 ml), was added 3-bromopropionyl chloride (0.12 ml, 1.2 mmol). The mixture was heated at 45° C. for 2 hours, cooled to room temperature and poured into water (150 ml). The solid was filtered, washed with water and dried under vacuum to give crude product. The crude product was triturated with toluene to afforded N-[3-(5-chloro-2-oxo-1,2-dihydro-indol-3-ylidene)-1,3-dihydro-isobenzofuran-5-yl]-acrylamide as a bright yellow solid (315 mg, 89%).

$^1$H NMR (500 MHz, DMSO-$d_6$) δ ppm 5.79 (m, 3 H) 6.30 (dd, J=17.09, 1.95 Hz, 1 H) 6.54 (dd, J=16.84, 10.01 Hz, 1 H) 6.84 (d, J=8.30 Hz, 1 H) 7.16 (dd, J=8.30, 2.44 Hz, 1 H) 7.64 (d, J=8.79 Hz, 1 H) 7.81 (d, J=1.95 Hz, 1 H) 8.21 (d, J=8.30 Hz, 1 H) 9.68 (s, 1 H) 10.53 (d, J=21.48 Hz, 2 H).

Preparation 3

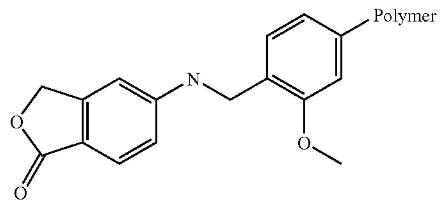

Preparation of 5-Aminophthalide-5-bound to 4-formyl-3-methoxyphenoxymethyl resin To a mixture of 5-aminophthalide (5.0 g, 33.5 mmol), 4-formyl-3-methoxyphenoxymethyl resin (6.1 g, 6.71 mmole) in 1% AcOH/DMF (100 ml) was added sodium triacetoxyborohydride (21.3 g, 100 mmol). The resulting mixture was gently stirred at room temperature for 48 hours. The resin was separated, and washed with DMF, MeOH, and $CHCl_3$, alternately. Removal of the solvent afforded 5-aminophthalide-5-bound to 4-formyl-3-methoxyphenoxymethyl resin (7.0 g).

Example 43

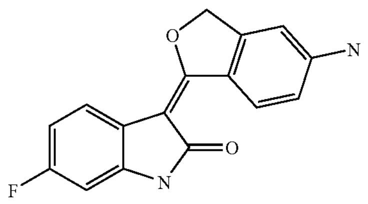

3-(5-Amino-3H-isobenzofuran-1-ylidene)-6-fluoro-1,3-dihydro-indol-2-one

A solution of 6-fluorooxindole (280 mg, 1.85 mmole), and 1M LiHMDS/THF (15 ml, 14 mmole) was shaken at room temperature for 5 minutes, followed by addition of 5-aminophthalide-5-bound to 4-formyl-3-methoxyphenoxymethyl resin (1000 mg). The resulting mixture was shaken at room temperature for 16 hours. The resin was separated, and washed with DMF, MeOH, and $CHCl_3$, alternately, to give 3-(5-amino-3H-isobenzofuran-1-ylidene)-6-fluoro-1,3-dihydro-indol-2-one-5-bonding to 4-formyl-3-methoxyphenoxymethyl resin.

The above washed resin was mixed with 10% trifluoroacetic acid in $CH_2Cl_2$ (5 ml), and stirred at room temperature for 0.5 hours. The resin residue was separated, and rinsed with $CHCl_3$. Evaporation of the combined filtrates resulted in a foam, which was recrytallized from $CHCl_3$/MeOH to yield the trifluoroacetate salt of 3-(5-amino-3H-isobenzofuran-1-ylidene)-6-fluoro-1,3-dihydro-indol-2-one (19 mg, 6%) as a yellow solid.

$^1$H NMR (500 MHz, DMSO-$d_6$) δ ppm 5.58 (s, 2 H) 6.57 (dd, J=9.28, 2.44 Hz, 1 H) 6.67 (m, 3 H) 7.68 (dd, J=8.30, 5.86 Hz, 1 H) 9.26 (d, J=8.79 Hz, 1 H) 10.34 (s, 1 H).

The following Example 44 was prepared using the experiment procedure described in Example 43, but with the appropriate reagent, reaction conditions and reactant substitutions that will be readily realized by those of ordinary skill in this art without the exercise of undue experimentation.

Example 44

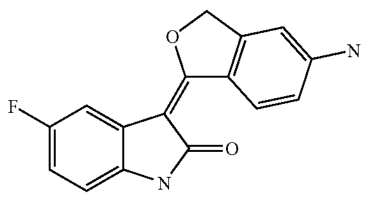

3-(5-Amino-3H-isobenzofuran-1-ylidene)-5-fluoro-1,3-dihydro-indol-2-one

$^1$H NMR (500 MHz, DMSO-$d_6$) δ ppm 5.61 (s, 2 H) 6.65 (m, 2 H) 6.71 (dd, J=8.30, 4.88 Hz, 1 H) 6.79 (m, 1 H) 7.46 (dd, J=10.01, 2.68 Hz, 1 H) 9.30 (d, J=9.28 Hz, 1 H).

Preparation 4

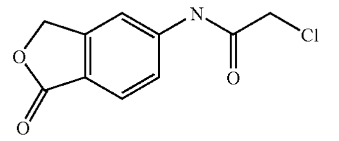

Preparation of 2-Chloro-N-(1-oxo-1,3-dihydro-isobenzofuran-5-yl)-acetamide

To a stirred solution of chloroacetic anhydride (7.0 g, 41 mmol) in THF (20 ml) was added 5-aminophthalide (3.0 g, 20 mmol). The mixture was stirred at 40° C. for 2 hours, cooled to room temperature and poured into water (100 ml) with stirring. The solid was filtered, washed with water, and dried under vacuum to give 2-chloro-N-(1-oxo-1,3-dihydro-isobenzofuran-5-yl)-acetamide as a light brown powder (4.0 g, 89%).

$^1$H NMR (500 MHz, DMSO-$d_6$) δ ppm 4.33 (s, 2 H) 5.38 (s, 2 H) 7.65 (d, J=8.30 Hz, 1 H) 7.82 (d, J=8.30 Hz, 1 H) 8.02 (s, 1 H) 10.79 (s, 1 H).

Preparation 5

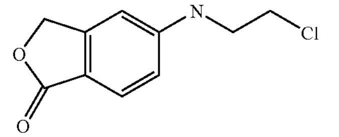

Preparation of 5-(2-Chloro-ethylamino)-3H-isobenzofuran-1-one

To a suspension of 2-chloro-N-(1-oxo-1,3-dihydroisobenzofuran-5-yl)-acetamide (1.0 g, 4.43 mmol) in THF (15 ml) was added 2M borane-methyl sulfide complex solution in THF (6.6 ml, 13.2 mmol) under nitrogen. After stirred at 60° C. under nitrogen for 2 hours, the resulting mixture was cooled in an ice bath, followed by the addition of aqueous HCl solution. The mixture was stirred at room temperature for 20 minutes, then heated at 60° C. for 40 minutes. After cooled to room temperature, the mixture was basified with aqueous NaOH solution, and then it was partitioned between water (50 ml) and $CHCl_3$ (50 ml). The aqueous layer was extracted with $CHCl_3$ (2×50 ml). The combined organic layers were washed with water, dried over anhydrous $Na_2SO_4$ Removal of the solvent led to a crude product. Trituration of the crude product with MeOH gave 5-(2-chloro-ethylamino)-3H-isobenzofuran-1-one as a light brown solid (0.4 g, 42%).

$^1$H NMR (500 MHz, DMSO-$d_6$) δ ppm 3.51 (q, J=6.35 Hz, 2 H) 3.75 (t, J=6.10 Hz, 2 H) 5.20 (s, 2 H) 6.70 (s, 1 H) 6.78 (dd, J=8.30, 1.95 Hz, 1 H) 7.05 (t, J=5.86 Hz, 1 H) 7.50 (d, J=8.30 Hz, 1 H).

Example 45

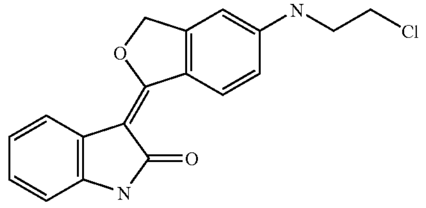

3-[5-(2-Chloro-ethylamino)-3H-isobenzofuran-1-ylidene]-1,3-dihydro-indol-2-one

To a stirred solution of oxindole (707 mg, 5.3 mmol) in anhydrous dimethoxyethane (20 ml) under nitrogen was added 1M LiHMDS/THF solution (18.5 ml, 18.5 mmol). The mixture was stirred at room temperature for 10 minutes, and 5-(2-chloro-ethylamino)-3H-isobenzofuran-1-one (900 mg, 4.25 mmol) was added. The mixture was stirred at room temperature for 2.5 hours and poured into 0.1M HCl solution (400 ml). The mixture was stirred for 30 min, then basified with aqueous NaOH solution. The precipitants were filtered, washed with water, and dried under vacuum to result in a crude product mixture. The crude product mixture was purified by silica gel column chromatography, eluted with a gradient of MeOH in $CHCl_3$. The major product, 3-[5-(2-chloro-ethylamino)-3H-isobenzofuran-1-ylidene]-1,3-dihydro-indol-2-one (Example 45), was obtained as a yellow solid (560 mg, 40%) and so was the minor product, 3-[5-(2-hydroxy-ethylamino)-3H-isobenzofuran-1-ylidene]-1,3-dihydro-indol-2-one (Example 93), as a yellow solid.

Example 45

$^1$H NMR (500 MHz, DMSO-$d_6$) δ ppm 3.55 (q, J=6.35 Hz, 2 H) 3.77 (t, J=6.10 Hz, 2 H) 5.64 (s, 2 H) 6.78 (m, 3 H) 6.90 (t, J=7.08 Hz, 1 H) 7.03 (m, 2 H) 7.75 (d, J=7.32 Hz, 1 H) 9.39 (d, J=8.79 Hz, 1 H) 10.22 (s, 1 H).

The following Example 46 through 47 were prepared using the experiment procedure described in Example 45, but with the appropriate reagent, reaction conditions and reactant substitutions that will be readily realized by those of ordinary skill in this art without the exercise of undue experimentation.

Example 46

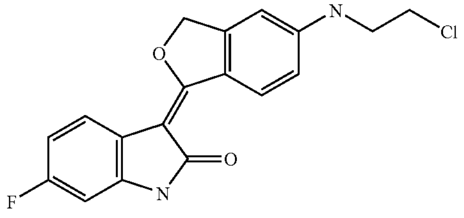

3-[5-(2-Chloro-ethylamino)-3H-isobenzofuran-1-ylidene]-6-fluoro-1,3-dihydro-indol-2-one $^1$H NMR (500 MHz, DMSO-$d_6$) δ ppm 3.54 (q, J=5.86 Hz, 2 H) 3.77 (t, J=6.10 Hz, 2 H) 5.64 (s, 2 H) 6.59 (dd, J=9.28, 2.44 Hz, 1 H) 6.71 (m, 1 H) 6.79 (m, 2 H) 7.07 (t, J=5.86 Hz, 1 H) 7.71 (dd, J=8.79, 5.86 Hz, 1 H) 9.33 (d, J=8.79 Hz, 1 H) 10.37 (s, 1 H).

Example 47

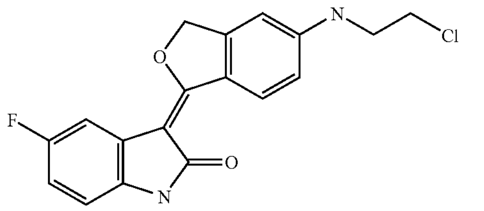

3-[5-(2-Chloro-ethylamino)-3H-isobenzofuran-1-ylidene]-5-fluoro-1,3-dihydro-indol-2-one $^1$H NMR (500 MHz, DMSO-$d_6$) δ ppm 3.55 (q, J=5.86 Hz, 2 H) 3.77 (t, J=6.10 Hz, 2 H) 5.66 (s, 2 H) 6.74 (dd, J=8.30, 4.88 Hz, 1 H) 6.82 (m, 3 H) 7.13 (br, 1 H) 7.48 (dd, J=10.01, 2.69 Hz, 1 H) 9.36 (d, J=9.28 Hz, 1 H) 10.23 (s, 1 H).

Example 48

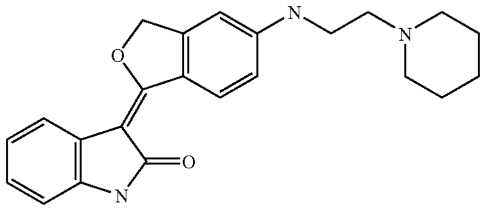

3-[5-(2-Piperidin-1-yl-ethylamino)-3H-isobenzofuran-1-ylidene]-1,3-dihydro-indol-2-one A mixture of 3-[5-(2-chloro-ethylamino)-3H-isobenzofuran-1-ylidene]-1,3-dihydro-indol-2-one (1.10 g, 3.37 mmol) and piperidine (8 ml, 80.9 mmol) was heated at 110° C. for 4 hours. After cooled to room temperature, the mixture was poured into an ice water (150 ml) with stirring. The solid was filtered, washed with water and dried to give a crude product. Trituration of the crude product with $CHCl_3$/hexanes afforded 3-[5-(2-piperidin-1-yl-ethylamino)-3H-isobenzofuran-1-ylidene]-1,3-dihydro-indol-2-one as a yellow solid (1.13 g, 89%).

$^1$H NMR (500 MHz, DMSO-$d_6$) δ ppm 1.39 (m, 2 H) 1.51 (m, 4 H) 2.39 (br, 4 H) 2.48 (m, 2 H) 3.24 (q, J=5.86 Hz, 2 H) 5.62 (s, 2 H) 6.65 (t, J=5.37 Hz, 1 H) 6.70 (s, 1 H) 6.74 (dd, J=8.79, 1.95 Hz, 1 H) 6.78 (d, J=7.32 Hz, 1 H) 6.89 (t, J=7.08 Hz, 1 H) 7.00 (td, J=7.69, 1.22 Hz, 1 H) 7.74 (d, J=7.81 Hz, 1 H) 9.36 (d, J=8.79 Hz, 1 H) 10.20 (s, 1 H).

The following Example 49 through 63 were prepared using the experiment procedure described in Example 48, but with the appropriate reagent, reaction conditions and reactant substitutions that will be readily realized by those of ordinary skill in this art without the exercise of undue experimentation.

Example 49

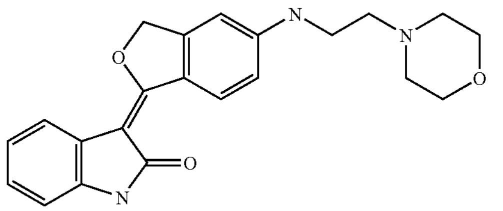

3-[5-(2-Morpholin-4-yl-ethylamino)-3H-isobenzofuran-1-ylidene]-1,3-dihydro-indol-2-one $^1$H NMR (500 MHz, DMSO-$d_6$) δ ppm 2.44 (brs, 4 H) 2.53 (t, J=6.83 Hz, 2 H) 3.27 (q, J=6.35 Hz, 2 H) 3.60 (t, J=4.39 Hz, 4 H) 5.63 (s, 2 H) 6.70 (m, 2 H) 6.75 (dd, J=9.03, 2.20 Hz, 1 H) 6.78 (d, J=7.81 Hz, 1 H) 6.89 (t, J=7.32 Hz, 1 H) 7.01 (t, J=7.57 Hz, 1 H) 7.74 (d, J=7.32 Hz, 1 H) 9.36 (d, J=8.79 Hz, 1 H) 10.20 (s, 1 H); LR MS (EI): 377 (M+).

Example 50

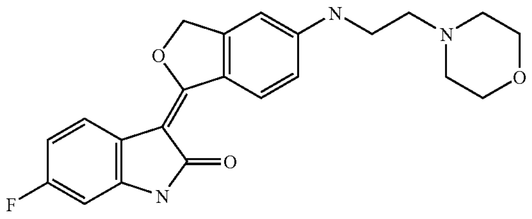

6-Fluoro-3-[5-(2-morpholin-4-yl-ethylamino)-3H-isobenzofuran-1-ylidene]-1,3-dihydro-indol-2-one $^1$H NMR (500 MHz, DMSO-$d_6$) δ ppm 2.44 (brs, 4 H) 2.53 (t, J=6.59 Hz, 2 H) 3.27 (q, J=6.18 Hz, 2 H) 3.59 (t, J=4.39 Hz, 4 H) 5.63 (s, 2 H) 6.59 (dd, J=9.28, 2.44 Hz, 1 H) 6.70 (m, 3 H) 6.75 (dd, J=9.03, 2.20 Hz, 1 H) 7.70 (dd, J=8.54, 5.61 Hz, 1 H) 9.31 (d, J=8.79 Hz, 1 H) 10.36 (s, 1 H).

Example 51

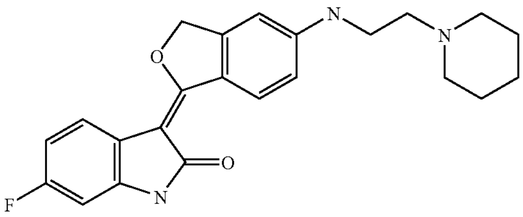

6-Fluoro-3-[5-(2-piperidin-1-yl-ethylamino)-3H-isobenzofuran-1-ylidene]-1,3-dihydro-indol-2-one $^1$H NMR (500 MHz, DMSO-$d_6$) δ ppm 1.38 (m, 2 H) 1.51 (m, 4 H) 2.40 (brs, 4 H) 2.48 (m, 2 H) 3.24 (q, J=6.35 Hz, 2 H) 5.62 (s, 2H) 6.59 (dd, J=9.52, 2.69 Hz, 1 H) 6.70 (m, 3 H) 6.74 (dd, J=8.79, 1.95 Hz, 1 H) 7.70 (dd, J=8.54, 5.61 Hz, 1 H) 9.30 (d, J=8.79 Hz, 1 H) 10.35 (s, 1 H).

Example 52

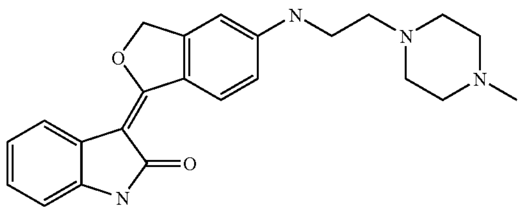

3-{5-[2-(4-Methyl-piperazin-1-yl)-ethylamino]-3H-isobenzofuran-1-ylidene}-1,3-dihydro-indol-2-one $^1$H NMR (500 MHz, DMSO-$d_6$) δ ppm 2.16 (s, 3 H) 2.34 (brs, 4 H) 2.45 (brs, 4 H) 2.53 (m, 2 H) 3.25 (m, 2 H) 5.63 (s, 2 H) 6.66 (t, J=5.37 Hz, 1 H) 6.71 (s, 1 H) 6.76 (m, 2 H) 6.89 (t, J=7.57 Hz, 1 H) 7.01 (t, J=7.57 Hz, 1 H) 7.74 (d, J=7.81 Hz, 1 H) 9.36 (d, J=8.79 Hz, 1 H) 10.20 (s, 1 H).

Example 53

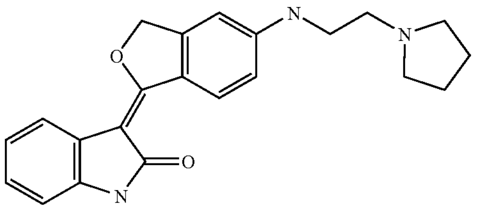

3-[5-(2-Pyrrolidin-1-yl-ethylamino)-3H-isobenzofuran-1-ylidene]-1,3-dihydro-indol-2-one $^1$H NMR (500 MHz, DMSO-$d_6$) δ ppm 1.70 (brs, 4 H) 2.50 (brs, 4 H) 2.64 (t, J=6.59 Hz, 2 H) 3.26 (q, J=6.35 Hz, 2 H) 5.63 (s, 2 H) 6.75 (m, 4 H) 6.89 (t, J=7.81 Hz, 1 H) 7.01 (t, J=7.08 Hz, 1 H) 7.74 (d, J=7.32 Hz, 1 H) 9.36 (d, J=8.79 Hz, 1 H) 10.20 (s, 1 H).

Example 54

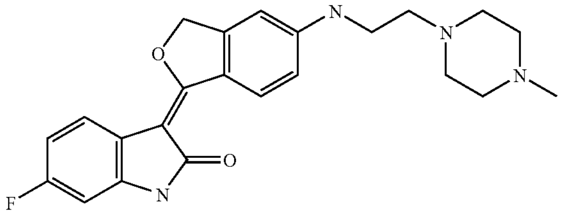

6-Fluoro-3-{5-[2-(4-methyl-piperazin-1-yl)-ethylamino]-3H-isobenzofuran-1-ylidene}-1,3-dihydro-indol-2-one $^1$H NMR (500 MHz, DMSO-$d_6$) δ ppm 2.16 (s, 3 H) 2.36 (br, 4 H) 2.45 (br, 4 H) 2.53 (m, 2 H) 3.25 (q, J=6.35 Hz, 2 H) 5.62 (s, 2 H) 6.59 (dd, J=9.28, 2.44 Hz, 1 H) 6.71 (m, 4 H) 7.70 (dd, J=8.79, 5.86 Hz, 1 H) 9.31 (m, J=8.79 Hz, 1 H) 10.36 (s, 1 H); LR MS (FAB+): 409 (M+1).

Example 55

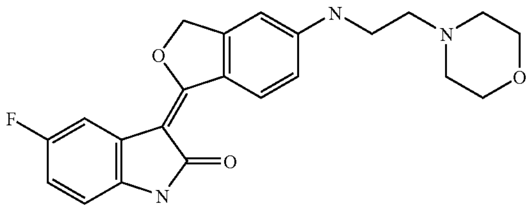

5-Fluoro-3-[5-(2-morpholin-4-yl-ethylamino)-3H-isobenzofuran-1-ylidene]-1,3-dihydro-indol-2-one $^1$H NMR (500 MHz, DMSO-$d_6$) δ ppm 2.43 (brs, 4 H) 2.53 (t, J=6.59 Hz, 2 H) 3.27 (q, J=6.35 Hz, 2 H) 3.59 (t, J=4.39 Hz, 4 H) 5.65 (s, 2 H) 6.78 (m, 5 H) 7.48 (dd, J=9.76, 2.44 Hz, 1 H) 9.35 (d, J=9.28 Hz, 1 H) 10.22 (s, 1 H).

Example 56

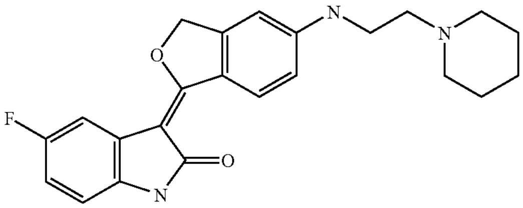

5-Fluoro-3-[5-(2-piperidin-1-yl-ethylamino)-3H-isobenzofuran-1-ylidene]-1,3-dihydro-indol-2-one $^1$H NMR (500 MHz, DMSO-$d_6$) δ ppm 1.39 (m, 2 H) 1.51 (m, 4 H) 2.41 (brs, 4 H) 2.49 (m, 2 H) 3.26 (m, 2 H) 5.65 (s, 2 H) 6.74 (m, 4 H) 6.81 (m, 1 H) 7.48 (dd, J=10.01, 2.68 Hz, 1 H) 9.34 (d, J=9.27 Hz, 1 H) 10.22 (s, 1 H).

Example 57

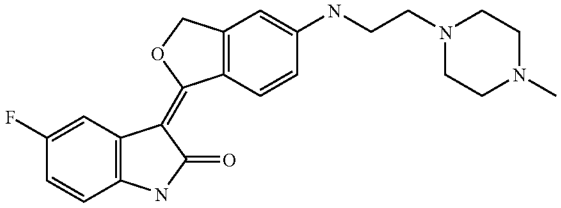

5-Fluoro-3-{5-[2-(4-methyl-piperazin-1-yl)-ethylamino]-3H-isobenzofuran-1-ylidene}-1,3-dihydro-indol-2-one

$^1$H NMR (500 MHz, DMSO-$d_6$) δ ppm 2.16 (s, 3 H) 2.35 (brs, 4 H) 2.44 (brs, 4 H) 2.53 (m, 2 H) 3.26 (q, J=6.02 Hz, 2 H) 5.65 (s, 2 H) 6.77 (m, 5 H) 7.48 (dd, J=10.01, 2.20 Hz, 1 H) 9.34 (d, J=9.28 Hz, 1 H) 10.22 (s, 1 H).

Example 58

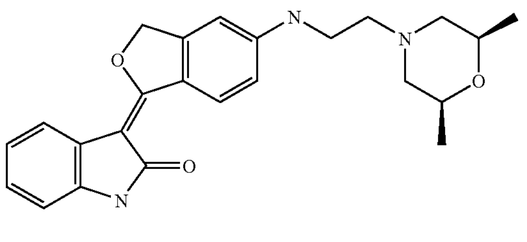

3-{5-[2-((2R,6S)-2,6-Dimethyl-morpholin-4-yl)-ethylamino]-3H-isobenzofuran-1-ylidene}-1,3-dihydro-indol-2-one

$^1$H NMR (500 MHz, DMSO-$d_6$) δ ppm 1.05 (d, J=6.35 Hz, 6 H) 1.67 (t, J=10.74 Hz, 2 H) 2.50 (t, J=5.86 Hz, 2 H) 2.80 (d, J=10.74 Hz, 2 H) 3.26 (q, J=5.86 Hz, 2 H) 3.57 (m, 2 H) 5.62 (s, 2 H) 6.67 (t, J=5.13 Hz, 1 H) 6.70 (s, 1 H) 6.74 (d, J=8.79 Hz, 1 H) 6.77 (d, J=7.32 Hz, 1 H) 6.89 (t, J=7.32 Hz, 1 H) 7.00 (t, J=7.08 Hz, 1 H) 7.74 (d, J=7.32 Hz, 1 H) 9.36 (d, J=8.79 Hz, 1 H) 10.20 (s, 1 H).

Example 59

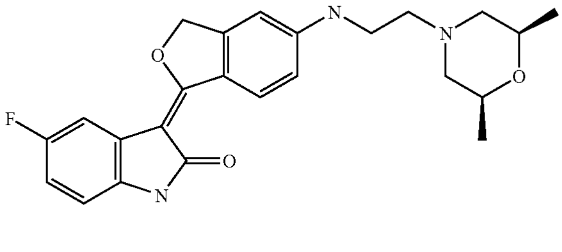

3-{5-[2((2R,6S)-2,6-Dimethyl-morpholin-4-yl)-ethylamino]-3H-isobenzofuran-1-ylidene}-5-fluoro-1,3-dihydro-indol-2-one

[1]NMR (500 MHz, DMSO-$d_6$) δ ppm 1.05 (d, J=6.35 Hz, 6 H) 1.67 (t, J=10.74 Hz, 2 H) 2.50 (t, J=6.35 Hz, 2 H) 2.80 (d, J=10.74 Hz, 2 H) 3.27 (q, J=6.35 Hz, 2 H) 3.57 (m, 2 H) 5.65 (s, 2 H) 6.77 (m, 5 H) 7.48 (dd, J=9.76, 2.93 Hz, 1 H) 9.34 (d, J=8.79 Hz, 1 H) 10.22 (s, 1 H).

Example 60

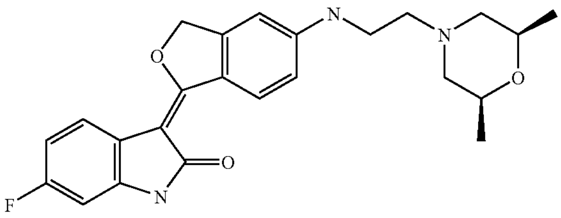

3-{5-[2-((2R,6S)-2,6-Dimethyl-morpholin-4-yl)-ethylamino]-3H-isobenzofuran-1-ylidene}-6-fluoro-1,3-dihydro-indol-2-one

$^1$H NMR (500 MHz, DMSO-$d_6$) δ ppm 1.05 (d, J=6.35 Hz, 6 H) 1.67 (t, J=10.74 Hz, 2 H) 2.50 (t, J=6.35 Hz, 2 H) 2.80 (d, J=10.74 Hz, 2 H) 3.26 (q, J=6.35 Hz, 2 H) 3.57 (m, 2 H) 5.62 (s, 2 H) 6.58 (dd, J=9.28, 2.93 Hz, 1 H) 6.70 (m, 3 H) 6.74 (dd, J=9.03, 2.20 Hz, 1 H) 7.70 (dd, J=8.30, 5.86 Hz, 1 H) 9.31 (d, J=8.79 Hz, 1 H) 10.35 (s, 1 H).

Example 61

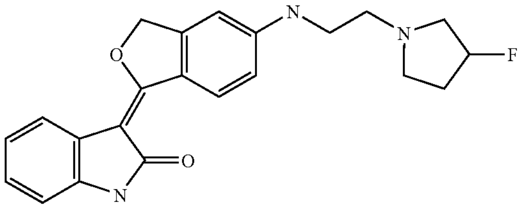

3-{5-[2-(3-Fluoro-pyrrolidin-1-yl)-ethylamino]-3H-isobenzofuran-1-ylidene}-1,3-dihydro-indol-2-one

$^1$H NMR (500 MHz, DMSO-$d_6$) δ ppm 1.9~2.2 (m, 4H) 2.65 (brs, 2 H) 2.86 (brs, 2 H) 3.29 (m, 2 H) 5.21 (two broad peaks, $J_{H-F}$=56.14 Hz, 1 H) 5.63 (s, 2 H) 6.75 (m, 4 H) 6.89 (td, J=7.57, 0.98 Hz, 1 H) 7.00 (td, J=7.57, 0.98 Hz, 1 H) 7.74 (d, J=7.81 Hz, 1 H) 9.36 (d, J=8.79 Hz, 1 H) 10.20 (s, 1 H)

Example 62

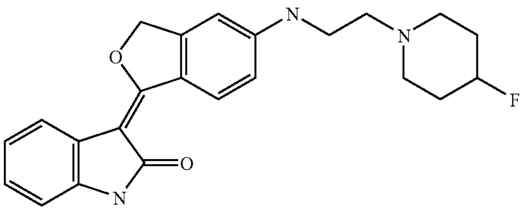

3-{5-[2-(4-Fluoro-piperidin-1-yl)-ethylamino]-3H-isobenzofuran-1-ylidene}-1,3-dihydro-indol-2-one $^1$H NMR (500 MHz, DMSO-$d_6$) δ ppm 1.71 (m, 2 H) 1.86 (m, 2 H) 2.37 (brs, 2 H) 2.53 (t, J=6.59 Hz, 2 H) 2.60 (brs, 2 H) 3.25 (q, J=6.35 Hz, 2 H) 4.68 (two broad peaks, $J_{H-F}$=49.3 Hz, 1 H) 5.62 (s, 2 H) 6.72 (m, 4 H) 6.89 (t, J=7.08 Hz, 1 H) 7.00 (t, J=7.57 Hz, 1 H) 7.74 (d, J=7.32 Hz, 1 H) 9.36 (d, J=8.79 Hz, 1 H) 10.20 (s, 1 H).

Example 63

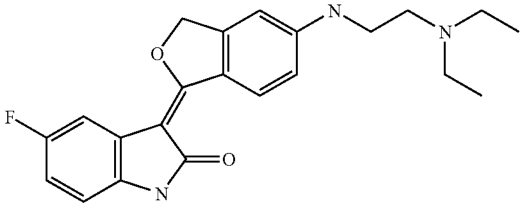

3-[5-(2-Diethylamino-ethylamino)-3H-isobenzofuran-1-ylidene]-5-fluoro-1,3-dihydro-indol-2-one Preparation 6

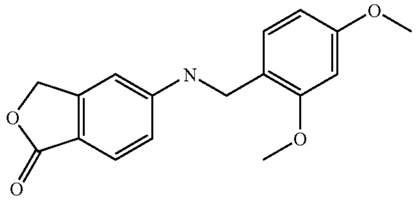

Preparation of 5-(2,4-Dimethoxy-benzylamino)-3H-isobenzofuran-1-one

To a stirred solution of 5-aminophthalide (11.7 g, 78 mmol) and 2,4-dimethoxybenzaldehyde (15.5 g, 93.6 mmol) in 1% AcOH/DMF (60 ml), was added sodium triacetoxyborohydride (50.0 g, 236 mmol). The mixture was stirred at room temperature for 16 hours, diluted with EtOAc (400 ml), washed with saturated $NaHCO_3$ solution (3×400 ml) and water (400 ml), dried over anhydrous $Na_2SO_4$, and evaporated to provide a crude product. Trituration of the crude product with MEOH gave 5-(2,4-dimethoxy-benzylamino)-3H-isobenzofuran-1-one as an off-white powder (19.0 g, 82%).

$^1$H NMR (500 MHz, DMSO-$d_6$) δ ppm 3.74 (s, 3 H) 3.82 (s, 3 H) 4.21 (d, J=5.86 Hz, 2 H) 5.15 (s, 2 H) 6.48 (dd, J=8.54, 2.20 Hz, 1 H) 6.58 (m, 2 H) 6.73 (d, J=6.83 Hz, 1 H) 7.12 (d, J=8.30 Hz, 2 H) 7.46 (d, J=8.79 Hz, 1 H).

Example 64

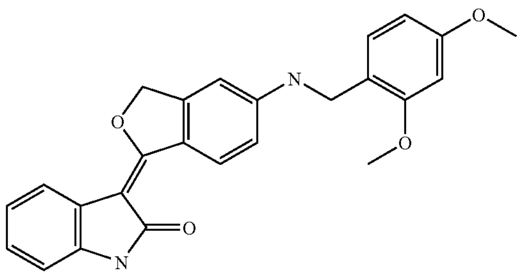

3-[5-(2,4-Dimethoxy-benzylamino)-3H-isobenzofuran-1-ylidene]-1,3-dihydro-indol-2-one To a stirred solution of oxindole (555 mg, 4.17 mmol) in anhydrous dimethoxyethane (20 ml) under nitrogen was added 2.5M n-BuLi solution in hexane (3.67 ml, 9.17 mmol), and the resulting mixture was stirred at room temperature for 10 minutes, followed by the addition of 5-(2,4-dimethoxy-benzylamino)-3H-isobenzofuran-1-one (1.0 g, 3.34 mmol). After stirred at room temperature for 2.5 hours the mixture was poured into 1M HCl aqueous solution (100 ml). The resulting solid was separated, washed with water, and dried under vacuum to afford a crude product. Trituration of the crude product with MeOH produced 3-[5-(2,4-dimethoxy-benzylamino)-3H-isobenzofuran-1-ylidene]-1,3-dihydro-indol-2-one as a yellow solid (630 mg, 46%).

$^1$H NMR (500 MHz, DMSO-$d_6$) δ ppm 3.74 (s, 3 H) 3.83 (s, 3 H) 4.25 (d, J=5.37 Hz, 2 H) 5.60 (s, 2 H) 6.49 (dd, J=8.30, 2.44 Hz, 1 H) 6.59 (d, J=1.95 Hz, 1 H) 6.67 (s, 1 H)6.76 (m, 2 H)6.89 (m, 1 H)7.00 (m, 1 H)7.14 (m, 2 H)7.73 (d, J=7.81 Hz, 1 H) 9.35 (d, J=8.79 Hz, 1 H) 10.19 (s, 1 H).

Example 65

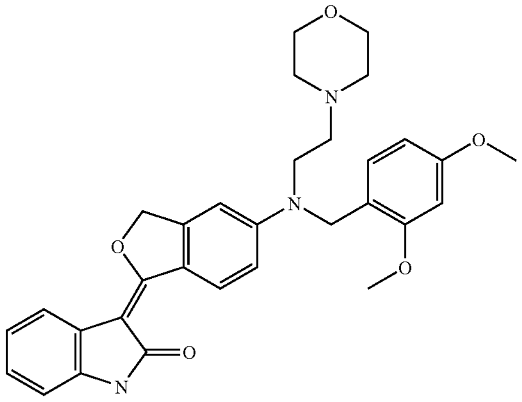

3-{5-[(2,4-Dimethoxy-benzyl)-(2-morpholin-4-yl-ethyl)-amino]-3H-isobenzofuran-1-ylidene}-1,3-dihydro-indol-2-one A mixture of 3-[5-(2,4-dimethoxy-benzylamino)-3H-isobenzofuran-1-ylidene]-1,3-dihydro-indol-2-one (100 mg, 0.24 mmol), 4-(2-iodo-ethyl)-morpholine (90 mg, 0.37 mmol), N,N-diisopropylethylamine (63 mg, 0.49 mmol) and silver triflate (75 mg (0.29 mmol) in 1,4-dioxane (5 ml) was heated at 85° C. under nitrogen for 16 hours. Purification of the mixture by silica gel chromatography, eluted with a gradient of MeOH in $CHCl_3$ led to 3-{5-[(2,4-dimethoxy-benzyl)-(2-morpholin-4-yl-ethyl)-amino]-3H-isobenzofuran-1-ylidene}-1,3-dihydro-indol-2-one as a yellow solid (40 mg, 31%).

$^1$H NMR (500 MHz, $CDCl_3$) δ ppm 2.51 (brs, 4 H) 2.65 (t, J=6.83 Hz, 2 H) 3.64 (t, J=6.59 Hz, 2 H) 3.71 (brs, 4 H) 3.79 (s, 3 H) 3.86 (s, 3 H) 4.57 (s, 2 H) 5.52 (s, 2 H) 6.38 (dd, J=8.30, 2.44 Hz, 1 H) 6.50 (d, J=2.44 Hz, 1 H) 6.59 (s, 1 H) 6.85 (m, 3 H) 7.01 (t, J=7.57 Hz, 1 H) 7.08 (t, J=7.57 Hz, 1 H) 7.49 (s, 1 H) 7.91 (d, J=7.32 Hz, 1 H) 9.50 (d, J=8.79 Hz, 1 H).

Preparation 7

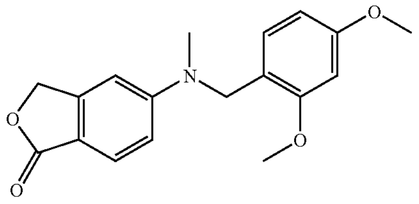

Preparation of 5-[(2,4-Dimethoxy-benzyl)-methyl-amino]-3H-isobenzofuran-1-one

To a stirred suspension of 5-(2,4-dimethoxy-benzylamino)-3H-isobenzofuran-1-one (18.0 g, 60 mmol) in acetonitrile (200 ml), was added 37% formaldehyde aqueous solution (44.7 ml, 600 mmol) and sodium cyanoborohydride (8.31 g, 132 mmol). The mixture was cooled to 0° C., followed by addition of 10% AcOH aqueous solution (150 ml). The mixture was stirred from 0° C. to room temperature during 2.5 hour period. The resulting solid was filtered, washed with acetonitrile and dried under vacuum to give 5-[(2,4-dimethoxy-benzyl)-methyl-amino]-3H-isobenzofuran-1-one as off-white powder (15.3 g, 81%).

$^1$H NMR (500 MHz, DMSO-$d_6$) δ ppm 3.11 (s, 3 H) 3.72 (s, 3 H) 3.82 (s, 3 H) 4.54 (s, 2 H) 5.20 (s, 2 H) 6.44 (dd, J=8.54, 2.20 Hz, 1 H) 6.60 (d, J=2.44 Hz, 1 H) 6.75 (s, 1 H) 6.80 (d, 2 H) 7.55 (d, J=8.79 Hz, 1 H); LR MS (EI): 313 ($M^+$).

Example 66

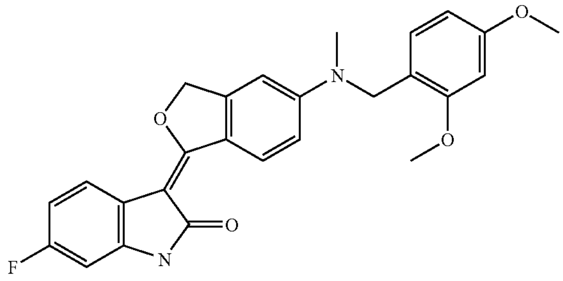

3-{5-[(2,4-Dimethoxy-benzyl)-methyl-amino]-3H-isobenzofuran-1-ylidene}-6-fluoro-1,3-dihydro-indol-2-one To a stirred solution of 6-fluorooxindole (0.60 g, 3.99 mmol) in anhydrous dimethoxyethane (20 ml) under nitrogen was added 2.5M n-BuLi solution in hexane (3.5 ml, 8.75 mmol). After the reaction was stirred at room temperature for 10 minutes, 5-[(2,4-dimethoxy-benzyl)-methyl-amino]-3H-isobenzofuran-1-one (1.0 g, 3.19 mmol) was added. After stirred at room temperature for 2.5 hours, the reaction mixture was poured into 1M HCl aqueous solution (70 ml), and then basified with NaOH aqueous solution. The solid was separated, washed with water, and dried under vacuum to give a crude product. Trituration of the crude product with benzene yielded 3-{5-[(2,4-dimethoxy-benzyl)-methyl-amino]-3H-isobenzofuran-1-ylidene}-6-fluoro-1,3-dihydro-indol-2-one as a yellow solid (0.91 g, 64%).

$^1$H NMR (500 MHz, DMSO-$d_6$) δ ppm 3.11 (s, 3 H) 3.71 (s, 3 H) 3.81 (s, 3 H) 4.55 (s, 2 H) 5.62 (s, 2 H) 6.43 (dd, J=8.30, 2.44 Hz, 1 H) 6.58 (m, 2 H) 6.68 (m, 1 H) 6.83 (m, 3 H) 7.68 (dd, J=8.54, 5.61 Hz, 1 H) 9.33 (d, J=9.28 Hz, 1 H) 10.34 (s, 1 H); LR MS (EI): 446 ($M^+$).

The following Example 67 through 76 were prepared using the experiment procedure described in Example 66, but with the appropriate reagent, reaction conditions and reactant substitutions that will be readily realized by those of ordinary skill in this art without the exercise of undue experimentation.

Example 67

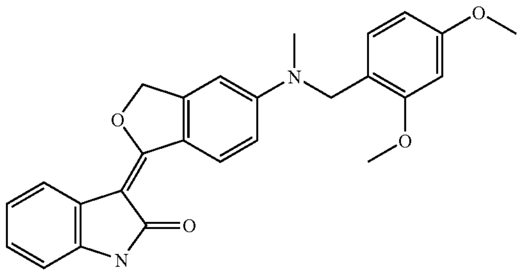

3-{5-[(2,4-Dimethoxy-benzyl)-methyl-amino]-3H-isobenzofuran-1-ylidene}-1,3-dihydro-indol-2-one $^1$H NMR (500 MHz, DMSO-$d_6$) δ ppm 3.13 (s, 3 H) 3.73 (s, 3 H) 3.83 (s, 3 H) 4.57 (s, 2 H) 5.63 (s, 2 H) 6.45 (dd, J=8.30, 2.44 Hz, 1 H) 6.61 (d, J=2.44 Hz, 1 H) 6.84 (m, 5 H) 7.01 (m, 1 H) 7.74 (d, J=7.32 Hz, 1 H) 9.40 (d, J=8.79 Hz, 1 H) 10.21 (s, 1 H); LR MS (EI): 428 ($M^+$).

Example 68

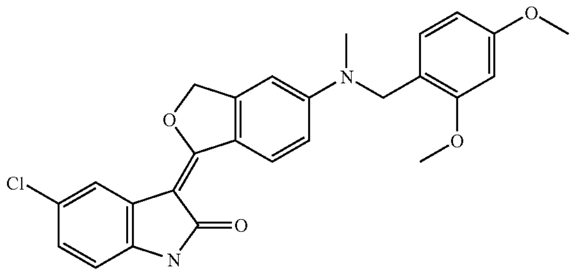

5-Chloro-3-{5-[(2,4-dimethoxy-benzyl)-methyl-amino]-3H-isobenzofuran-1-ylidene}-1,3-dihydro-indol-2-one $^1$H NMR (500 MHz, DMSO-$d_6$) δ ppm 3.12 (s, 3 H) 3.71 (s, 3 H) 3.81 (s, 3 H) 4.56 (s, 2 H) 5.66 (s, 2 H) 6.43 (dd, J=8.30, 2.44 Hz, 1 H) 6.59 (d, J=2.44 Hz, 1 H) 6.76 (d,J=7.81 Hz, 1 H) 6.84 (m, 3 H) 7.02 (dd, J=8.30, 1.95 Hz, 1 H) 7.69 (d, J=1.95 Hz, 1 H) 9.36 (d, J=9.28 Hz, 1 H) 10.33 (s, 1 H); LR MS (EI): 462 ($M^+$) 464 (M+2).

Example 69

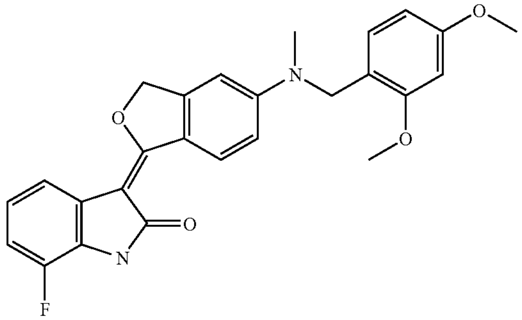

3-{5-[(2,4-Dimethoxy-benzyl)-methyl-amino]-3H-isobenzofuran-1-ylidene}-7-fluoro-1,3-dihydro-indol-2-one $^1$H NMR (500 MHz, DMSO-$d_6$) δ ppm 3.12 (s, 3 H) 3.71 (s, 3 H) 3.81 (s, 3 H) 4.56 (s, 2 H) 5.64 (s, 2 H) 6.43 (dd, J=8.30, 2.44 Hz, 1 H) 6.59 (d, J=1.95 Hz, 1 H) 6.86 (m, 5 H) 7.56 (m, 1 H) 9.38 (d, J=9.28 Hz, 1 H) 10.65 (s, 1 H); LR MS (EI): 446 ($M^+$).

Example 70

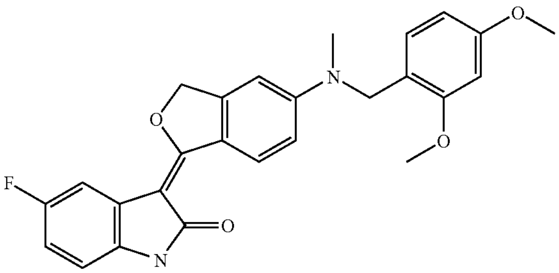

3-{5-[(2,4-Dimethoxy-benzyl)-methyl-amino]-3H-isobenzofuran-1-ylidene}-5-fluoro-1,3-dihydro-indol-2-one $^1$H NMR (500 MHz, DMSO-$d_6$) δ ppm 3.12 (s, 3 H) 3.71 (s, 3 H) 3.81 (s, 3 H) 4.56 (s, 2 H) 5.64 (s, 2 H) 6.43 (dd, J=8.54, 2.20 Hz, 1 H) 6.59 (d, J=1.95 Hz, 1 H) 6.72 (dd, J=8.54, 4.64 Hz, 1 H) 6.82 (m, 4 H) 7.46 (dd, J=10.01, 2.69 Hz, 1 H) 9.37 (d, J=9.28 Hz, 1 H) 10.21 (s, 1 H); LR MS (EI): 446 ($M^+$).

Example 71

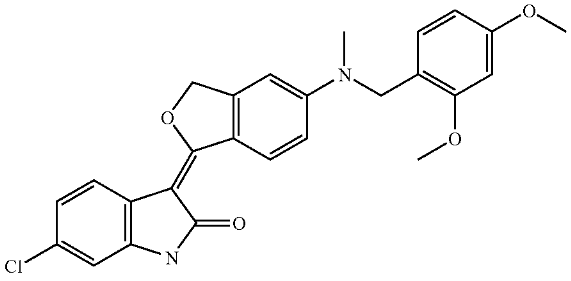

6-Chloro-3-{5-[(2,4-dimethoxy-benzyl)-methyl-amino]-3H-isobenzofuran-1-ylidene}-1,3-dihydro-indol-2-one $^1$H NMR (500 MHz, DMSO-$d_6$) δ ppm 3.12 (s, 3 H) 3.71 (s, 3 H) 3.81 (s, 3 H) 4.56 (s, 2 H) 5.63 (s, 2 H) 6.43 (dd, J=8.30, 1.95 Hz, 1 H) 6.59 (d, J=2.44 Hz, 1 H) 6.83 (m, 4 H) 6.91 (dd, J=8.30, 1.95 Hz, 1 H) 7.68 (d, J=8.30 Hz, 1 H) 9.34 (d, J=9.28 Hz, 1 H) 10.35 (s, 1 H); LR MS (EI): 462 ($M^+$) 464 (M+2).

Example 72

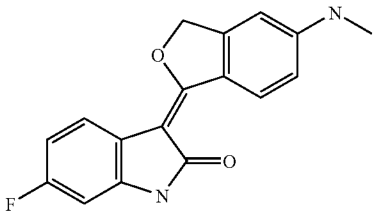

6-Fluoro-3-(5-methylamino-3H-isobenzofuran-1-ylidene)-1,3-dihydro-indol-2-one

To a stirred suspension of (3-{5-[(2,4-dimethoxy-benzyl)-methyl-amino]-3H-isobenzofuran-1-ylidene}-6-fluoro-1,3-dihydro-indol-2-one (197 mg, 0.44 mmol) in methylene chloride (10 ml) was added trifluoroacetic acid (1 ml). The mixture was stirred for 30 minutes at room temperature and then evaporated to give a residue. The residue was treated with 50% MeOH in water (25 ml, containing 1 ml of triethylamine) with heating for 30 minutes. After filtered and dried under vacuum, the resulting solid was mixed with acetone (50 ml), and heated at 50° C. for 30 minutes. The mixture was cooled to room temperature and filtered. The filtrate solution was concentrated under reduced pressure to give a crude product. Trituration of the crude product with $CHCl_3$/hexanes afforded 6-fluoro-3-(5-methylamino-3H-isobenzofuran-1-ylidene)-1,3-dihydro-indol-2-one as a yellow solid (100 mg, 76%).

$^1$H NMR (500 MHz, DMSO-$d_6$) δ ppm 2.77 (d, J=4.88 Hz, 3 H) 5.62 (s, 2 H) 6.57 (dd, J=9.28, 2.44 Hz, 1 H) 6.63 (s, 1 H) 6.69 (m, 2 H) 6.85 (q, J=4.88 Hz, 1 H) 7.69 (dd, J=8.30, 5.86 Hz, 1 H) 9.31 (d, J=8.79 Hz, 1 H) 10.34 (s, 1 H); LR MS (EI): 296 ($M^+$).

The following Example 73 through 76 were prepared using the experiment procedure described in Example 72, but with the appropriate reagent, reaction conditions and reactant substitutions that will be readily realized by those of ordinary skill in this art without the exercise of undue experimentation Example 73

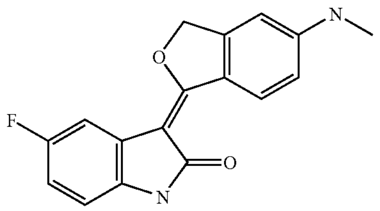

5-Fluoro-3-(5-methylamino-3H-isobenzofuran-1-ylidene)-1,3-dihydro-indol-2-one $^1$H NMR (500 MHz, DMSO-$d_6$) δ ppm 2.78 (d, J=4.88 Hz, 3 H) 5.64 (s, 2 H) 6.64 (s, 1 H) 6.68 (dd, J=8.79, 2.44 Hz, 1 H) 6.72 (dd, J=8.30, 4.88 Hz, 1 H) 6.80 (m, 1 H) 6.92 (q, J=4.39 Hz, 1 H) 7.46 (dd, J=10.01, 2.69 Hz, 1 H) 9.34 (d, J=8.79 Hz, 1 H) 10.20 (s, 1 H); LR MS (EI): 296 ($M^+$).

Example 74

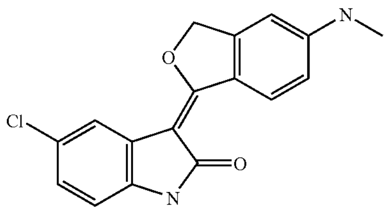

5-Chloro-3-(5-methylamino-3H-isobenzofuran-1-ylidene)-1,3-dihydro-indol-2-one $^1$H NMR (500 MHz, DMSO-$d_6$) δ ppm 2.78 (d, J=4.39 Hz, 3 H) 5.66 (s, 2 H) 6.65 (s, 1 H) 6.69 (m, 1 H) 6.76 (d, J=8.30 Hz, 1 H) 6.94 (m, 1 H) 7.01 (dd, J=8.30, 1.95 Hz, 1 H) 7.69 (d, J=2.44 Hz, 1 H) 9.33 (d, J=8.79 Hz, 1 H) 10.32 (s, 1 H); LR MS (EI): 312 ($M^+$) 314 (M+2).

Example 75

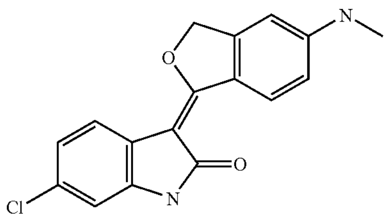

6-Chloro-3-(5-methylamino-3H-isobenzofuran-1-ylidene)-1,3-dihydro-indol-2-one $^1$H NMR (500 MHz, DMSO-$d_6$) δ ppm 2.78 (d, J=4.88 Hz, 3 H) 5.63 (s, 2 H) 6.64 (s, 1 H) 6.68 (dd, J=9.03, 2.20 Hz, 1 H) 6.76 (d, J=1.95 Hz, 1 H) 6.92 (m, 2 H) 7.69 (d, J=8.30 Hz, 1 H) 9.32 (d, J=8.79 Hz, 1 H) 10.34 (s, 1 H); LR MS (EI): 312 ($M^+$) 314 (M+2).

Example 76

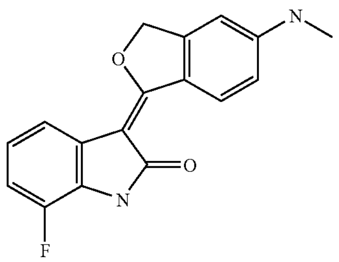

7-Fluoro-3-(5-methylamino-3H-isobenzofuran-1-ylidene)-1,3-dihydro-indol-2-one $^1$H NMR (500 MHz, DMSO-$d_6$) δ ppm 2.78 (d, J=4.88 Hz, 3 H) 5.64 (s, 2 H) 6.65 (s, 1 H) 6.69 (d, J=8.79 Hz, 1 H) 6.88 (m, 2 H) 6.93 (q, J=4.72 Hz, 1 H) 7.57 (m, 1 H) 9.36 (d, J=8.79 Hz, 1 H) 10.64 (s, 1 H); LR MS (E): 296 ($M^+$).

Preparation 7

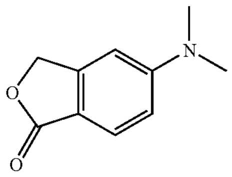

Preparation of 5-Dimethylamino-3H-isobenzofuran-1-one

To a stirred suspension of 5-aminophthalide (5.00 g, 33.5 mmol) in acetonitrile (120 ml), was added 37% formaldehyde aqueous solution (24.9 ml, 335 mmol) and sodium cyanoborohydride (8.42 g, 134 mmol). The mixture was cooled to 0° C., followed by addition of 10% AcOH aqueous solution (120 ml). The mixture was warmed to room temperature from 0° C. during 1.5 hour-period. The mixture was concentrated under reduced pressure to a smaller volume and was extracted with EtOAc (2×125 ml). The combined organic layers were washed with saturated $NaHCO_3$ solution (125 ml) and brine (125 ml), dried over $Na_2SO_4$. Removal of the solvent produced a crude product. Recrystallization of the crude product from MeOH gave 5-dimethylamino-3H-isobenzofuran-1-one as an off-white solid (3.90 g, 66%).

$^1$H NMR (500 MHz, DMSO-$D_6$) δ ppm 3.04 (s, 6 H) 5.23 (s, 2 H) 6.77 (s, 1 H) 6.85 (dd, J=8.79, 2.44 Hz, 1 H) 7.58 (d, J=8.79 Hz, 1 H).

Example 77

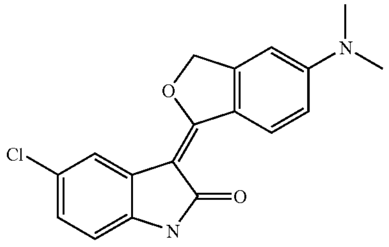

5-Chloro-3-(5-dimethylamino-3H-isobenzofuran-1-ylidene)-1,3-dihydro-indol-2-one

To a stirred solution of 5-chlorooxindole (1.18 g, 7.05 mmol) in anhydrous dimethoxyethane (20 ml) under nitrogen was added 2.5M n-BuLi solution in hexane (6.2 ml, 15.5 mmol). The mixture was stirred at room temperature for 10 minutes, and then 5-dimethylamino-3H-isobenzofuran-1-one (1.00 g, 5.64 mmol) was added. After stirred at room temperature for 3 hours, the mixture was poured into 0.5M HCl aqueous solution (80 ml) with stirring and then basified with NaOH aqueous solution. The solid was filtered, washed with water, and dried under vacuum to give a crude product. Trituration of the crude product with MeOH and EtOAc provided 5-chloro-3-(5-dimethylamino-3H-isobenzofuran-1-ylidene)-1,3-dihydro-indol-2-one as a yellow solid (0.90 g, 49%).

$^1$H NMR (500 MHz, DMSO-$d_6$) δ ppm 3.06 (s, 6 H) 5.69 (s, 2 H) 6.77 (d, J=8.30 Hz, 1 H) 6.86 (m, 2 H) 7.02 (dd, J=8.05, 2.20 Hz, 1 H) 7.70 (d, J=1.95 Hz, 1 H) 9.40 (m, J=9.28 Hz, 1 H) 10.34 (s, 1 H); LR MS (EI): 325 ($M^+$).

Example 78

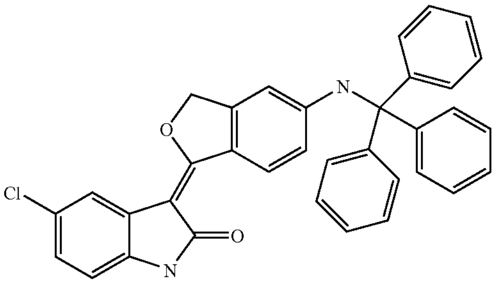

5-Chloro-3-[5-(trityl-amino)-3H-isobenzofuran-1-ylidene]-1,3-dihydro-indol-2-one A solution of 3-(5-Amino-3H-isobenzofuran-1-ylidene)-5-chloro-1,3-dihydro-indol-2-one (75 mg, 0.251 mmol), trityl chloride (84 mg, 0.301 mmol) and triethylamine (53 μμl, 0.377 mmol) in DMF (2.0 ml) was stirred at room temperature for 1.25 hours. The mixture was partitioned between EtOAc and water. The EtOAc layer was washed with brine, dried with $Na_2SO_4$ and rotary evaporated. The yellow solid was precipitated from $CHCl_3$ to give 5-chloro-3-[5-(trityl-amino)-3H-isobenzofuran-1-ylidene]-1,3-dihydro-indol-2-one as a bright yellow solid (61 mg, 45%).

$^1$H NMR (500 MHz, DMSO-D6) δ ppm 5.51 (s, 2 H) 6.57 (br s, 1 H) 6.72 (br s, 1 H) 6.75 (d, J=7.81 Hz, 1 H) 7.03 (dd, J=8.05, 2.20 Hz, 1 H) 7.25 (m, 3 H) 7.34 (m, 12 H) 7.65 (d, J=1.95 Hz, 1 H) 7.94 (s, 1 H) 9.07 (d, J=8.79 Hz, 1 H) 10.35 (s, 1 H).

Example 17

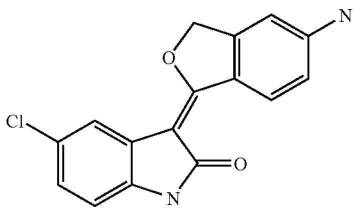

3-(5-Amino-3H-isobenzofuran-1-ylidene)-5-chloro-1,3-dihydro-indol-2-one

To a solution of 5-chloro-3-[5-(trityl-amino)-3H-isobenzofuran-1-ylidene]-1,3-dihydro-indol-2-one (200 mg, 0.37 mmol) in THF (4.0 ml) at room temperature was added 1.55M HCl/MeOH (0.5 ml). After stirring for 10 minutes, MeOH (3 ml) was added to the thick mixture, and then the resulting mixture was stirred for another 30 minutes. The precipitant was filtered, and rinsed with MEOH, $CHCl_3$, MeOH and then 30% EtOAc in hexane to give 3-(5-amino-3H-isobenzofuran-1-ylidene)-5-chloro-1,3-dihydro-indol-2-one as a bright yellow solid (79 mg, 72%).

$^1$H NMR (500 MHz, DMSO-D6) δ ppm 5.64 (s, 2 H) 6.39 (s, 2 H) 6.68 (m, 2 H) 6.77 (d, J=8.30 Hz, 1 H) 7.03 (dd, J=8.05, 2.20 Hz, 1 H) 7.70 (d, J=1.95 Hz, 1 H) 9.31 (m, 1 H) 10.34 (s, 1 H).

Preparation 8

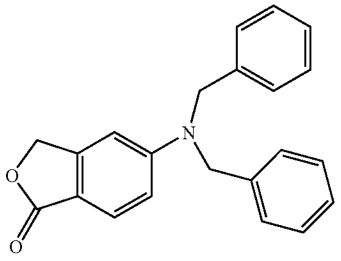

Preparation of 5-Dibenzylamino-3H-isobenzofuran-1-one

A mixture of 5-amino-2-benzofuran-1(3H)-one (100 mg, 0.67 mmol), benzyl bromide (319 μl, 2.68 mmol), and diisopropylethylamine (350 μl, 2.01 mmol) in THF (2.0 ml) was heated at 50° C. for 65 hours. The reaction was partitioned between water and EtOAc. The organic layer was washed with water, brine, dried with $Na_2SO_4$ and rotary evaporated. The yellow oil was triturated at room temperature with 10% EtOAc/hexane and then chromatographed (20% to 40% EtOAc/hexane gradient) to give 5-dibenzylamino-3H-isobenzofuran-1-one as a white solid (136 mg, 31%).

$^1$H NMR (500 MHz, $CDCl_3$) δ ppm 4.76 (s, 4 H) 5.12 (s, 2 H) 6.62 (d, J=1.46 Hz, 1 H) 6.84 (dd, J=8.79, 1.95 Hz, 1 H) 7.22 (m, 4 H) 7.30 (m, 2 H) 7.37 (m, 4 H) 7.67 (d, J=8.79 Hz, 1 H).

Example 79

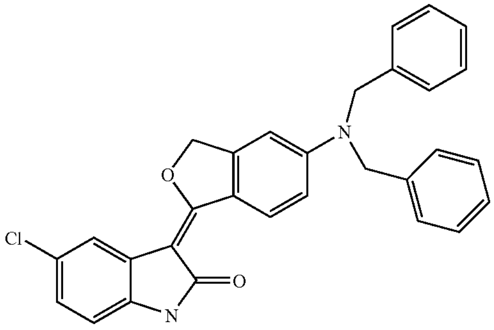

5-Chloro-3-(5-dibenzylamino-3H-isobenzofuran-1-ylidene)-1,3-dihydro-indol-2-one

To a solution of 5-chlorooxindole (63 mg, 0.371 mmol) in dimethoxyethane (2.0 ml) at room temperature was added 1.0M LiHMDS in THF (742 μl). After the mixture was stirred for 10 minutes at room temperature, 5-dibenzylamino-3H-isobenzofuran-1-one (110 mg, 0.334 mmol) was added, and the reaction was rapidly stirred at room temperature for 1.5 hours. The mixture was quenched into 4% HCl (20 ml), and then stirred with EtOAc. The mixture was basified with saturated $NaHCO_3$ aqueous solution. The organic layer was diluted with MeOH, followed by addition of HCl in MeOH to give a yellow precipitant. The yellow precipitant was separated, and rinsed with MeOH and 20% EtOAc/hexane to yield 5-chloro-3-(5-dibenzylamino-3H-isobenzofuran-1-ylidene)-1,3-dihydro-indol-2-one as a yellow solid (36 mg, 23%).

$^1$H NMR (500 MHz, DMSO-D6) δ ppm 4.87 (s, 4 H) 5.64 (s, 2 H) 6.77 (d, J=8.30 Hz, 1 H) 6.90 (m, 2 H) 7.04 (dd, J=8.06, 2.20 Hz, 1 H) 7.28 (m, 6 H) 7.36 (t, J=7.57 Hz, 4 H) 7.69 (d, J=1.95 Hz, 1 H) 9.34 (d, J=9.28 Hz, 1 H) 10.35 (s, 1 H).

Preparation 9

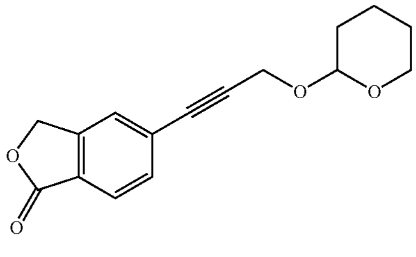

Preparation of 5-[3-(Tetrahydro-pyran-2-yloxy)-prop-1-ynyl]-3H-isobenzofuran-1-one To a mixture of 5-bromophthalide (2.00 g, 9.39 mmol), tetrahydro-2-(2-propynyloxy)-2H-pyran (5.3 ml, 37.6 mmol), copper(I) iodide (0.645 g, 3.39 mmol), triethylamine (1.90 g, 18.8 mmol) in DMF (20 ml), was added tetrakis (triphenylphosphine)palladium (1.30 g, 1.13 mmol). The mixture was heated at 65° C. under argon for 16 hours, cooled to room temperature and diluted with diethyl ether (250 ml). The filtrate was washed with brine (4×100 ml), dried over anhydrous $Na_2SO_4$, and concentrated to give a dark-reddish residue. Purification of the residue mixture by silica gel column chromatography, eluted with a gradient of EtOAc, led to 5-[3-(tetrahydro-pyran-2-yloxy)-prop-1-ynyl]-3H-isobenzofuran-1-one as a white solid (2.23 g, 87%).

$^1$H NMR (500 MHz, DMSO-$d_6$) δ ppm 1.50 (m, 4 H) 1.69 (m, 2 H) 3.49 (m, 1 H) 3.77 (m, 1 H) 4.50 (m, 2 H) 4.83 (m, 1 H) 5.40 (s, 2 H) 7.63 (d, J=6.83 Hz, 1 H) 7.77 (s, 1 H) 7.84 (d, J=7.81 Hz, 1 H); LR MS (EI): 272 ($M^+$).

Preparation 10

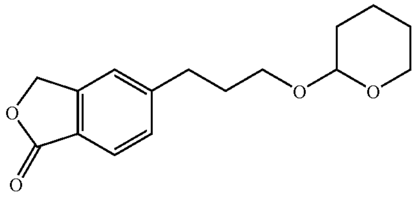

Preparation of 5-[3-(Tetrahydro-pyran-2-yloxy)-propyl]-3H-isobenzofuran-1-one

A mixture of 5-[3-(tetrahydro-pyran-2-yloxy)-prop-1-ynyl]-3H-isobenzofuran-1-one (1.0 g, 3.67 mmol) and 10% palladium on carbon (200 mg) in MeOH (15 ml) was shaken under 45 psi of hydrogen for 20 hours. The catalyst was removed by filtration through celite and rinsed with MeOH. The combined filtrates were evaporated to give 5-[3-(tetrahydro-pyran-2-yloxy)-propyl]-3H-isobenzofuran-1-one as a light yellow oil (1.0 g, 99%).

$^1$H NMR (500 MHz, DMSO-$d_6$) δ ppm 1.45 (m, 4 H) 1.61 (m, 1 H) 1.71 (m, 1 H) 1.88 (m, 2 H) 2.79 (m, 2 H) 3.38 (m, 2 H) 3.64 (m, 1 H) 3.72 (m, 1 H) 4.53 (t, J=3.42 Hz, 1 H) 5.37 (s, 2 H) 7.44 (d, J=7.81 Hz, 1 H) 7.51 (s, 1 H) 7.75 (d, J=7.81 Hz, 1 H); LR MS (EI): 276 ($M^+$).

Example 80

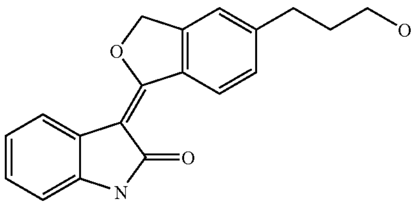

3-[5-(3-Hydroxy-propyl)-3H-isobenzofuran-1-ylidene]-1,3-dihydro-indol-2-one

To a stirred solution of oxindole (401 mg, 3.0 mmol) in anhydrous dimethoxyethane (20 ml) under nitrogen was added 1.0M LiHMDS/THF solution (6.3 ml, 6.3 mmol). The mixture was stirred at room temperature for 10 minutes, and 5-[3-(tetrahydro-pyran-2-yloxy)-propyl]-3H-isobenzofuran-1-one (500 mg, 1.81 mmol) was added. After stirred at room temperature for 2.5 hours, the mixture was poured into a mixture of THF (30 ml) and 2M HCl aqueous solution (30 ml) and heated at 65° C. for 1 hour. The mixture was cooled to room temperature, and then poured into an ice water (300 ml). The resulting solid was separated, rinsed with water, and dried to give 3-[5-(3-hydroxy-propyl)-3H-isobenzofuran-1-ylidene]-1,3-dihydro-indol-2-one as a yellow solid (460 mg, 83%).

$^1$H NMR (500 MHz, DMSO-$d_6$) δ ppm 1.77 (m, 2 H) 2.76 (m, 2 H) 3.45 (t, J=6.35 Hz, 2 H) 4.53 (brs, 1 H) 5.78 (s, 2 H) 6.82 (d, J=7.81 Hz, 1 H) 6.95 (t, J=7.57 Hz, 1 H) 7.10 (t, J=7.81 Hz, 1 H) 7.41 (d, J=8.30 Hz, 1 H) 7.48 (s, 1 H) 7.83 (d, J=7.81 Hz, 1 H) 9.55 (d, J=8.30 Hz, 1 H) 10.39 (s, 1 H).

Example 81

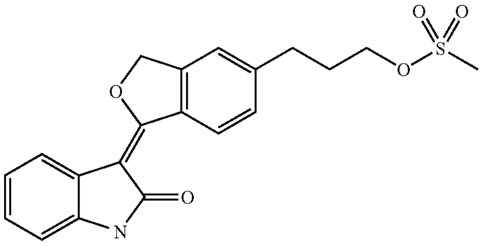

Methanesulfonic acid 3-[1-(2-oxo-1,2-dihydro-indol-3-ylidene)-1,3-dihydro-isobenzofuran-5-yl]-propyl ester To a stirred suspension of 3-[5-(3-hydroxy-propyl)-3H-isobenzofuran-1-ylidene]-1,3-dihydro-indol-2-one (440 mg, 1.43 mmol) and triethylamine (289 mg, 2.86 mmol) in THF (7 ml), was added methanesulfonyl chloride (327 mg, 2.86 mmol). The mixture was stirred for 20 minutes and poured into an ice water (150 ml, containing 0.5 ml of AcOH). The solid was filtered, washed with water and dried under vacuum to afford a crude product. The crude product was purified by silica gel column chromatography, eluted with 5% MeOH in $CHCl_3$, to give methanesulfonic acid 3-[1-(2-oxo-1,2-dihydro-indol-3-ylidene)-1,3-dihydro-isobenzofuran-5-yl]-propyl ester as a yellow solid (437 mg, 79%).

$^1$H NMR (500 MHz, DMSO-$d_6$) δ ppm 2.05 (m, 2 H) 2.84 (m, 2 H) 3.20 (s, 3 H) 4.24 (t, J=6.35 Hz, 2 H) 5.78 (s, 2 H) 6.82 (d, J=7.32 Hz, 1 H) 6.96 (t, J=7.57 Hz, 1 H) 7.10 (m, 1 H) 7.45 (d, J=8.30 Hz, 1 H) 7.53 (s, 1 H) 7.83 (d, J=7.81 Hz, 1 H) 9.57 (d, J=8.30 Hz, 1 H) 10.40 (s, 1 H).

Example 82

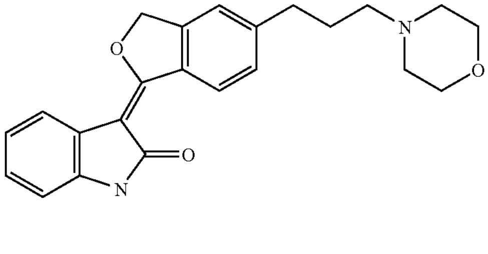

3-[5-(3-Morpholin-4-yl-propyl)-3H-isobenzofuran-1-ylidene]-1,3-dihydro-indol-2-one A mixture of methanesulfonic acid 3-[1-(2-oxo-1,2-dihydro-indol-3-ylidene)-1,3-dihydro-isobenzofuran-5-yl]-propyl ester (400 mg, 1.04 mmol) and morpholine (1.5 ml, 17.2 mmol) in DMF (5 ml) was heated at 90° C. for 1.5 hours. The mixture was cooled, and poured into water (125 ml) with stirring. The solid was filtered, washed with water and dried under vacuum to give 3-[5-(3-morpholin-4-yl-propyl)-3H-isobenzofuran-1-ylidene]-1,3-dihydro-indol-2-one as a yellow solid (385 mg, 98%).

$^1$H NMR (500 MHz, DMSO-$d_6$) δ ppm 1.78 (m, 2 H) 2.34 (brs, 6 H) 2.74 (m, 2 H) 3.57 (m, 4 H) 5.77 (s, 2 H) 6.82 (d, J=7.81 Hz, 1 H) 6.95 (m, 1 H) 7.10 (t, J=7.57 Hz, 1 H) 7.42 (d, J=7.81 Hz, 1 H) 7.50 (s, 1 H) 7.82 (d, J=7.32 Hz, 1 H) 9.54 (d, J=8.30 Hz, 1 H) 10.38 (s, 1 H).

The following Example 83 was prepared using the experiment procedure described in Example 82, but with the appropriate reagent, reaction conditions and reactant substitutions that will be readily realized by those of ordinary skill in this art without the exercise of undue experimentation.

Example 83

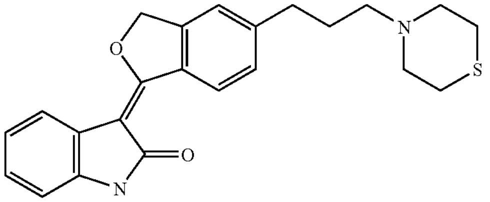

3-[5-(3-Thiomorpholin-4-yl-propyl)-3H-isobenzofuran-1-ylidene]-1,3-dihydro-indol-2-one $^1$H NMR (500 MHz, DMSO-$d_6$) δ ppm 1.79 (m, 2 H) 2.33 (t, J=7.08 Hz, 2 H) 2.60 (brs, 8 H) 2.72 (m, 2 H) 5.77 (s, 2 H) 6.82 (d, J=7.81 Hz, 1 H) 6.95 (t, J=7.08 Hz, 1 H) 7.10 (t, J=7.08 Hz, 1 H) 7.42 (d, J=8.30 Hz, 1 H) 7.49 (s, 1 H) 7.82 (d, J=7.32 Hz, 1 H) 9.54 (d, J=8.30 Hz, 1 H) 10.39 (s, 1 H).

Preparation 11

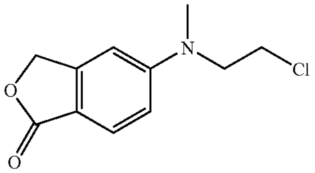

Preparation of 5-[(2-Chloro-ethyl)-methyl-amino]-3H-isobenzofuran-1-one

A mixture of 5-(2-chloro-ethylamino)-3H-isobenzofuran-1-one (3.0 g, 14.2 mmol), 37% formaldehyde aqueous solution (10 ml, 134 mmol) and sodium cyanoborohydride (3.6 g, 56.8 mmol) in a mixture of 10% AcOH aqueous solution (40 ml) and acetonitrile (40 ml) was stirred at 0° C. for 30 minutes. The mixture was allowed to warm to room temperature and was continuously stirred for 2 hours. The mixture was concentrated under reduced pressure, basified with 1M NaOH aqueous solution, and extracted with EtOAc (3×100 ml). The combined organic layers were washed with 1M NaOH aqueous solution (100 ml) and then water (2×100 ml), dried over anhydrous $Na_2SO_4$. Removal of the solvent led to a light yellow oil, which was crystallized with diethyl ether to produce 5-[(2-chloro-ethyl)-methyl-amino]-3H-isobenzofuran-1-one as a yellow solid (2.5 g, 78%).

$^1$H NMR (500 MHz, DMSO-$d_6$) δ ppm 3.07 (s, 3 H) 3.80 (m, 4 H) 5.23 (s, 2 H) 6.84 (d, J=1.95 Hz, 1 H) 6.91 (dd, J=8.79, 2.44 Hz, 1 H) 7.59 (d, J=8.30 Hz, 1 H).

Example 84

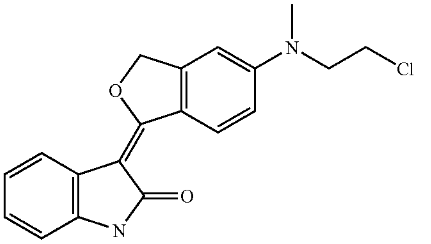

3-{5-[(2-Chloro-ethyl)-methyl-amino]-3H-isobenzofuran-1-ylidene}-1,3-dihydro-indol-2-one To a stirred solution of oxindole (0.739 g, 5.55 mmol) in anhydrous dimethoxyethane (10 ml) under nitrogen was added 1.0M LiHMDS/THF solution (14.0 ml, 14.0 mmol). The mixture was stirred at room temperature for 10 minutes, and 5-[(2-chloro-ethyl)-methyl-amino]-3H-isobenzofuran-1-one (1.0 g, 4.4 mmol) was added. The mixture was stirred at room temperature for 3 hours and was then poured into 1M HCl aqueous solution (300 ml) with stirring. The resulting mixture was heated at 40° C. for 30 minutes. The solid was filtered, washed with water and dried under vacuum to afford 3-{5-[(2-chloro-ethyl)-methyl-amino]-3H-isobenzofuran-1-ylidene}-1,3-dihydro-indol-2-one as a yellow solid (1.20 g, 79%).

$^1$H NMR (500 MHz, DMSO-$d_6$) δ ppm 3.10 (s, 3 H) 3.83 (m, 4 H) 5.67 (s, 2 H) 6.79 (d, J=7.32 Hz, 1 H) 6.92 (m, 3 H) 7.02 (t, J=7.08 Hz, 1 H) 7.76 (d, J=7.81 Hz, 1 H) 9.45 (d, J=8.79 Hz, 1 H) 10.23 (s, 1 H).

Example 85

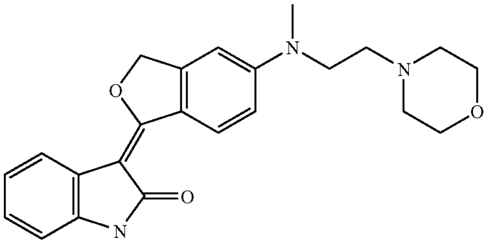

3-{5-[Methyl-(2-morpholin-4-yl-ethyl)-amino]-3H-isobenzofuran-1-ylidene}-1,3-dihydro-indol-2-one A mixture of 3-{5-[(2-chloro-ethyl)-methyl-amino]-3H-isobenzofuran-1-ylidene}-1,3-dihydro-indol-2-one (1.20 g, 3.52 mmol) and morpholine (3 ml, 34.4 mmol) in DMF (5 ml) was heated at 110° C. under nitrogen for 16 hours. The mixture was cooled to room temperature and was then poured into water (100 ml). The solid was filtered, washed with water and dried under vacuum to give a crude product. Purification of the crude product by silica gel column chromatography, eluted with a gradient of MeOH in $CHCl_3$, resulted in 3-{5-[methyl-(2-morpholin-4-yl-ethyl)-amino]-3H-isobenzofuran-1-ylidene}-1,3-dihydro-indol-2-one as a yellow solid (0.57 g, 41%).

$^1$H NMR (500 MHz, DMSO-$d_6$) δ ppm 2.44 (brs, 4 H) 2.48 (brs, 2 H) 3.06 (s, 3 H) 3.56 (t, J=4.39 Hz, 4 H) 3.60 (t, J=6.83 Hz, 2 H) 5.66 (s, 2 H) 6.78 (d, J=7.81 Hz, 1 H) 6.83 (s, 1 H) 6.88 (m, 2 H) 7.01 (m, 1 H) 7.75 (d, J=7.32 Hz, 1 H) 9.42 (d, J=8.79 Hz, 1 H) 10.21 (s, 1 H)

The following Example 86 was prepared using the experiment procedure described in Example 85, but with the appropriate reagent, reaction conditions and reactant substitutions that will be readily realized by those of ordinary skill in this art without the exercise of undue experimentation.

Example 86

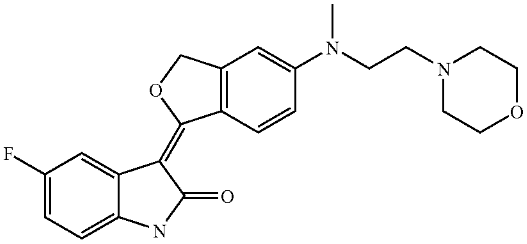

5-Fluoro-3-{5-[methyl-(2-morpholin-4-yl-ethyl)-amino]-3H-isobenzofuran-1-ylidene}-1,3-dihydro-indol-2-one $^1$H NMR (500 MHz, DMSO-$d_6$) δ ppm 2.45 (brs, 4 H) 2.48 (brs, 2 H) 3.07 (s, 3 H) 3.56 (t, J=3.91 Hz, 4 H) 3.61 (t, J=6.83 Hz, 2 H) 5.69 (s, 2 H) 6.74 (dd, J=8.54, 4.64 Hz, 1 H) 6.85 (m, 3 H) 7.50 (m, 1 H) 9.41 (d, J=8.79 Hz, 1 H) 10.24 (s, 1 H).

Example 87

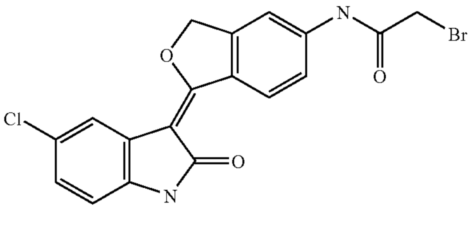

2-Bromo-N-[1-(5-chloro-2-oxo-1,2-dihydro-indol-3-ylidene)-1,3-dihydro-isobenzofuran-5-yl]-acetamide A mixture of 3-(5-amino-3H-isobenzofuran-1-ylidene)-5-chloro-1,3-dihydro-indol-2-one (300 mg, 1.00 mmol), bromoacetic anhydride (350 mg, 1.35 mmol) and potassium carbonate (138 mg, 1.0 mmol) in THF (10 ml) was stirred at 50° C. for 2 hours. The mixture was poured into water (100 ml). The resulting solid was filtered, washed with water, and dried under vacuum to give 2-bromo-N-[1-(5-chloro-2-oxo- 1,2-dihydro-indol-3-ylidene)-1,3-dihydro-isobenzofuran-5-yl]-acetamide as a brown solid (380 mg, 91%).

Example 88

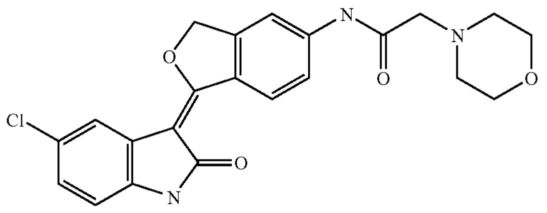

N-[1-(5-Chloro-2-oxo-1,2-dihydro-indol-3-ylidene)-1,3-dihydro-isobenzofuran-5-yl]-2-morpholin-4-yl-acetamide A mixture of 2-bromo-N-[1-(5-chloro-2-oxo-1,2-dihydro-indol-3-ylidene)-1,3-dihydro-isobenzofuran-5-yl]-acetamide (81 mg, 0.19 mmol) in morpholine (2 ml) was stirred at 50° C. under nitrogen for 50 minutes, and was then poured into water (75 ml). The solid was filtered, washed with water, and dried under vacuum to give [1-(5-chloro-2-oxo-1,2-dihydro-indol-3-ylidene)-1,3-dihydro-isobenzofuran-5-yl]-2-morpholin-4-yl-acetamide as a yellow solid (67 mg, 82%); LR MS (FAB+): 426 (M+1) 428 (M+3).

The following Example 89 through 92 were prepared using the experiment procedure described in Example 88, but with the appropriate reagent, reaction conditions and reactant substitutions that will be readily realized by those of ordinary skill in this art without the exercise of undue experimentation Example 89

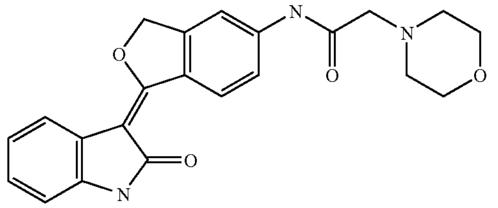

2-Morpholin-4-yl-N-[1-(2-oxo-1,2-dihydro-indol-3-ylidene)-1,3-dihydro-isobenzofuran-5-yl]-acetamide $^1$H NMR (500 MHz, DMSO-$d_6$) δ ppm 2.53 (t, J=4.39 Hz, 4 H) 3.21 (s, 2 H) 3.65 (t, J=4.60 Hz, 4 H) 5.78 (s, 2 H) 6.82 (d, J=7.32 Hz, 1 H) 6.95 (t, J=7.08 Hz, 1 H) 7.09 (t, J=7.08 Hz, 1 H) 7.65 (dd, J=8.79, 1.95 Hz, 1 H) 7.80 (d, J=7.32 Hz, 1 H) 8.12 (s, 1 H) 9.56 (d, J=8.79 Hz, 1 H) 10.22 (s, 1 H) 10.38 (s, 1 H); LR MS (FAB+): 392 (M+1).

Example 90

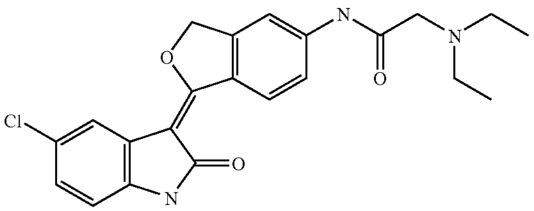

N-[1-(5-Chloro-2-oxo-1,2-dihydro-indol-3-ylidene)-1,3-dihydro-isobenzofuran-5-yl]-C-diethylamino-acetamide

LR MS (FAB+): 412 (M+1) 414 (M+3).

Example 91

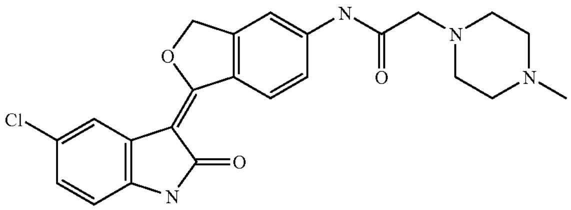

N-[1-(5-Chloro-2-oxo-1,2-dihydro-indol-3-ylidene)-1,3-dihydro-isobenzofuran-5-yl]-2-(4-methyl-piperazin-1-yl)-acetamide $^1$H NMR (500 MHz, DMSO-$d_6$) δ ppm 2.17 (s, 3 H) 2.38 (brs, 4 H) 2.53 (brs, 4 H) 3.18 (s, 2 H) 5.82 (s, 2 H) 6.82 (d, J=7.81 Hz, 1 H) 7.12 (dd, J=8.06, 2.20 Hz, 1 H) 7.66 (d, J=8.30 Hz, 1 H) 7.76 (s, 1 H) 8.13 (s, 1 H) 9.53 (d, J=8.79 Hz, 1 H) 10.20 (s, 1 H) 10.52 (s, 1 H); LR MS (FAB+): 439 (M+1) 441 (M+3).

Example 92

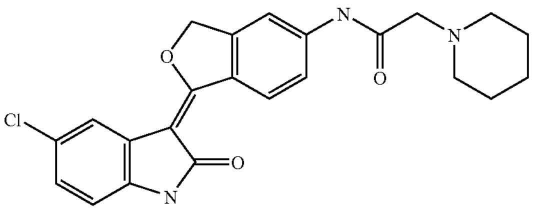

N-[1-(5-Chloro-2-oxo-1,2-dihydro-indol-3-ylidene)-1,3-dihydro-isobenzofuran-5-yl]-2-piperidin-1-yl-acetamide $^1$H NMR (500 MHz, DMSO-$d_6$) δ ppm 1.41 (br, 2 H) 1.57 (m, 4 H) 2.47 (br, 4 H) 3.14 (s, 2 H) 5.82 (s, 2 H) 6.82 (d, J=8.30 Hz, 1 H) 7.12 (dd, J=8.30, 1.95 Hz, 1 H) 7.67 (dd, J=8.79, 1.95 Hz, 1 H) 7.76 (d, J=2.44 Hz, 1 H) 8.14 (s, 1 H) 9.53 (d, J=8.79 Hz, 1 H) 10.17 (s, 1 H) 10.52 (s, 1 H); LR MS (FAB+): 424 (M+1).

Example 93

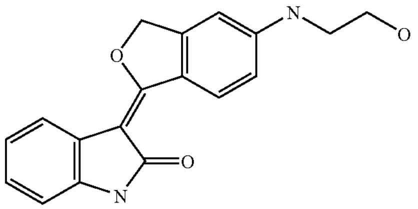

3-[5-(2-Hydroxy-ethylamino)-3H-isobenzofuran-1-ylidene]-1,3-dihydro-indol-2-one $^1$H NMR (500 MHz, DMSO-$d_6$) δ ppm 3.23 (q, J=5.86 Hz, 2 H) 3.59 (q, J=5.70 Hz, 2 H) 4.79 (t, J=5.61 Hz, 1 H) 5.63 (s, 2 H) 6.77 (m, 4 H) 6.89 (t, J=7.57 Hz, 1 H) 7.01 (t, J=7.57 Hz, 1 H) 7.74 (d, J=7.81 Hz, 1 H) 9.36 (d, J=9.28 Hz, 1 H) 10.20 (s, 1 H).

Example 94

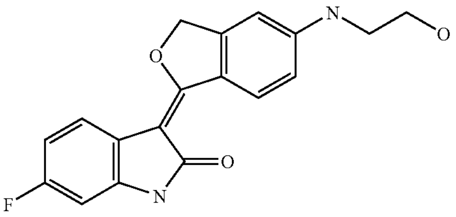

6-Fluoro-3-[5-(2-hydroxy-ethylamino)-3H-isobenzofuran-1-ylidene]-1,3-dihydro-indol-2-one 6-Fluoro-3-[5-(2-hydroxy-ethylamino)-3H-isobenzofuran-1-ylidene]-1,3-dihydro-indol-2-one was obtained as the minor product in the preparation of 3-[5-(2-Chloro-ethylamino)-3H-isobenzofuran-1-ylidene]-5-fluoro-1,3-dihydro-indol-2-one (Example 46).

$^1$H NMR (500 MHz, DMSO-$d_6$) δ ppm 3.23 (q, J=5.86 Hz, 2 H) 3.59 (q, J=5.86 Hz, 2 H) 4.79 (t, J=5.37 Hz, 1 H) 5.63 (s, 2 H) 6.59 (dd, J=9.28, 2.44 Hz, 1 H) 6.72 (m, 3 H) 6.83 (t, J=5.37 Hz, 1 H) 7.70 (dd, J=8.30, 5.86 Hz, 1 H) 9.31 (d, J=8.79 Hz, 1 H) 10.35 (s, 1 H); LR MS (FAB+): 327 (M+1).

Example 95

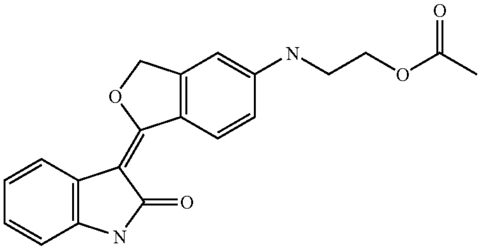

Acetic acid 2-[1-(2-oxo-1,2-dihydro-indol-3-ylidene)-1,3-dihydro-isobenzofuran-5-ylamino]-ethyl ester To a stirred mixture of 3-[5-(2-hydroxy-ethylamino)-3H-isobenzofuran-1-ylidene]-1,3-dihydro-indol-2-one (50 mg, 0.16 mmol) and acetic anhydride (20 mg, 0.20 mmol) in THF (3 ml), was added 4-dimethylaminopyridine (10 mg, 0.08 mmol). The mixture was stirred for 30 minutes and was then poured into water (75 ml). The solid was filtered, washed with water and dried under vacuum to give acetic acid 2-[1-(2-oxo-1,2-dihydro-indol-3-ylidene)-1,3-dihydro-isobenzofuran-5-ylamino]-ethyl ester as a yellow solid (39 mg, 68%).

$^1$H NMR (500 MHz, DMSO-$d_6$) δ ppm 2.03 (s, 3 H) 3.43 (q, J=5.70 Hz, 2 H) 4.18 (t, J=5.61 Hz, 2 H) 5.64 (s, 2 H) 6.77 (m, 3 H) 6.90 (t, J=7.08 Hz, 1 H) 6.95 (t, J=5.61 Hz, 1 H) 7.01 (m, 1 H) 7.75 (d, J=7.32 Hz, 1 H) 9.38 (d, J=8.79 Hz, 1 H) 10.21 (s, 1 H).

The following Example 96 was prepared using the experiment procedure described in Example 95, but with the appropriate reagent, reaction conditions and reactant substitutions that will be readily realized by those of ordinary skill in this art without the exercise of undue experimentation.

Example 96

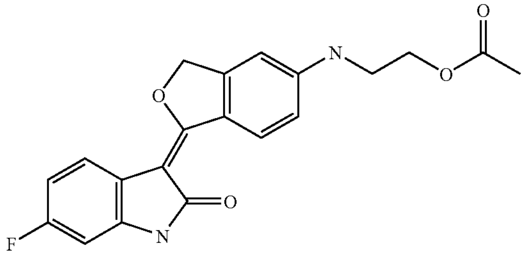

Acetic acid 2-[1-(6-fluoro-2-oxo-1,2-dihydro-indol-3-ylidene)-1,3-dihydro-isobenzofuran-5-ylamino]-ethyl ester $^1$H NMR (500 MHz, DMSO-$d_6$) δ ppm 2.03 (s, 3 H) 3.43 (q, J=5.86 Hz, 2 H) 4.17 (t, J=5.61 Hz, 2 H) 5.64 (s, 2 H) 6.59 (dd, J=9.28, 2.44 Hz, 1 H) 6.73 (m, 3 H) 6.97 (t, J=5.61 Hz, 1 H) 7.71 (dd, J=8.30, 5.86 Hz, 1 H) 9.32 (d, J=8.79 Hz, 1 H) 10.37 (s, 1 H); LR MS (FAB+): 369 (M+1).

Example 97

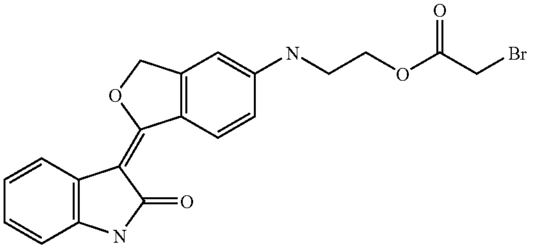

Bromo-acetic acid 2-1-(2-oxo-1,2-dihydro-indol-3-ylidene)-1,3-dihydro-isobenzofuran-5-ylamino]-ethyl ester To a stirred suspension of 3-[5-(2-hydroxy-ethylamino)-3H-isobenzofuran-1-ylidene]-1,3-dihydro-indol-2-one (100 mg, 0.324 mmol) and bromoacetic anhydride (126 mg, 0.486 mmol) in THF (3 ml), was added 4-dimethylaminopyridine (10 mg, 0.082 mmol). The mixture was stirred at room temperature for 1 hour and then poured into water (75 ml). The solid was filtered, washed with water and dried under vacuum to give bromo-acetic acid 2-[1-(2-oxo-1,2-dihydro-indol-3-ylidene)-1,3-dihydro-isobenzofuran-5-ylamino]-ethyl ester as a yellow solid (108 mg, 78%).

$^1$H NMR (300 MHz, DMSO-$d_6$) δ ppm 3.46 (m, 2 H) 4.17 (s, 2 H) 4.29 (t, J=5.42 Hz, 2 H) 5.64 (s, 2 H) 6.77 (m, 3 H) 6.91 (m, 2 H) 7.02 (m, 1 H) 7.75 (d, J=7.62 Hz, 1 H) 9.38 (d, J=9.67 Hz, 1 H) 10.21 (s, 1 H); LR MS (CI+): 429 (M+1) 431 (M+3).

Example 98

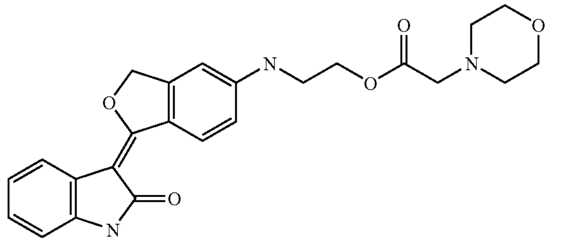

Morpholin-4-yl-acetic acid 2-[1-(2-oxo-1,2-dihydro-indol-3-ylidene)-1,3-dihydro-isobenzofuran-5-ylamino]-ethyl ester A mixture of bromo-acetic acid 2-[1-(2-oxo-1,2-dihydro-indol-3-ylidene)-1,3-dihydro-isobenzofuran-5-ylamino]-ethyl ester (35 mg, 0.082 mmol) in morpholine (1 ml) was stirred at room temperature for 1.5 hours. The mixture was poured into 2% AcOH aqueous solution (50 ml) with stirring. The mixture was then basified with NaOH solution. The solid was filtered, washed with water, dried under vacuum to give morpholin-4-yl-acetic acid 2-[1-(2-oxo-1,2-dihydro-indol-3-ylidene)-1,3-dihydro-isobenzofuran-5-ylamino]-ethyl ester as a yellow solid (18 mg, 51%).

$^1$H NMR (300 MHz, DMSO-$d_6$) δ ppm 2.47 (m, 4 H) 3.23 (s, 2 H) 3.45 (m, 2 H) 3.55 (m, 4 H) 4.23 (t, J=5.42 Hz, 2 H) 5.64 (s, 2 H) 6.77 (m, 3 H) 6.90 (m, 2 H) 7.01 (m, 1 H) 7.75 (d, J=7.04 Hz, 1 H) 9.38 (d, J=9.09 Hz, 1 H) 10.21 (s, 1 H); LR MS (CI+): 436 (M+1).

The following Example 99 through 101 were prepared using the experiment procedure described in Example 98, but with the appropriate reagent, reaction conditions and reactant substitutions that will be readily realized by those of ordinary skill in this art without the exercise of undue experimentation.

Example 99

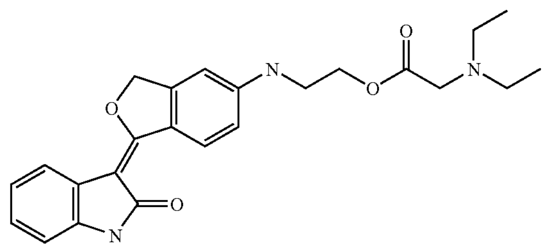

Diethylamino-acetic acid 2-[1-(2-oxo-1,2-dihydro-indol-3-ylidene)-1,3-dihydro-isobenzofuran-5-ylamino]-ethyl ester $^1$H NMR (300 MHz, DMSO-$d_6$) δ ppm 0.93 (t, J=7.18 Hz, 6 H) 2.56 (q, J=7.04 Hz, 4 H) 3.31 (s, 2H) 3.44 (q, J=5.28 Hz, 2 H) 4.21 (t, J=5.42 Hz, 2 H) 5.64 (s, 2 H) 6.77 (m, 3 H) 6.91 (m, 2 H) 7.01 (m, 1 H) 7.75 (d, J=7.04 Hz, 1 H) 9.38 (d, J=9.38 Hz, 1 H) 10.21 (s, 1 H).

Example 100

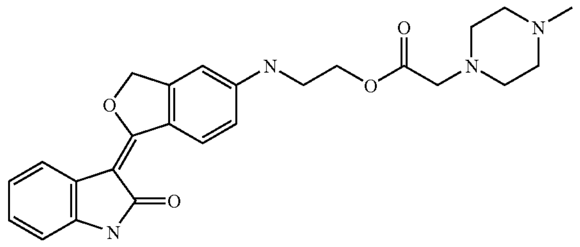

(4-Methyl-piperazin-1-yl)-acetic acid 2-[1-(2-oxo-1,2-dihydro-indol-3-ylidene)-1,3-dihydro-isobenzofuran-5-ylamino]-ethyl ester $^1$H NMR (300 MHz, DMSO-$d_6$) δ ppm 2.14 (s, 3 H) 2.30 (brs, 4 H) 2.47 (br, 4 H) 3.21 (s, 2 H) 3.44 (q, J=5.28 Hz, 2 H) 4.22 (t, J=5.57 Hz, 2 H) 5.64 (s, 2 H) 6.77 (m, 3 H) 6.90 (m, 2 H) 7.02 (t, J=7.48 Hz, 1 H) 7.75 (d, J=7.92 Hz, 1 H) 9.38 (d, J=8.79 Hz, 1 H) 10.21 (s, 1 H).

Example 101

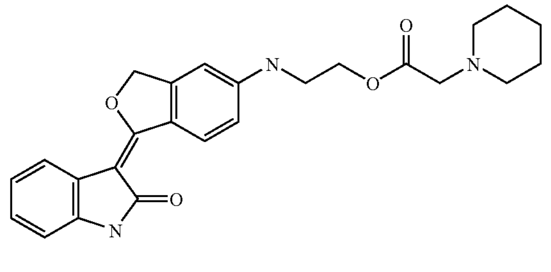

Piperidin-1-yl-acetic acid 2-[1-(2-oxo-1,2-dihydro-indol-3-ylidene)-1,3-dihydro-isobenzofuran-5-ylamino]-ethyl ester $^1$H NMR (300 MHz, DMSO-$d_6$) δ ppm 1.34 (m, 2 H) 1.46 (m, 4 H) 2.42 (m, 4 H) 3.17 (s, 2 H) 3.44 (q, J=5.57 Hz, 2 H) 4.21 (t, J=5.42 Hz, 2 H) 5.64 (s, 2 H) 6.77 (m, 3 H) 6.91 (m, 2 H) 7.02 (t, J=7.04 Hz, 1 H) 7.75 (d, J=7.33 Hz, 1 H) 9.38 (d, J=8.79 Hz, 1 H) 10.21 (s, 1 H).

Preparation 12

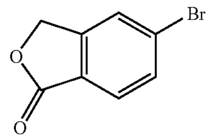

Preparation of 5-Bromophthalide

The preparation of 5-bromophthalide is described in the literature (Safaer Hayat, Atta-ur-Rahman, M. Iqbal Choudhary, Khalid Mohammed Khan and Ernst Bayer Tetrahedron Letters, 42(2001) 1647–1649).

$^1$H NMR (500 MHz, $CDCl_3$) δ ppm 5.30 (s, 2 H) 7.68 (m, 2 H) 7.79 (d, J=8.79 Hz, 1 H).

Example 102

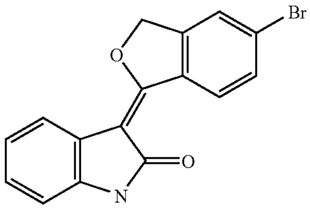

3-(5-Bromo-3H-isobenzofuran-1-ylidene)-1,3-dihydro-indol-2-one

To a stirred solution of oxindole (3.13 g, 23.5 mmol) in anhydrous dimethoxyethane (20 ml) under nitrogen was added 1.0M LiHMDS/THF solution (49 ml, 49 mmol). The mixture was stirred at room temperature for 10 minutes, and 5-bromophthalide (3.00 g, 14.1 mmol) was added. The reaction mixture was stirred at room temperature for 3 hours and then poured into a mixture of THF (50 ml) and 2M HCl aqueous solution (50 ml). After heated at reflux for 1 hour and then cooled to room temperature, the resulting mixture was poured into water (100 ml). The resulting solid was filtered, washed with water and dried under vacuum to give 3-(5-bromo-3H-isobenzofuran-1-ylidene)-1,3-dihydro-indol-2-one as a yellow solid (3.57 g, 77%).

$^1$H NMR (500 MHz, DMSO-$d_6$) δ ppm 5.80 (s, 2 H) 6.83 (d, J=7.81 Hz, 1 H) 6.97 (td, J=7.69, 1.22 Hz, 1 H) 7.13 (td, J=7.69, 1.22 Hz, 1 H) 7.79 (dd, J=8.30, 1.95 Hz, 1 H) 7.83 (d, J=7.32 Hz, 1 H) 7.92 (s, 1 H) 9.58 (d, J=8.30 Hz, 1 H) 10.48 (s, 1 H).

Example 103

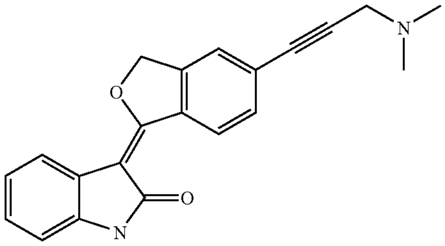

3-[5-(3-Dimethylamino-prop-1-ynyl)-3H-isobenzofuran-1-ylidene]-1,3-dihydro-indol-2-one To a mixture of 3-(5-bromo-3H-isobenzofuran-1-ylidene)-1,3-dihydro-indol-2-one (467 mg, 1.42 mmol), 1-dimethylamino-2-propyne (473 mg, 5.69 mmol), copper (I) iodide (48 mg, 0.25 mmol), triethylamine (287 mg, 2.84 mmol) in DMF (5 ml), was added tetrakis(triphenylphosphine)palladium (100 mg, 0.086 mmol). The mixture was heated at 65° C. under argon for 16 hours, and then cooled to room temperature. The mixture was diluted with MeOH (100 ml). The insoluble material was removed by filtration, and the filtrate solution was concentrated and then diluted with EtOAc (200 ml). The resulting mixture was washed with brine (3×100 ml), dried over anhydrous $Na_2SO_4$, and concentrated to give a dark-brown residue. Purification of the residue by silica gel column chromatography, eluted with a gradient of MeOH in $CHCl_3$, afforded 3-[5-(3-dimethylamino-prop-1-ynyl)-3H-isobenzofuran-1-ylidene]-1,3-dihydro-indol-2-one as a brown solid (320 mg, 68%).

$^1$H NMR (500 MHz, DMSO-$d_6$) δ ppm 2.27 (s, 6 H) 3.53 (s, 2 H) 5.78 (s, 2 H) 6.82 (d, J=7.32 Hz, 1 H) 6.96 (t, J=7.57 Hz, 1 H) 7.12 (t, J=7.08 Hz, 1 H) 7.62 (d, J=8.30 Hz, 1 H) 7.71 (s, 1 H) 7.83 (d, J=7.32 Hz, 1 H) 9.63 (d, J=8.30 Hz, 1 H) 10.46 (s, 1 H).

Example 104

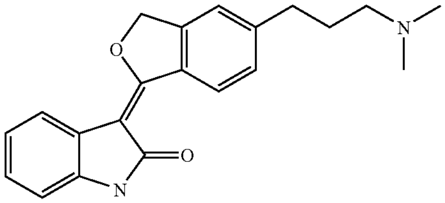

3-[5-(3-Dimethylamino-propyl)-3H-isobenzofuran-1-ylidene]-1,3-dihydro-indol-2-one A mixture of 3-[5-(3-dimethylamino-prop-1-ynyl)-3H-isobenzofuran-1-ylidene]-1,3-dihydro-indol-2-one (300 mg, 0.91 mmol) and 10% palladium on carbon (60 mg) in MeOH (20 ml) was shaken under 43 psi of hydrogen for 4 hours. The catalyst was removed by filtration through celite and rinsed with MeOH. The combined filtrates were evaporated to give a crude product. The crude product was purified by silica gel column chromatography, eluted with a gradient of MeOH in $CHCl_3$, to give 3-[5-(3-dimethylamino-propyl)-3H-isobenzofuran-1-ylidene]-1,3-dihydro-indol-2-one as a yellow solid (70 mg, 23%).

$^1$H NMR (500 MHz, DMSO-$d_6$) δ ppm 2.02 (m, 2 H) 2.78 (m, 8 H) 3.06 (m, 2 H) 5.80 (s, 2 H) 6.83 (d, J=7.32 Hz, 1 H) 6.96 (t, J=7.57 Hz, 1 H) 7.11 (t, J=7.08 Hz, 1 H) 7.46 (d, J=8.30 Hz, 1 H) 7.53 (s, 1 H) 7.83 (d, J=7.32 Hz, 1 H) 9.59 (d, J=8.30 Hz, 1 H) 10.41 (s, 1 H).

Example 105

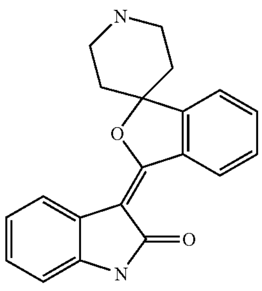

(3E)-3-(3H-spiro[2-benzofuran-1,4'-piperidin]-3-ylidene)-1,3-dihydro-2H-indol-2-one To a stirred solution of oxindole (139 mg, 1.04 mmol) in anhydrous DMF (5 ml) under nitrogen was added 1.0M LiHMDS/THF solution (6.0 ml, 6.0 mmol). The mixture was stirred at room temperature for 10 minutes, and then 4-spiro-[3-phthalide]piperidine hydrochloride (200 mg, 0.83 mmol) was added. The mixture was stirred at room temperature for 2.5 hours and then poured into 0.5M HCl (40 ml) with stirring. The mixture was basified with NaOH aqueous solution and extracted with $CHCl_3$ (2×100 ml). The combined organic layers were washed with water (2×100 ml), dried over anhydrous $Na_2SO_4$ and evaporated to give a crude product. Purification of the crude product by silica gel column chromatography, eluted with a gradient of MeOH in $CHCl_3$, produce the example 116 as a yellow solid (86 mg, 22%).

$^1$H NMR (500 MHz, DMSO-$d_6$) δ ppm 1.59 (d, J=13.18 Hz, 2 H) 2.10 (m, 2 H) 3.04 (m, 4 H) 6.83 (d, J=7.81 Hz, 1 H) 7.01 (t, J=7.57 Hz, 1 H) 7.12 (t, J=7.57 Hz, 1 H) 7.57 (m, 2 H) 7.65 (t, J=7.32 Hz, 1 H) 7.88 (d, J=7.32 Hz, 1 H) 9.61 (d, J=7.81 Hz, 1 H) 10.42 (s, 1 H); LRMS (EI): 318 ($M^+$).

Example 106

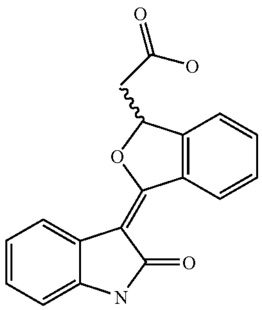

[3-(2-Oxo-1,2-dihydro-indol-3-ylidene)-1,3-dihydro-isobenzofuran-1-yl]-acetic acid To a solution of oxindole (0.400 g, 3.0 mmol) in DME (8.0 mL) was added 9.0 mL LHMDS (1.0 M in THF). After stirring at room temperature for 10 min, phthalide-3-acetic acid (0.519 g, 2.7 mmol) was added as a solid in one portion. The mixture was rapidly stirred for 3.5 h and then quenched into 4% HCl aqueous solution (100 mL) to give a yellow solid. The solid was filtered, rinsed with $H_2O$, MeOH and then 6:4/hexane:EtOAc to afford (0.105 g, 13%) of product as a yellow solid.

$^1$H NMR (500 MHz, DMSO-D6) δ ppm 2.73 (dd, J=16.60, 9.28 Hz, 1 H) 3.30 (dd, J=16.60, 3.42 Hz, 1 H) 6.24 (dd, J=9.03, 3.66 Hz, 1 H) 6.83 (d, J=7.81 Hz, 1 H) 6.93 (td, J=7.57, 0.98 Hz, 1 H) 7.12 (td, J=7.57, 0.98 Hz, 1 H) 7.59 (m, 1 H) 7.68 (m, 2 H) 7.80 (d, J=7.32 Hz, 1 H) 9.62 (d, J=8.30 Hz, 1 H) 10.44 (s, 1 H) 12.68 (s, 1 H).

The following Example 107 through 108 were prepared using the experiment procedure described in Example 106, but with the appropriate reagent, reaction conditions and reactant substitutions that will be readily realized by those of ordinary skill in this art without the exercise of undue experimentation Example 107

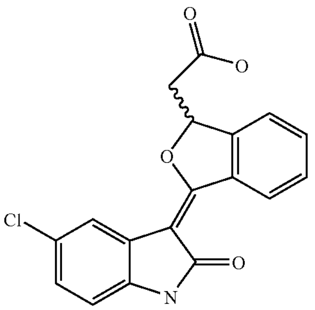

[3-(5-Chloro-2-oxo-1,2-dihydro-indol-3-ylidene)-1,3-dihydro-isobenzofuran-1-yl]-acetic acid $^1$H NMR (500 MHz, DMSO-D6) δ ppm 2.77 (dd, J=17.09, 9.28 Hz, 1 H) 3.31 (obsc dd, J=3.42 Hz, 1 H) 6.28 (dd, J=9.03, 3.66 Hz, 1 H) 6.83 (d, J=8.30 Hz, 1 H) 7.16 (dd, J=8.30, 2.44 Hz, 1 H) 7.61 (m, 1 H) 7.70 (m, 2 H) 7.80 (d, J=1.95 Hz, 1 H) 9.60 (d, J=7.81 Hz, 1 H) 10.58 (s, 1 H) 12.74 (s, 1 H).

Example 108

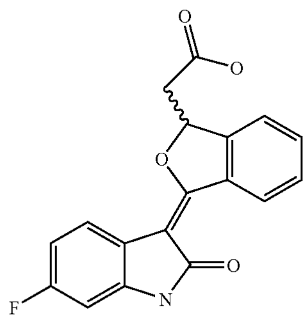

[3-(6-Fluoro-2-oxo-1,2-dihydro-indol-3-ylidene)-1,3-dihydro-isobenzofuran-1-yl]-acetic acid $^1$H NMR (500 MHz, DMSO-D6) δ ppm 2.74 (dd, J=16.60, 9.28 Hz, 1 H) 3.29 (dd, J=16.60, 3.91 Hz, 1 H) 6.24 (dd, J=9.03, 3.66 Hz, 1 H) 6.65 (dd, J=9.28, 1.46 Hz, 1 H) 6.75 (m, 1 H) 7.59 (t, J=7.32 Hz, 1 H) 7.68 (m, 2 H) 7.77 (dd, J=8.05, 6.10 Hz, 1 H) 9.56 (d, J=8.30 Hz, 1 H) 10.60 (s, 1 H) 12.68 (s, 1 H).

Example 109

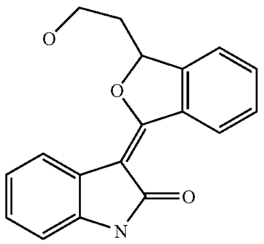

3-[3-(2-Hydroxy-ethyl)-3H-isobenzofuran-1-ylidene]-1,3-dihydro-indol-2-one

To a solution of [3-(2-oxo-1,2-dihydro-indol-3-ylidene)-1,3-dihydro-isobenzofuran-1-yl]-acetic acid (1.00 g, 3.25 mmol) in dioxane (100 ml) at room temperature was added dropwise 1.0M borane/THF (14.3 ml). The reaction was stirred at room temperature for 15 minutes, then heated at 65° C. for 10 minutes, and then cooled to room temperature. An additional 1.0M borane/THF (2.0 ml) was added and the mixture was heated at 65° C. for 5 minutes. Upon cooling the reaction was quenched with 4% HCl aqueous solution and then extracted with EtOAc. The combined organic layers were washed with saturated $NaHCO_3$ aqueous solution, brine, dried over anhydrous $Na_2SO_4$, and rotary evaporated to provide a yellow film. The yellow film was recrystallized from $CHCl_3$/hexane to give a pure yellow solid (0.466 g). The filtrate was chromatographed with 2% MeOH in $CHCl_3$ and then recrystallized from 1,2-dichloroethane/hexane to give an additional 0.064 g for a combined yield of 3-[3-(2-hydroxy-ethyl)-3H-isobenzofuran-1-ylidene]-1,3-dihydro-indol-2-one as a yellow solid (0.53 g, 56%).

$^1$H NMR (500 MHz, DMSO-D6) δ ppm 1.81 (m, 1 H) 2.31 (m, 1 H) 3.73 (m, 1 H) 3.82 (m, 1 H) 4.88 (t, J=5.13 Hz, 1 H) 6.06 (dd, J=9.52, 3.17 Hz, 1 H) 6.83 (d, J=7.81 Hz, 1 H) 6.98 (t, J=7.57 Hz, 1 H) 7.12 (m, 1 H) 7.58 (m, 1 H) 7.66 (m, 2 H) 7.84 (d, J=7.32 Hz, 1 H) 9.64 (d, J=8.30 Hz, 1 H) 10.43 (s, 1 H).

Example 110

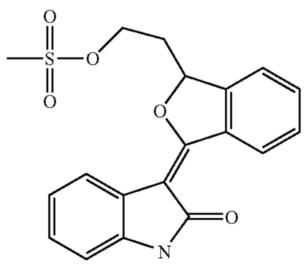

Methanesulfonic acid 2-[3-(2-oxo-1,2-dihydro-indol-3-ylidene)-1,3-dihydro-isobenzofuran-1-yl]-ethyl ester To a mixture of 3-[3-(2-hydroxy-ethyl)-3H-isobenzofuran-1-ylidene]-1,3-dihydro-indol-2-one (0.50 g, 1.71 mmol) and triethylamine (356 μμl, 2.557 mmol) in 1,2-dichloroethane (23 ml) cooled to 0° C. was added methanesulfonyl chloride (145 μl, 1.88 mmol). After 20 minutes at 0° C. the reaction was partitioned between 0.5% HCl aqueous solution and EtOAc. The organic layer was then washed with water, brine, dried with anhydrous $Na_2SO_4$ Removal of the solvent led to methanesulfonic acid 2-[3-(2-oxo-1,2-dihydro-indol-3-ylidene)-1,3-dihydro-isobenzofuran-1-yl]-ethyl ester as a yellow solid (0.502 g, 79%).

$^1$H NMR (500 MHz, DMSO-D6) δ ppm 2.14 (m, 1 H) 2.66 (m, 1 H) 3.23 (s, 3 H) 4.48 (m, 1 H) 4.55 (m, 1 H) 6.09 (dd, J=9.28, 2.93 Hz, 1 H) 6.83 (d, J=7.81 Hz, 1 H) 6.96 (m, 1 H) 7.13 (td, J=7.57, 0.98 Hz, 1 H) 7.60 (m, 1 H) 7.69 (m, 2 H) 7.89 (d, J=7.81 Hz, 1 H) 9.65 (d, J=8.30 Hz, 1 H) 10.45 (s, 1 H).

Example 111

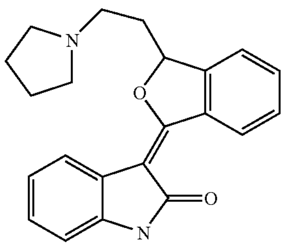

3-[3-(2-Pyrrolidin-1-yl-ethyl)-3H-isobenzofuran-1-ylidene]-1,3-dihydro-indol-2-one A solution of methanesulfonic acid 2-[3-(2-oxo-1,2-dihydro-indol-3-ylidene)-1,3-dihydro-isobenzofuran-1-yl]-ethyl ester (50 mg, 0.135 mmol) and pyrrolidine (113 μl, 1.35 mmol) in dioxane (0.8 ml) was heated at 85° C. for 2 minutes and then stirred at room temperature for 4 hours. The reaction was partitioned between EtOAc and water. The EtOAc layer was washed with water, brine, dried with anhydrous $Na_2SO_4$ and rotary evaporated to give brown oil. The brown oil was chromatographed ($CHCl_3$ to 2.5% MeOH/$CHCl_3$ gradient) and then recrystallized from EtOAc/hexane to produce 3-[3-(2-pyrrolidin-1-yl-ethyl)-3H-isobenzofuran-1-ylidene]-1,3-dihydro-indol-2-one as a yellow solid (25 mg, 54%).

$^1$H NMR (500 MHz, DMSO-D6) δ ppm 1.69 (br s, 4 H) 1.91 (m, 1 H) 2.36 (m, 1 H) 2.52 (obsc m, 5 H) 2.75 (m, 1 H) 6.04 (dd, J=8.30, 3.42 Hz, 1 H) 6.83 (d, J=7.81 Hz, 1 H) 6.98 (t, J=7.57 Hz, 1 H) 7.12 (m, 1 H) 7.57 (m, 1 H) 7.67 (m, 2 H) 7.84 (d, J=7.32 Hz, 1 H) 9.63 (d, J=7.81 Hz, 1 H) 10.43 (s, 1 H).

Example 112

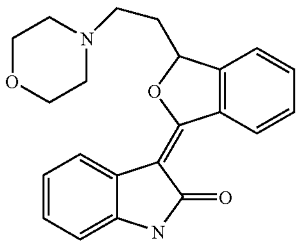

3-[3-(2-Morpholin-4-yl-ethyl)-3H-isobenzofuran-1-ylidene]-1,3-dihydro-indol-2-one A solution of methanesulfonic acid 2-[3-(2-oxo-1,2-dihydro-indol-3-ylidene)-1,3-dihydro-isobenzofuran-1-yl]-ethyl ester (50 mg, 0.135 mmol) and morpholine (118 μl, 1.35 mmol) in dioxane (0.8 ml) was heated at 70° C. for 40 minutes and then at 60° C. for 18 hours. The reaction was partitioned between EtOAc and water. The EtOAc layer was washed with water, brine, dried with anhydrous $Na_2SO_4$ and rotary evaporated to give a yellow film. The yellow film was chromatographed ($CHCl_3$ to 2% $MeOH/CHCl_3$ gradient) to give 3-[3-(2-morpholin-4-yl-ethyl)-3H-isobenzofuran-1-ylidene]-1,3-dihydro-indol-2-one as a yellow solid (37 mg, 76%).

$^1H$ NMR (500 MHz, $CDCl_3$) δ ppm 2.02 (m, 1 H) 2.33 (m, 1 H) 2.49 (m, 4 H) 2.59 (m, 1 H) 2.70 (m, 1 H) 3.69 (t, J=4.88 Hz, 4H) 5.95 (dd, J=8.30, 3.91 Hz, 1 H) 6.88 (d, J=7.81 Hz, 1 H) 7.06 (t, J=7.32 Hz, 1 H) 7.17 (m, 1 H) 7.40 (m, 1 H) 7.56 (m, 2 H) 7.60 (s, 1 H) 7.94 (d, J=7.81 Hz, 1 H) 9.71 (d, J=6.83 Hz, 1 H).

Example 113

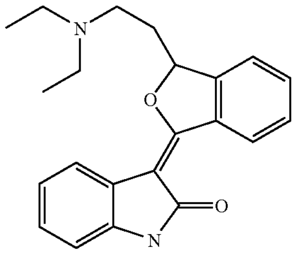

3-[3-(2-Diethylamino-ethyl)-3H-isobenzofuran-1-ylidene]-1,3-dihydro-indol-2-one

A solution of methanesulfonic acid 2-[3-(2-oxo-1,2-dihydro-indol-3-ylidene)-1,3-dihydro-isobenzofuran-1-yl]-ethyl ester (50 mg, 0.135 mmol) and diethylamine (279 μl, 2.7 mmol) in THF (0.8 ml) was heated at 60° C. After 3 hours, dioxane (0.3 ml) was added to give a solution and the reaction continued at 60° C. for 24 h. The reaction was partitioned between EtOAc and water. The EtOAc layer was washed with water, brine, dried with anhydrous $Na_2SO_4$ and rotary evaporated to give brown oil. The brown oil was chromatographed ($CHCl_3$ to 2% $MeOH/CHCl_3$ gradient) to yield 3-[3-(2-diethylamino-ethyl)-3H-isobenzofuran-1-ylidene]-1,3-dihydro-indol-2-one as a yellow-green solid (33 mg, 71%).

$^1H$ NMR (500 MHz, $CDCl_3$) δ ppm 1.06 (t, J=7.08 Hz, 6 H) 1.93 (m, 1 H) 2.27 (m, 1 H) 2.59 (m, 4 H) 2.72 (m, 1 H) 2.85 (m, 1 H) 5.93 (dd, J=8.79, 3.42 Hz, 1 H) 6.87 (d, J=7.81 Hz, 1 H) 7.05 (m, 1 H) 7.16 (m, 1 H) 7.40 (m, 1 H) 7.56 (m, 2 H) 7.60 (s, 1 H) 7.97 (d, J=6.83 Hz, 1 H) 9.71 (m, 1 H).

Example 114

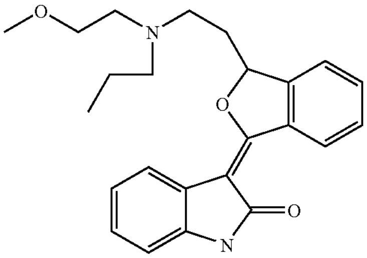

3-(3-{2-[(2-Methoxy-ethyl)-propyl-amino]-ethyl}-3H-isobenzofuran-1-ylidene)-1,3-dihydro-indol-2-one A solution of methanesulfonic acid 2-[3-(2-oxo-1,2-dihydro-indol-3-ylidene)-1,3-dihydro-isobenzofuran-1-yl]-ethyl ester (50 mg, 0.135 mmol) and N-(2-methoxyethyl)-N-propylamine (191 μl, 1.35 mmol) in dioxane (0.8 ml) was heated at 75° C. for 19 hours. The reaction was partitioned between EtOAc and water. The EtOAc layer was washed with water, brine, dried with anhydrous $Na_2SO_4$ and rotary evaporated to give brown oil. The brown oil was chromatographed with $CHCl_3$ to give 3-(3-{2-[(2-methoxy-ethyl)-propyl-amino]-ethyl}-3H-isobenzofuran-1-ylidene)-1,3-dihydro-indol-2-one as a yellow-brown film (11 mg, 20%).

$^1H$ NMR (500 MHz, $CDCl_3$) δ ppm 0.91 (t, J=7.32 Hz, 3H) 1.51 (m, 2 H) 1.89 (m, 1 H) 2.27 (m, 1 H) 2.51 (m, 2 H) 2.68 (m, 1 H) 2.77 (m, 2 H) 2.93 (m, 1 H) 3.34 (s, 3 H) 3.48 (m, 2 H) 5.98 (dd, J=9.03, 3.17 Hz, 1 H) 6.88 (d, J=7.81 Hz, 1 H) 7.05 (t, J=7.57 Hz, 1 H) 7.16 (m, 1 H) 7.40 (d, J=7.32 Hz, 1 H) 7.55 (m, 2 H) 7.87 (s, 1 H) 7.96 (d, J=7.32 Hz, 1 H) 9.72 (m, 1 H).

Example 115

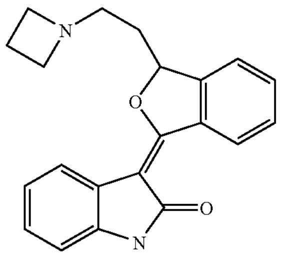

3-[3-(2-Azetidin-1-yl-ethyl)-3H-isobenzofuran-1-ylidene]-1,3-dihydro-indol-2-one To a slurry of azetidine hydrochloride (126 mg, 1.35 mmol) in THF (1.0 ml) was added a scoop of Aberlite-IRA-93 ion exchange resin, which was shaken 3 minutes to give a solution, dried with anhydrous $Na_2SO_4$ and filtered to remove resin. Then methanesulfonic acid 2-[3-(2-oxo-1,2-dihydro-indol-3-ylidene)-1,3-dihydro-isobenzofuran-1-yl]-ethyl ester (50.0 mg, 0.135 mmol) was added to the amine solution and heated at 60° C. for 18 hours (no reaction had occurred). After standing at room temperature for 2 days, to the mixture were added dioxane (0.3 ml), azetidine hydrochloride (63 mg, 0.675 mmol), and triethylamine (132 μl, 0.945 mmol). The resulting mixture was stirred at room temperature for 3 days, and heated at 60° C. for 24 hours. The reaction was partitioned between water and EtOAc. The EtOAc layer was extracted with 4% HCl aqueous solution, and then the aqueous layer was basified with saturated $NaHCO_3$ aqueous solution. The basified aqueous layer was extracted with EtOAc. The organic layer was washed with brine, dried over anhydrous $Na_2SO_4$ and rotary evaporated to give a film. The film was chromatographed (2.5% to 5% MeOH/$CHCl_3$ gradient) to provide 3-[3-(2-azetidin-1-yl-ethyl)-3H-isobenzofuran-1-ylidene]-1,3-dihydro-indol-2-one as a yellow film (8.7 mg, 19%).

$^1$H NMR (500 MHz, $CDCl_3$) δ ppm 1.86 (m, 1 H) 2.13 (m, 3 H) 2.57 (m, 1 H) 2.74 (m, 1 H) 3.24 (m, 4H) 5.90 (dd, J=8.30, 3.91 Hz, 1 H) 6.88 (d, J=7.81 Hz, 1 H) 7.08 (t, J=7.57 Hz, 1 H) 7.17 (t, J=7.57 Hz, 1 H) 7.39 (m, 1 H) 7.55 (m, 1 H) 7.92 (s, 1 H) 7.97 (d, J=7.32 Hz, 1 H) 9.71 (m, 1 H).

Preparation 13

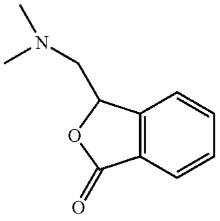

Preparation of 3-Dimethylaminomethyl-3H-isobenzofuran-1-one

To a solution of phthalide (0.50 g, 3.73 mmol) in THF (13.0 ml) at −78° C. was added 1.0M LiHMDS in THF (3.9 ml). The reaction was stirred for 10 minutes, and then N,N-dimethylmethyleneammonium iodide (0.76 g, 4.10 mmol) was added in one portion. The resulting mixture was continuously stirred at −78° C. for another 15 minutes. The mixture was then allowed to warm to 0° C. and then quenched into very dilute HCl aqueous solution. The aqueous layer was adjusted to acidic pH with 4% HCl aqueous solution and washed with EtOAc. The aqueous layer was basified with saturated $NaHCO_3$ aqueous solution and extracted with EtOAc. The combined organic layers were washed with water, brine, dried over anhydrous $Na_2SO_4$ and rotary evaporated to a light yellow oil. The oil was taken up in $CHCl_3$, filtered to remove an insoluble impurity, and then chromatographed through silica gel column ($CHCl_3$ to 2.5% MeOH/$CHCl_3$ gradient) to afford 3-dimethylaminomethyl-3H-isobenzofuran-1-one as a clear oil (0.24 g, 33%).

$^1$H NMR (500 MHz, $CDCl_3$) δ ppm 2.41 (s, 6 H) 2.67 (dd, J=13.18, 7.32 Hz, 1 H) 2.85 (dd, J=13.43, 4.64 Hz, 1 H) 5.55 (dd, J=7.57, 4.64 Hz, 1 H) 7.54 (m, 2 H) 7.67 (t, J=7.81 Hz, 1 H) 7.91 (m, 1 H).

Example 116

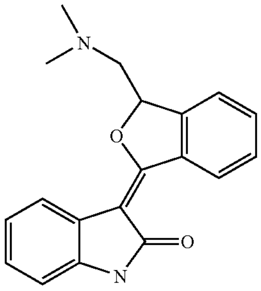

3-(3-Dimethylaminomethy-3H-isobenzofuran-1-ylidene)-1,3-dihydro-indol-2-one

To a solution of oxindole (205 mg, 1.54 mmol) in dimethoxyethane (4.0 ml) at room temperature was added 1.0M LiHMDS in THF (1.54 ml). After stirring for 10 minutes at room temperature, 3-dimethylaminomethyl-3H-isobenzofuran-1-one (235 mg, 1.23 mmol) in dimethoxyethane (0.5 ml) was added and the mixture was stirred rapidly for 1 hour. Additional 1.0M LiHMDS/THF (1.54 ml) was added. After 2 hours the reaction was quenched into 10% HCl (50 ml) and 25 ml water added. The aqueous layer was washed with EtOAc and then basified with saturated $NaHCO_3$ aqueous solution. The aqueous layer was extracted with EtOAc. The EtOAc layer was washed with brine, dried over anhydrous $Na_2SO_4$, and rotary evaporated to provide a yellow solid. The yellow solid was chromatographed silica gel column ($CHCl_3$ to 2.5% MeOH/$CHCl_3$ gradient) and then recrystallized from MeOH to give 3-(3-dimethylaminomethy-3H-isobenzofuran-1-ylidene)-1,3-dihydro-indol-2-one as yellow needles (92 mg, 24%).

$^1$H NMR (500 MHz, $CDCl_3$) δ ppm 2.48 (s, 6 H) 2.78 (dd, J=13.67, 7.32 Hz, 1 H) 2.96 (dd, J=13.67, 3.91 Hz, 1 H) 5.91 (dd, J=7.08, 4.15 Hz, 1 H) 6.87 (d, J=7.32 Hz, 1 H) 7.05 (m, 1 H) 7.16 (m, 1 H) 7.49 (m, 1 H) 7.56 (m, 2 H) 7.68 (s, 1 H) 8.00 (d, J=7.81 Hz, 1 H) 9.72 (m, 1 H).

Example 117

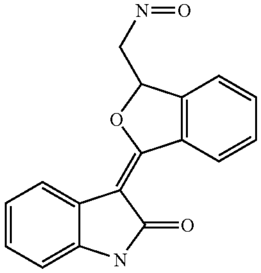

3-(3-Isocyanatomethyl-3H-isobenzofuran-1-ylidene)-1,3-dihydro-indol-2-one

To a mixture of [3-(2-oxo-1,2-dihydro-indol-3-ylidene)-1,3-dihydro-isobenzofuran-1-yl]-acetic acid (200 mg, 0.65 mmol) in THF (8.0 ml) at room temperature was added 2.5M n-BuLi in hexane (272 μl), and the yellow-brown slurry was stirred for 10 minutes. After cooling to 0° C., 2.0M oxalyl chloride in $CH_2Cl_2$ (325 μl) was added. The clear orange solution was stirred for 25 minutes, and then sodium azide (51 mg, 0.78 mmol) in water (0.5 ml) was added, followed by addition of water (1 ml). After 20 minutes, the reaction was partitioned between dilute $NaHCO_3$ aqueous solution and $CH_2Cl_2$. The $CH_2Cl_2$ layer was washed with brine and dried with anhydrous $Na_2SO_4$ to give a yellow solution. The solution was diluted with toluene (200 ml), and then rotary evaporated to 100 ml volume. The toluene solution was heated at 90° C. for 40 minutes, cooled to room temperature, and then rotary evaporated to give 3-(3-isocyanatomethyl-3H-isobenzofuran-1-ylidene)-1,3-dihydro-indol-2-one as a yellow oily solid (130 mg, 66%).

$^1$H NMR (500 MHz, $CDCl_3$) δ ppm 3.77 (dd, J=13.91, 6.10 Hz, 1 H) 3.90 (m, 1 H) 5.91 (dd, J=6.10, 3.91 Hz, 1 H) 6.88 (d, J=7.57 Hz, 1 H) 7.08 (t, J=7.57 Hz, 1 H) 7.19 (m, 1 H) 7.43 (dd, J=4.52, 3.78 Hz, 1 H) 7.61 (m, 2 H) 7.78 (br s, 1 H) 7.99 (d, J=7.57 Hz, 1 H) 9.72 (m, 1 H).

Example 118

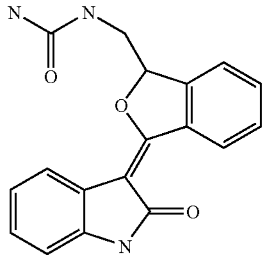

[3-(2-Oxo-1,2-dihydro-indol-3-ylidene)-1,3-dihydro-isobenzofuran-1-ylmethyl]-urea To a solution of 3-(3-Isocyanatomethyl-3H-isobenzofuran-1-ylidene)-1,3-dihydro-indol-2-one (65 mg, 0.21 mmol) in THF (4 ml) at room temperature was added concentrated $NH_4OH$ (2 ml). The reaction was stirred 5 minutes and then partitioned between EtOAc and water. The organic layer was washed with very dilute HCl, brine, dried with anhydrous $Na_2SO_4$ and rotary evaporated to obtain a solid. The solid was recrystallized from EtOAc/MeOH to give [3-(2-oxo-1,2-dihydro-indol-3-ylidene)-1,3-dihydro-isobenzofuran-1-ylmethyl]-urea as a yellow solid (46 mg, 68%).

$^1$H NMR (500 MHz, DMSO-D6) δ ppm 3.57 (m, 1 H) 3.75 (m, 1 H) 5.57 (s, 2 H) 5.97 (t, J=4.88 Hz, 1 H) 6.15 (t, J=5.86 Hz, 1 H) 6.83 (d, J=7.32 Hz, 1 H) 6.98 (t, J=7.57 Hz, 1 H) 7.12 (t, J=7.57 Hz, 1 H) 7.59 (t, J=7.32 Hz, 1 H) 7.65 (m, 2 H) 7.91 (d, J=7.32 Hz, 1 H) 9.64 (d, J=7.81 Hz, 1 H) 10.43 (s, 1 H).

Example 119

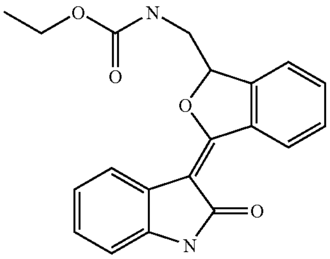

[3-(2-Oxo-1,2-dihydro-indol-3-ylidene)-1,3-dihydro-isobenzofuran-1-ylmethyl]-carbamic acid ethyl ester A solution of 3-(3-isocyanatomethyl-3H-isobenzofuran-1-yldene)-1,3-dihydro-indol-2-one (74 mg, 0.244 mmol) in anhydrous EtOH (4 ml) was heated at 75° C. for 17 hours. After cooling to room temperature, the yellow precipitate was removed by filtration and the filtrate was evaporated. The filtrate sample was chromatographed with $CHCl_3$ to afford [3-(2-oxo-1,2-dihydro-indol-3-ylidene)-1,3-dihydro-isobenzofuran-1-ylmethyl]-carbamic acid ethyl ester as a yellow solid (18 mg, 22%).

$^1$H NMR (500 MHz, $CDCl_3$) δ ppm 1.20 (t, J=7.08 Hz, 3 H) 3.59 (m, 1 H) 3.98 (m, 1 H) 4.09 (q, J=6.83 Hz, 2 H) 5.00 (t, J=6.35 Hz, 1 H) 5.93 (dd, J=5.37, 3.42 Hz, 1 H) 6.88 (d, J=7.81 Hz, 1 H) 7.07 (t, J=7.57 Hz, 1 H) 7.18 (t, J=7.57 Hz, 1 H) 7.50 (d, J=6.83 Hz, 1 H) 7.57 (m, 2 H) 7.85 (s, 1 H) 7.93 (d, J=7.81 Hz, 1 H) 9.69 (d, J=7.32 Hz, 1 H).

Example 120

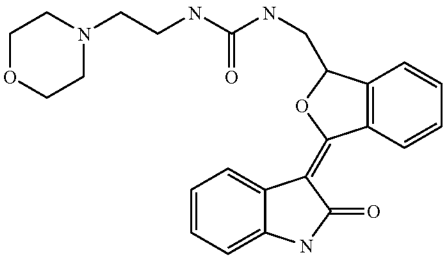

1-(2-Morpholin-4-yl-ethyl)-3-[3-(2-oxo-1,2-dihydro-indol-3-ylidene)-1,3-dihydro-isobenzofuran-1-ylmethyl]-urea A solution of 3-(3-isocyanatomethyl-3H-isobenzofuran-1-ylidene)-1,3-dihydro-indol-2-one (70 mg, 0.23 mmol) and 4-(2-aminoethyl)morpholine (90.0 μl, 0.69 mmol) in THF (2.0 ml) was stirred at room temperature for 25 minutes. The reaction was heated for 5 minutes at 60° C. and then partitioned between EtOAc and water. The organic layer was washed with saturated $NaHCO_3$ aqueous solution, and water, and then extracted with 4% HCl aqueous solution. The combined aqueous layers were basified with saturated $NaHCO_3$ aqueous solution and extracted with EtOAc. The combined organic layers were washed with brine, dried with anhydrous $Na_2SO_4$, and rotary evaporated to a yellow foam. The yellow foam was chromatographed through silica gel column ($CHCl_3$ to 5% MeOH/$CHCl_3$ gradient) to afford 1-(2-morpholin-4-yl-ethyl)-3-[3-(2-oxo-1,2-dihydro-indol-3-ylidene)-1,3-dihydro-isobenzofuran-1-ylmethyl]-urea as a yellow foam (18 mg, 18%).

$^1$H NMR (500 MHz, $CDCl_3$) δ ppm 2.31 (m, 6 H) 3.21 (m, 2 H) 3.48 (t, J=4.39 Hz, 4 H) 3.89 (m, 1 H) 4.01 (m, 1 H) 5.37 (t, J=4.88 Hz, 1 H) 5.66 (s, 1 H) 5.94 (t, J=3.91 Hz, 1 H) 6.66 (d, J=7.81 Hz, 1 H) 7.01 (m, 1 H) 7.08 (m, 1 H) 7.23 (m, 1 H) 7.48 (m, 2 H) 7.86 (s, 1 H) 7.92 (d, J=7.32 Hz, 1 H) 9.35 (d, J=8.30 Hz, 1 H).

Example 121

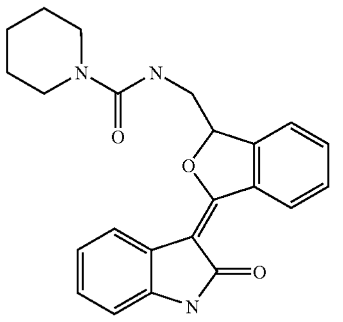

Piperidine-1-carboxylic acid [3-(2-oxo-1,2-dihydro-indol-3-ylidene)-1,3-dihydro-isobenzofuran-1-ylmethyl]-amide A solution of 3-(3-isocyanatomethyl-3H-isobenzofuran-1-ylidene)-1,3-dihydro-indol-2-one (95 mg, 0.31 mmol) and piperidine (92.8 μl, 0.94 mmol) in THF (2.0 ml) was stirred at room temperature for 4 hours. The reaction was partitioned between EtOAc and water. The organic layer was washed with dilute HCl aqueous solution, water, saturated $NaHCO_3$ aqueous solution, water, brine, dried with anhydrous $Na_2SO_4$, and rotary evaporated to a brown film. The brown film was chromatographed through silica gel column ($CHCl_3$ to 4% MeOH/$CHCl_3$ gradient) to produce piperidine-1-carboxylic acid [3-(2-oxo-1,2-dihydro-indol-3-ylidene)-1,3-dihydro-isobenzofuran-1-ylmethyl]-amide as a yellow solid (30 mg, 25%).

$^1$ HNMR (500 MHz, $CDCl_3$) δ ppm 1.50 (m, 4 H) 1.59 (m, 2 H) 3.30 (m, 4 H) 3.50 (m, 1 H) 4.09 (m, 1 H) 4.89 (t, J=5.86 Hz, 1 H) 5.99 (dd, J=7.32, 3.42 Hz, 1 H) 6.90 (d, J=7.81 Hz, 1 H) 7.04 (t, J=7.57 Hz, 1 H) 7.17 (t, J=7.57 Hz, 1 H) 7.55 (m, 3 H) 7.93 (d, J=7.32 Hz, 1 H) 8.15 (s, 1 H) 9.68 (m, 1 H).

Example 122

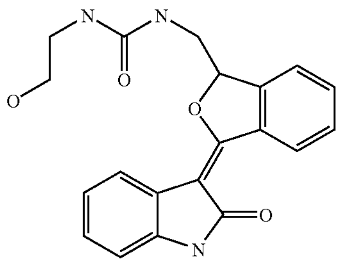

1-(2-Hydroxy-ethyl)-3-[3-(2-oxo-1,2-dihydro-indol-3-ylidene)-1,3-dihydro-isobenzofuran-1-ylmethyl]-urea A solution of 3-(3-isocyanatomethyl-3H-isobenzofuran-1-ylidene)-1,3-dihydro-indol-2-one (75 mg, 0.24 mmol) and 2-hydroxyethylamine (44.4 μl, 0.74 mmol) in THF (2.0 ml) was stirred at room temperature for 25 minutes and then heated at 60° C. for 5 minutes. The reaction was partitioned between EtOAc and water. The organic layer was washed with water, brine, dried with anhydrous $Na_2SO_4$, and rotary evaporated to result in a brown-yellow solid. The brown-yellow solid was chromatographed through silica gel column ($CHCl_3$ to 5% MeOH/$CHCl_3$ gradient) to give 1-(2-hydroxy-ethyl)-3-[3-(2-oxo-1,2-dihydro-indol-3-ylidene)-1,3-dihydro-isobenzofuran-1-ylmethyl]-urea as a yellow solid (18 mg, 20%).

$^1$H NMR (500 MHz, DMSO-D6) δ ppm 3.02 (m, 2 H) 3.32 (obsc m, 2 H) 3.56 (m, 1 H) 3.77 (m, 1 H) 4.63 (t, J=5.13 Hz, 1 H) 5.96 (dd, J=5.86, 4.39 Hz, 1 H) 6.12 (t, J=5.61 Hz, 1 H) 6.21 (t, J=5.86 Hz, 1 H) 6.83 (d, J=7.81 Hz, 1 H) 6.97 (m, 1 H) 7.12 (td, J=7.57, 0.98 Hz, 1 H) 7.62 (m, 3 H) 7.90 (d, J=7.81 Hz, 1 H) 9.64 (d, J=7.81 Hz, 1 H) 10.43 (s, 1 H).

Example 123

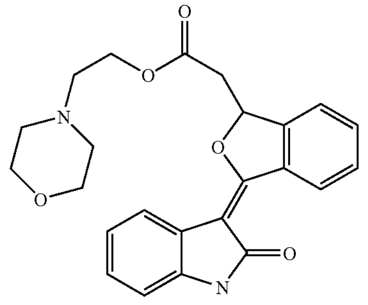

[3-(2-Oxo-1,2-dihydro-indol-3-ylidene)-1,3-dihydro-isobenzofuran-1-yl]-acetic acid 2-morpholin-4-yl-ethyl ester To a slurry of [3-(2-oxo-1,2-dihydro-indol-3-ylidene)-1,3-dihydro-isobenzofuran-1-yl]-acetic acid (100 mg, 0.32 mmol) in THF (4.0 ml) at room temperature was added 2.5M n-BuLi in hexane (13611), and the reaction was stirred for 10 minutes. After the reaction was cooled to 0° C., oxalyl chloride (163 μl, 0.32 mmol) was added. After stirring for 20 minutes, 4-(2-hydroxyethyl)morpholine (118 μl, 0.976 mmol) was added. The reaction was stirred for 5 minutes at 0° C., and then at room temperature for 20 minutes. The reaction was partitioned between EtOAc and saturated $NaHCO_3$. The EtOAc layer was washed with brine, dried with anhydrous $Na_2SO_4$ and rotary evaporated to afford an orange oil. The orange oil was chromatographed through silica gel column, eluted with $CHCl_3$, to give [3-(2-oxo-1,2-dihydro-indol-3-ylidene)-1,3-dihydro-isobenzofuran-1-yl]-acetic acid 2-morpholin-4-yl-ethyl ester as a yellow foam (43 mg, 32%).

$^1$H NMR (500 MHz, $CDCl_3$) δ ppm 2.49 (m, 4 H) 2.65 (t, J=5.86 Hz, 2 H) 2.94 (m, 1 H) 3.03 (m, 1 H) 3.67 (m, 4H) 4.35 (t, J=5.86 Hz, 2 H) 6.23 (dd, J=7.81, 5.37 Hz, 1 H) 6.87

(d, J=7.81 Hz, 1 H) 7.03 (t, J=7.57 Hz, 1 H) 7.16 (t, J=7.57 Hz, 1 H) 7.45 (m, 1 H) 7.57 (m, 2 H) 7.70 (s, 1 H) 7.90 (d, J=7.32 Hz, 1 H) 9.70 (m, 1 H).

Example 124

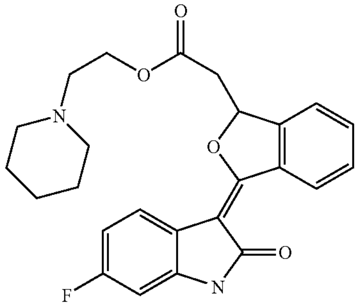

[3-(6-Fluoro-2-oxo-1,2-dihydro-indol-3-ylidene)-1,3-dihydro-isobenzofuran-1-yl]-acetic acid 2-piperidin-1-yl-ethyl ester To a slurry of [3-(6-fluoro-2-oxo-1,2-dihydro-indol-3-ylidene)-1,3-dihydro-isobenzofuran-1-yl]-acetic acid (449 mg, 1.38 mmol) in THF (20.0 ml) at room temperature was added 2.5M n-BuLi/Hexane (580 μl), and the reaction was stirred for 10 minutes. After cooling to 0° C., oxalyl chloride (690 μl, 1.38 mmol) was added. After 20 minutes, 4-(2-hydroxyethyl)morpholine (550 μ1, 4.14 mmol) was added. The mixture was stirred for 5 minutes at 0° C., and then at room temperature for 1 hour. The reaction was partitioned between EtOAc and water. The organic layer was washed with saturated $NaHCO_3$ aqueous solution, brine, dried with anhydrous $Na_2SO_4$ and rotary evaporated to produce a brown-yellow foam. The brown-yellow foam was chromatographed through silica gel column ($CHCl_3$ to 2.5% MeOH/$CHCl_3$ gradient) to afford a yellow solid. The solid was dissolved in hot EtOAc/Hexane, allowed to cool to room temperature, and filtered to remove fluffy precipitate. The filtrate was cooled in refrigerator after concentrating the solution. The precipitate was filtered to give [3-(6-fluoro-2-oxo-1,2-dihydro-indol-3-ylidene)-1,3-dihydro-isobenzofuran-1-yl]-acetic acid 2-piperidin-1-yl-ethyl ester as a yellow solid (200 mg, 33%).

$^1$H NMR (500 MHz, $CDCl_3$) δ ppm 1.43 (m, 2 H) 1.57 (m, 4 H) 2.45 (br s, 4 H) 2.64 (t, J=6.10 Hz, 2 H) 2.92 (dd, J=16.35, 8.06 Hz, 1 H) 3.01 (m, 1 H) 4.35 (t, J=5.98 Hz, 2 H) 6.21 (dd, J=7.93, 5.25 Hz, 1 H) 6.61 (dd, J=8.79, 2.20 Hz, 1 H) 6.72 (m, 1 H) 7.45 (m, 1 H) 7.57 (m, 2 H) 7.82 (dd, J=8.54, 5.61 Hz, 1 H) 8.12 (br s, 1 H) 9.64 (m, 1 H).

Example 125

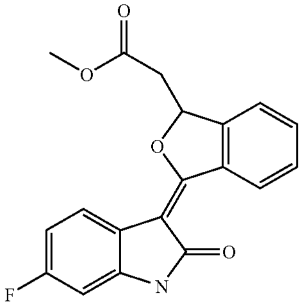

[3-(6-Fluoro-2-oxo-1,2-dihydro-indol-3-ylidene)-1,3-dihydro-isobenzofuran-1-yl]-acetic acid methyl ester To a slurry of [3-(6-fluoro-2-oxo-1,2-dihydro-indol-3-ylidene)-1,3-dihydro-isobenzofuran-1-yl]-acetic acid (300 mg, 0.922 mmol) in a mixture of dioxane (15 ml) and MeOH (7 ml) was added 2.0M (trimethylsilyl)diazomethane/Hexanes (507 μl) and the resultant solution was stirred for 15 minutes at room temperature. The solvent was rotary evaporated and the residue was partitioned between EtOAc and saturated $NaHCO_3$. The organic layer (combined a EtOAc solution from a previous 100 mg (0.307 mmol) scale test reaction) was then washed with dilute HCl aqueous solution, water, brine, dried with anhydrous $Na_2SO_4$, and rotary evaporated to a yellow solid. The solid was triturated with 30% EtOAc in hexane to yield [3-(6-fluoro-2-oxo-1,2-dihydro-indol-3-ylidene)-1,3-dihydro-isobenzofuran-1-yl]-acetic acid methyl ester as a bright yellow solid (388 mg, 93%).

$^1$H NMR (500 MHz, DMSO-D6) δ ppm 2.88 (dd, J=16.60, 8.79 Hz, 1 H) 3.40 (dd, J=16.60, 3.91 Hz, 1 H) 3.71 (s, 3 H) 6.26 (dd, J=9.03, 3.66 Hz, 1 H) 6.65 (dd, J=9.28, 2.44 Hz, 1 H) 6.79 (m, 1 H) 7.60 (m, 1 H) 7.68 (m, 2 H) 7.73 (dd, J=8.54, 5.61 Hz, 1 H) 9.56 (d, J=7.81 Hz, 1 H) 10.61 (s, 1 H).

Preparation 14

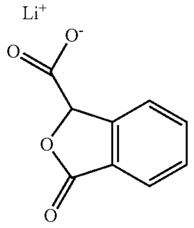

Preparation of Lithium 3-oxo-1,3-dihydro-2-benzofuran-1-carboxylate

To a solution of phthalide (2.0 g, 14.9 mmol) in THF (60.0 ml) at −78° C. was added 1.0M LiHMDS/THF (15.7 ml) over 10 minutes. The reaction was stirred for 15 minutes at −78° C. and then the ice bath was removed. The reaction was quenched into dry ice using a cannula and then allowed to warm to room temperature. After adding 40 ml hexane, the cloudy mixture was rotary evaporated and chased with hexane to give lithium 3-oxo-1,3-dihydro-2-benzofuran-1-carboxylate as a yellow solid (2.86 g, 100%).

$^1$H NMR (500 MHz, DMSO-D6) δ ppm 5.57 (s, 1 H) 7.49 (t, J=7.57 Hz, 1 H) 7.66 (t, J=7.57 Hz, 1 H) 7.72 (t, J=7.81 Hz, 2 H).

Example 126

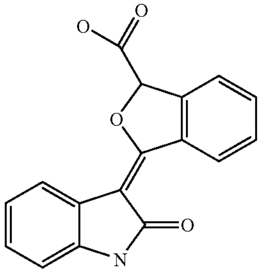

3-(2-Oxo-1,2-dihydro-indol-3-ylidene)-1,3-dihydro-isobenzofuran-1-carboxylic acid To a solution of oxindole (1.10 g, 8.27 mmol) in dimethoxyethane (30.0 ml) at room temperature was added 1.0M LiHMDS/THF (17.0 ml). The mixture was stirred for 10 minutes at room temperature, and lithium 3-oxo-1,3-dihydro-2-benzofuran-1-carboxylate (1.37 g, 7.44 mmol) was added in one portion. After the reaction was rapidly stirred at room temperature for 18 hours, it was quenched into 4% HCl aqueous solution (200 mL), and the mixture was stirred 5 minutes. The aqueous layer was extracted with EtOAc. The combined organic layers were washed with water and then extracted with saturated $NaHCO_3$ aqueous solution. The aqueous layer was acidified with 4% HCl aqueous solution, and extracted with EtOAc. The combined organic layers were washed with brine, dried with anhydrous $Na_2SO_4$, and rotary evaporated to obtain a yellow solid. The yellow solid was triturated at room temperature with $CHCl_3$, and then triturated with hot isopropanol to give 3-(2-oxo-1,2-dihydro-indol-3-ylidene)-1,3-dihydro-isobenzofuran-1-carboxylic acid as a yellow solid (287 mg, 13%).

$^1$H NMR (500 MHz, DMSO-D6) δ ppm 6.54 (s, 1 H) 6.85 (d, J=7.57 Hz, 1 H) 7.00 (t, J=7.57 Hz, 1 H) 7.15 (t, J=7.57 Hz, 1 H) 7.65 (m, 1 H) 7.71 (m, 2 H) 7.89 (d, J=7.57 Hz, 1 H) 9.63 (d, J=7.81 Hz, 1 H) 10.51 (s, 1 H) 13.90 (s, 1 H).

Preparation 15

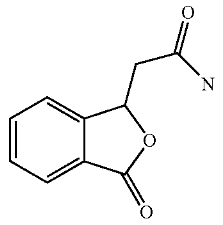

Preparation of 2-(3-oxo-1,3-dihydro-2-benzofuran-1-yl)acetamide

A solution of (3-oxo-1,3-dihydro-isobenzofuran-1-yl)-acetic acid (5.0 g, 26 mmol) in thionyl chloride (10 ml) was heated at 75° C. for 15 minutes. The excess thionyl chloride was removed under vacuum to give a red oil. The red oil was dissolved in $CH_2Cl_2$ (10 ml) and then the solution was slowly added to concentrated $NH_4OH$ (40 ml) at 0° C. The resultant solid was filtered and washed with water and hexane, followed by addition of toluene. Removal of the solvent led to 2-(3-oxo-1,3-dihydro-2-benzofuran-1-yl)acetamide as a cream solid (4.2 g, 84%).

$^1$H NMR (300 MHz, DMSO-D6) δ ppm 2.56 (dd, J=15.39, 8.65 Hz, 1 H) 2.86 (dd, J=15.24, 4.98 Hz, 1 H) 5.91 (dd, J=8.35, 4.84 Hz, 1 H) 7.09 (br s, 1 H) 7.49 (br s, 1 H) 7.61 (t, J=7.48 Hz, 1 H) 7.70 (d, J=7.62 Hz, 1 H) 7.81 (m, 2 H).

Preparation 16

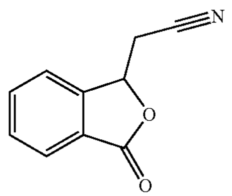

Preparation of (3-oxo-1,3-dihydro-2-benzofuran-1-yl)acetonitrile

To a mixture of $P_2O_5$ (4.0 g, 28.2 mmol) in xylenes (20 ml) was added 2-(3-oxo-1,3-dihydro-2-benzofuran-1-yl)acetamide (2.0 g, 10.5 mmol) and the reaction was heated at 140° C. for 5 minutes. The mixture was filtered while warm to give the xylene filtrate, and a brown gummy solid. The brown gummy solid was triturated with toluene to give a light yellow solution. The xylene filtrate was combined with the yellow solution, and diluted with hexane. Upon cooling at 0° C., a white precipitate formed. The precipitate was separated to give solid A and filtrate A.

The solid A was partitioned between a mixture of 4% HCl aqueous solution and EtOAc. The EtOAc layer was washed with water, brine, and dried over anhydrous $Na_2SO_4$ Removal of the solvent led to white solid B (0.18 g).

The above brown gummy solid was partitioned between water and EtOAc. The EtOAc layer was separated, and combined with filtrate A. The combined filtrates were washed with water, brine, dried with anhydrous $Na_2SO_4$ Evaporation of the filtrates provided solid C, which was chromatographed through silica gel column, eluted with 50% EtOAc in hexane to provide white solid D (0.90 g).

The solid B and solid D were combined to afford (3-oxo-1,3-dihydro-2-benzofuran-1-yl)acetonitrile (1.08 g, 60%).

$^1$H NMR (300 MHz, CHLOROFORM-D) δ ppm 2.96 (dd, J=16.71, 6.74 Hz, 1 H) 3.11 (m, 1 H) 5.68 (m, 1 H) 7.66 (m, 2 H) 7.78 (m, 1 H) 7.97 (d, J=7.62 Hz, 1 H).

Preparation 17

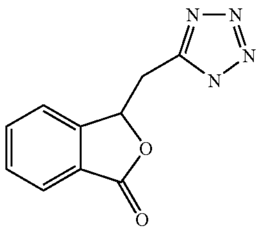

Preparation of 3-(1H-tetrazol-5-ylmethyl)-2-benzofuran-1(3H)-one

A solution of (3-oxo-1,3-dihydro-2-benzofuran-1-yl)acetonitrile (890 mg, 5.14 mmol) and azidotributyltin (1.97 ml, 7.20 mmol) in dioxane (4.0 ml) was heated at 95° C. for 17 hours. The reaction was partitioned between EtOAc and saturated $NaHCO_3$ aqueous solution, and then washed with saturated $NaHCO_3$ aqueous solution. The aqueous layers were combined, washed with EtOAc, then acidified with 10% HCl aqueous solution. The acidic aqueous layer was extracted with EtOAc. The combined organic layers were then washed with brine, dried with anhydrous $Na_2SO_4$, and rotary evaporated to obtain a yellow oil. The oil was dissolved in $CHCl_3$/Hexane and allowed to crystallize, leading to 3-(1 H-tetrazol-5-ylmethyl)-2-benzofuran-1(3 H)-one as a white solid (913 mg, 82%).

$^1$H NMR (300 MHz, DMSO-D6) δ ppm 3.49 (dd, J=15.68, 7.48 Hz, 1 H) 3.83 (dd, J=15.68, 4.25 Hz, 1 H) 6.06 (dd, J=7.48, 4.25 Hz, 1 H) 7.61 (t, J=7.48 Hz, 1 H) 7.74 (d, J=7.62 Hz, 1 H) 7.81 (t, J=7.04 Hz, 2 H).

Example 127

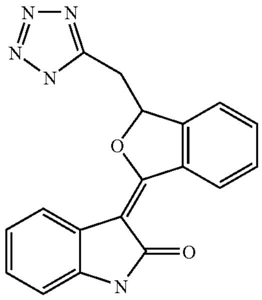

(3E)-3-[3-(1H-tetrazol-5-ylmethyl)-2-benzofuran-1(3H)-ylidene]-1,3-dihydro-2H-indol-2-one To a solution of oxindole (100 mg, 0.751 mmol) in dimethoxyethane (2.0 ml) at room temperature was added 1.0M LiHMDS/THF (2.25 ml). After the mixture was stirred for 10 minutes at room temperature, the solid 3-(1 H-tetrazol-5-ylmethyl)-2-benzofuran-1(3 H)-one (146 mg, 0.676 mmol) was added in one portion and the reaction was rapidly stirred at room temperature for 1.5 hours. The reaction was quenched into 3M HCl aqueous solution (60 ml) to give a yellow precipitate. The aqueous layer was decanted away and the solid was rinsed twice with water.

The aqueous layers were combined and extracted with EtOAc. The EtOAc portion was then extracted with saturated $NaHCO_3$. The aqueous portion was acidified with 3M HCl aqueous solution, and then extracted with EtOAc. The combined organic layers were washed with brine, dried with anhydrous $Na_2SO_4$, and rotary evaporated to provide yellow solid film A.

The above yellow precipitate was then dissolved in EtOAc by warming, washed with water, brine, dried with anhydrous $Na_2SO_4$, and rotary evaporated to give a yellow solid. The yellow solid was heated with MeOH and then filtered to remove insoluble solid, and give filtrate A.

The filtrate A was combined with the yellow solid film A, and was then recrystallized from dioxane to obtain a pure solid wet with dioxane. The pure solid was dissolved in 30% MeOH in $CHCl_3$ and then rotary evaporated to give (3E)-3-[3-(1H-tetrazol-5-ylmethyl)-2-benzofuran-1 (3 H)-ylidene]-1,3-dihydro-2H-indol-2-one as a yellow solid (22 mg, 10%).

$^1$H NMR (300 MHz, DMSO-D6) δ ppm 3.45 (dd, J=15.54, 8.50 Hz, 1 H) 3.93 (dd, J=15.54, 4.10 Hz, 1 H) 6.39 (dd, J=8.21, 4.10 Hz, 1 H) 6.85 (m, 2 H) 7.10 (m, 1 H) 7.52 (d, J=7.62 Hz, 1 H) 7.61 (m, 1 H) 7.70 (m, 2 H) 9.60 (d, J=7.92 Hz, 1 H) 10.44 (s, 1 H).

Example 128

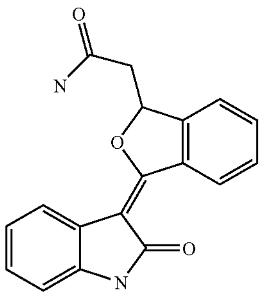

2-[3-(2-Oxo-1,2-dihydro-indol-3-ylidene)-1,3-dihydro-isobenzofuran-1-yl]-acetamide To a solution of [3-(2-oxo-1,2-dihydro-indol-3-ylidene)-1,3-dihydro-isobenzofuran-1-yl]-acetic acid (100 mg, 0.325 mmol) and triethylamine (58.9 μl, 0.423 mmol) in THF (3.0 ml) was added chloroethylformate (35.7 μl, 0.374 mmol). The mixture was stirred at room temperature for 25 minutes, and then concentrated $NH_4OH$ (3.0 ml) was added. After stirring for 8 minutes at room temperature, the reaction was partitioned between 4% HCl aqueous solution, and EtOAc. The organic layer was then washed with saturated $NaHCO_3$ aqueous solution, water, dilute HCl aqueous solution, brine, dried with anhydrous $Na_2SO_4$ and rotary evaporated to yield a solid. The solid was recrystallized from $CHCl_3$/MeOH to give 2-[3-(2-oxo-1,2-dihydro-indol-3-ylidene)-1,3-dihydro-isobenzofuran-1-yl]-acetamide as a yellow-gold solid (34.4 mg, 35%).

$^1$H NMR (500 MHz, DMSO-D6) δ ppm 2.57 (dd, J=15.13, 9.28 Hz, 1 H) 2.98 (dd, J=14.89, 4.15 Hz, 1 H) 6.25 (dd, J=9.28, 3.91 Hz, 1 H) 6.83 (d, J=7.81 Hz, 1 H) 6.93 (m, 1 H) 7.12 (td, J=7.69, 1.22 Hz, 1 H) 7.18 (s, 1 H) 7.52 (s, 1 H) 7.59 (m, 1 H) 7.67 (m, 2 H) 7.80 (d, J=7.32 Hz, 1 H) 9.63 (d, J=8.30 Hz, 1 H) 10.43 (s, 1 H).

Preparation 18

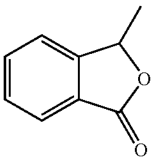

Preparation of 3-methyl-2-benzofuran-1(3H)-one

To a solution of 2-bromobenzoic acid (0.50 g, 2.49 mmol) in THF (12.0 ml) cooled at −78° C. was added 2.5M n-BuLi in hexane (2.0 ml). After stirring for 25 minutes, a solution of acetaldehyde (0.142 g, 3.23 mmol) in THF (0.3 ml) was added. The reaction was allowed to warm to room temperature after 8 minutes at −78° C., and then quenched into 10% HCl aqueous solution (30 ml). The acidic solution was rapidly stirred for 1.5 hours, and then extracted with EtOAc. The combined organic layers were washed with saturated $NaHCO_3$ aqueous solution, brine, dried with anhydrous $Na_2SO_4$, and rotary evaporated to an oily residue. Gradient chromatography of the oil residue through a silica gel column with 20% to 30% EtOAc in hexane afforded 3-methyl-2-benzofuran-1(3 H)-one as a clear oil (130 mg, 35%).

$^1$H NMR (300 MHz, CDCl3) δ ppm 1.64 (d, J=6.74 Hz, 3 H) 5.57 (q, J=6.74 Hz, 1 H) 7.45 (dd, J=7.62, 0.88 Hz, 1 H) 7.53 (t, J=7.48 Hz, 1 H) 7.69 (td, J=7.55, 1.03 Hz, 1 H) 7.90 (d, J=7.62 Hz, 1 H).

Preparation 19

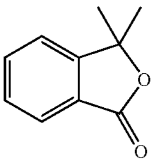

Preparation of 3,3-dimethyl-2-benzofuran-1(3H)-one

To a solution of 2-bromobenzoic acid (500 mg, 2.49 mmol) in THF (12.0 ml) cooled at −78° C. was added 2.5M n-BuLi/Hexane (2.0 ml). After stirring for 18 minutes, acetone (0.91 ml, 12.4 mmol) was added. The reaction was allowed to warm to room temperature after 5 minutes at −78° C., and then quenched into 10% HCl aqueous solution (50 ml). The acidic solution was rapidly stirred for 1 hour, and then extracted with EtOAc. The combined organic layers were washed with saturated $NaHCO_3$, brine, dried with anhydrous $Na_2SO_4$, and rotary evaporated to give a mixture. Gradient chromatography of the mixture through silica gel column eluted with 20% to 30% EtOAc in hexane afforded 3,3-dimethyl-2-benzofuran-1(3H)-one as a white solid (161 mg, 40%).

$^1$H NMR (300 MHz, $CDCl_3$) δ ppm 1.67 (s, 6 H) 7.41 (d, J=7.62 Hz, 1 H) 7.51 (td, J=7.48, 0.88 Hz, 1 H) 7.67 (td, J=7.55, 1.03 Hz, 1 H) 7.87 (d, J=7.62 Hz, 1 H).

Example 129

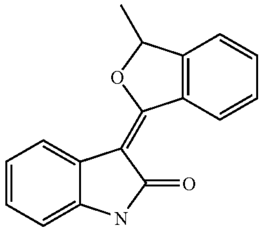

(3E)-3-(3-methyl-2-benzofuran-1(3H)-ylidene)-1,3-dihydro-2H-indol-2-one

To a solution of oxindole (119 mg, 0.891 mmol) in THF (2.0 ml) cooled at 0° C. was added 1.0M LiHMDS/THF (1.78 ml). The mixture was stirred for 4 minutes at 0° C., then allowed to warm to room temperature for an additional 6 minutes. A solution of 3-methyl-2-benzofuran-1(3 H)-one (119 mg, 0.802 mmol) in THF (0.5 ml) was added, and the reaction was rapidly stirred for 1.5 hours. The reaction was quenched into 10% HCl aqueous solution (30 ml). The resulting mixture was stirred 5 minutes, and then extracted into EtOAc. The combined organic layers were washed with water, brine, dried with anhydrous $Na_2SO_4$, and rotary evaporated to a yellow oil. Upon standing at room temperature overnight a yellow crystalline solid formed from the yellow oil. The remaining oil was removed by pipet and the solid was recrystallized from EtOAc to produce (3E)-3-(3-methyl-2-benzofuran-1(3 H)-ylidene)-1,3-dihydro-2H-indol-2-one as a yellow solid (32 mg, 15%).

$^1$H NMR (300 MHz, $CDCl_3$) δ ppm 1.73 (d, J=6.74 Hz, 3 H) 5.92 (q, J=6.45 Hz, 1 H) 6.88 (m, 1 H) 7.06 (td, J=7.62, 1.17 Hz, 1 H) 7.16 (td, J=7.55, 1.32 Hz, 1 H) 7.39 (m, 1 H) 7.56 (m, 2 H) 7.85 (s, 1 H) 8.00 (dt, J=7.62, 0.59 Hz, 1 H) 9.72 (m, 1 H).

Example 130

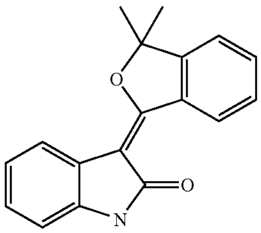

(3E)-3-(3,3-dimethyl-2-benzofuran-1(3H)-ylidene)-1,3-dihydro-2H-indol-2-one

To a solution of oxindole (127 mg, 0.956 mmol) in THF (2.0 ml) cooled at 0° C. was added 1.0M LiHMDS in THF (1.91 ml). The mixture was stirred for 4 minutes at 0° C., then allowed to warm to room temperature for an additional 6 minutes. The solid 3,3-dimethyl-2-benzofuran-1(3H)-one (140 mg, 0.86 mmol) was added in one portion and the reaction rapidly stirred for 1.5 hours. The reaction was quenched into 30 ml 10% HCl aqueous solution. The resulting mixture was stirred 5 minutes, and then extracted into EtOAc. The combined organic layers were washed with water, brine, dried with anhydrous $Na_2SO_4$, and rotary evaporated to a yellow oil. The yellow oil was chromatographed through silica gel column (20% to 30% EtOAc/hexane gradient) to give (3E)-3-(3,3-dimethyl-2-benzofuran-1(3H)-ylidene)-1,3-dihydro-2H-indol-2-one as a yellow solid (99 mg, 41%).

$^1$H NMR (300 MHz, $CDCl_3$) δ ppm 1.74 (s, 6 H) 6.88 (d, J=7.92 Hz, 1H) 7.06 (m, 1 H) 7.16 (m, 1 H) 7.33 (m, 1 H) 7.54 (m, 2H) 7.87 (s, 1 H) 8.00 (dd, J=7.62, 0.59 Hz, 1 H) 9.70 (m, 1 H).

Preparation 20

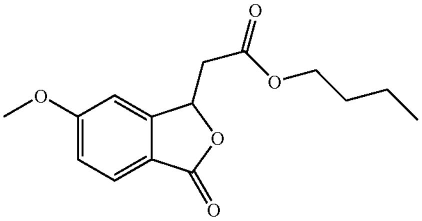

Preparation of Butyl (6-methoxy-3-oxo-1,3-dihydro-2-benzofuran-1-yl)acetate

A mixture of 4-methoxybenzoic acid (1.52 g, 10.0 mmol), palladium (II) acetate (0.56 g, 2.5 mmol), copper (II) acetate monohydrate (0.499 g, 2.5 mmol) and 4 Å molecular sieves (1.75 g) in DMF (40 ml) was stirred at room temperature for 5 minutes. Butyl acrylate was add (2.57 g, 20.0 mmol), and the resulting mixture was heated at 120° C. for 25 hours and then at 140° C. for 9 hours. Upon cooling the mixture was filtered and partitioned between dilute HCl aqueous solution and EtOAc. The organic layer was washed with saturated $NaHCO_3$ aqueous solution, water, brine, then dried with anhydrous $Na_2SO_4$ and rotary evaporated to a brown oil. The oil was triturated with hexane and the remaining oil was chromatographed through silica gel column (20% to 30%

EtOAc/Hexane gradient) to give the desired product contaminated with 4-methoxybenzoic acid. The mixture was dissolved in EtOAc and washed with saturated $NaHCO_3$ aqueous solution, brine, dried with anhydrous $Na_2SO_4$. Removal of the solvent yielded butyl (6-methoxy-3-oxo-1,3-dihydro-2-benzofuran-1-yl)acetate as a light yellow oil (0.26 g, 9%).

$^1$H NMR (300 MHz, CHLOROFORM-D) δ ppm 0.94 (t, J=7.33 Hz, 3 H) 1.37 (m, 2 H) 1.63 (m, 2 H) 2.84 (dd, J=16.56, 6.30 Hz, 1 H) 2.94 (m, 1 H) 3.90 (s, 3 H) 4.17 (t, J=6.60 Hz, 2 H) 5.80 (t, J=6.60 Hz, 1 H) 6.94 (m, 1 H) 7.05 (dd, J=8.50, 2.35 Hz, 1 H) 7.81 (d, J=8.50 Hz, 1 H).

Preparation 21

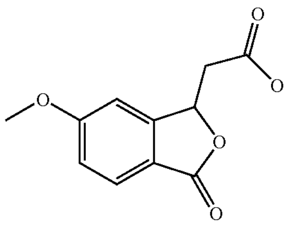

Preparation of 6-methoxy-3-oxo-1,3-dihydro-2-benzofuran-1-yl)acetic acid

A mixture of butyl (6-methoxy-3-oxo-1,3-dihydro-2-benzofuran-1-yl)acetate (251 mg, 0.902 mmol) in 6M HCl/$H_2O$ (10.0 ml) was heated at 80° C. for 2.5 hours. The mixture was diluted with water and extracted with EtOAc. The combined organic layers were washed with brine, dried with anhydrous $Na_2SO_4$, and rotary evaporated to give a pale yellow solid. The pale yellow solid was triturated at room temperature with 10% EtOAc/Hexane and then only hexane to afford (6-methoxy-3-oxo-1,3-dihydro-2-benzofuran-1-yl) acetic acid as a white solid (150.2 mg, 75%).

$^1$H NMR (300 MHz, DMSO-D6) δ ppm 2.66 (dd, J=16.71, 8.50 Hz, 1 H) 3.18 (dd, J=116.71, 3.81 Hz, 1 H) 3.87 (s, 3 H) 5.78 (dd, J=8.50, 3.81 Hz, 1 H) 7.12 (dd, J=8.50, 2.05 Hz, 1 H) 7.28 (d, J=1.47 Hz, 1 H) 7.73 (d, J=8.50 Hz, 1 H) 12.59 (br s, 1 H).

Example 131

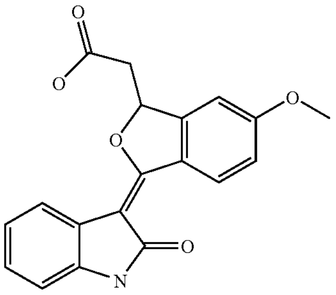

[(3E)-6-methoxy-3-(2-oxo-1,2-dihydro-3H-indol-3-ylidene)-1,3-dihydro-2-benzofuran-1-yl]acetic acid To a solution of oxindole (50 mg, 0.375 mmol) in dimethoxyethane (1.0 ml) at room temperature was added 1.0M LiHMDS in THF (1.13 ml), and the mixture was stirred for 10 minutes at room temperature. The solid (6-methoxy-3-oxo-1,3-dihydro-2-benzofuran-1-yl)acetic acid (75 mg, 0.338 mmol) was added in one portion and the reaction rapidly stirred at room temperature for 3 hours (an additional dimethoxyethane (0.75 ml) was added to thin the mixture in order to stir). The reaction was quenched into 10% HCl aqueous solution (50 ml). The resulting mixture was stirred 10 minutes, then extracted into EtOAc. The combined organic layers were then extracted with saturated $NaHCO_3$ aqueous solution. The aqueous layer was acidified with 10% HCl aqueous solution, extracted with EtOAc. The combined organic layers were washed with brine, dried with anhydrous $Na_2SO_4$, and rotary evaporated to give a yellow solid. The yellow solid was recrystallized from $CHCl_3$/MeOH to give a solid mixture (27 mg). Purification of the mixture by silica gel column chromatography, eluted with 4% MeOH/$CHCl_3$ to afford [(3E)-6-methoxy-3-(2-oxo-1,2-dihydro-3H-indol-3-ylidene)-1,3-dihydro-2-benzofuran-1-yl]acetic acid as a yellow solid (6.1 mg, 5%).

$^1$H NMR (300 MHz, ACETONE-D6) δ ppm 2.87 (dd, J=16.71, 9.09 Hz, 1 H) 3.28 (dd, J=16.71, 4.10 Hz, 1 H) 3.94 (s, 3 H) 6.22 (dd, J=8.65, 3.96 Hz, 1 H) 6.91 (m, 2 H) 7.09 (m, 2 H) 7.26 (d, J=1.47 Hz, 1 H) 7.89 (d, J=7.92 Hz, 1H) 9.32 (s, 1 H) 9.68 (d, J=8.79 Hz, 1 H).

Example 132

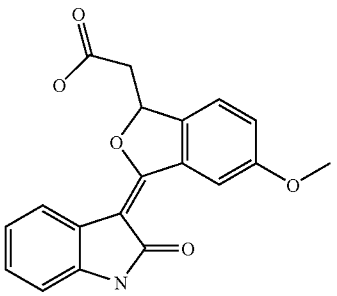

[(3E)-5-methoxy-3-(2-oxo-1,2-dihydro-3H-indol-3-ylidene)-1,3-dihydro-2-benzofuran-1-yl]acetic acid To a solution of oxindole (133 mg, 1.0 mmol) in dimethoxyethane (3.0 ml) cooled to 0° C. was added 1.0M LiHMDS/THF (3.0 ml). The mixture was stirred for 8 minutes at 0° C., and then the ice bath was removed. The solid (5-methoxy-3-oxo-1,3-dihydro-isobenzofuran-1-yl)-acetic acid (200 mg, 0.90 mmol) was added in one portion and the reaction mixture was rapidly stirred at room temperature for 3.5 hours. The reaction was quenched into 10% HCl aqueous solution (30 ml). After stirred for 10 minutes, the resulting mixture was extracted with EtOAc, and then the combined organic layers were then extracted with saturated $NaHCO_3$. The aqueous layer was acidified with 10% HCl aqueous solution, and extracted with EtOAc. The combined organic layers were washed with brine, dried with anhydrous $Na_2SO_4$, and rotary evaporated to produce a yellow solid. The yellow solid was recrystallized from EtOAc to give a solid (94 mg), which was recrystallized from MeOH to afford [(3E)-5-methoxy-3-(2-oxo-1,2-dihydro-3H-indol-3-ylidene)-1,3-dihydro-2-benzofuran-1-yl] acetic acid as a yellow fluffy solid (48 mg, 16%).

$^1$H NMR (300 MHz, $d_6$-DMSO) δ ppm 2.68 (dd, J=16.42, 9.09 Hz, 1 H) 3.24 (dd, J=16.42, 3.81 Hz, 1 H) 3.86 (s, 3 H)

6.17 (dd, J=9.09, 3.81 Hz, 1 H) 6.84 (d, J=7.62 Hz, 1 H) 6.93 (t, J=7.62 Hz, 1 H) 7.12 (t, J=7.48 Hz, 1 H) 7.26 (dd, J=8.50, 2.35 Hz, 1 H) 7.59 (d, J=8.50 Hz, 1 H) 7.79 (d, J=7.62 Hz, 1 H) 9.33 (d, J=2.35 Hz, 1 H) 10.40 (s, 1 H) 12.66 (s, 1 H).

Example 133

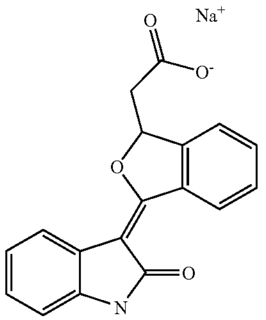

Sodium [(3E)-3-(2-oxo-1,2-dihydro-3H-indol-3-ylidene)-1,3-dihydro-2-benzofuran-1-yl]acetate To a slurry of [3-(2-oxo-1,2-dihydro-indol-3-ylidene)-1,3-dihydro-isobenzofuran-1-yl]-acetic acid (430 mg, 1.40 mmol) in MeOH (100.0 ml) at room temperature was added 0.5M NaOMe/MeOH (2.80 ml). The solution was rapidly stirred for 15 minutes and then rotary evaporated (combined 116 mg of product obtained from previously run reaction). The solid was chased with MeOH (20 ml), and then with EtOAc (2×15 ml) to give sodium [(3E)-3-(2-oxo-1,2-dihydro-3H-indol-3-ylidene)-1,3-dihydro-2-benzofuran-1-yl]acetate as a yellow solid (576 mg, 100%).

$^1$H NMR (300 MHz, DMSO-D6) δ ppm 2.52 (obsc m, 2 H) 6.23 (t, J=6.89 Hz, 1 H) 6.82 (d, J=7.62 Hz, 1 H) 6.93 (t, J=7.62 Hz, 1 H) 7.10 (t, J=7.77 Hz, 1 H) 7.53 (t, J=7.48 Hz, 1 H) 7.61 (t, J=7.18 Hz, 1 H) 7.73 (d, J=7.33 Hz, 1 H) 7.86 (d, J=7.33 Hz, 1 H) 9.63 (d, J=7.92 Hz, 1 H) 10.43 (s, 1 H).

Example 134

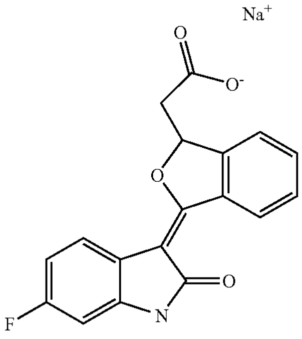

Sodium [(3E)-3-(6-fluoro-2-oxo-1,2-dihydro-3H-indol-3-ylidene)-1,3-dihydro-2-benzofuran-1-yl] acetate To a slurry of [3-(6-fluoro-2-oxo-1,2-dihydro-indol-3-ylidene)-1,3-dihydro-isobenzofuran-1-yl]-acetic acid (521 mg, 1.60 mmol) in MeOH (100.0 ml) at room temperature was added 0.5M NaOMe/MeOH (3.20 ml). The solution was rapidly stirred for 15 minutes and then rotary evaporated (combined 16 mg of product obtained from previously run reaction). The solid was chased with MeOH (20 ml) and then EtOAc (15 ml) to give sodium [(3E)-3-(6-fluoro-2-oxo-1,2-dihydro-3H-indol-3-ylidene)-1,3-dihydro-2-benzofuran-1-yl]acetate as a yellow solid (557 mg, 100%).

$^1$H NMR (300 MHz, DMSO-D6) δ ppm 2.52 (obsc m, 2 H) 6.23 (t, J=6.89 Hz, 1 H) 6.70 (m, 2 H) 7.54 (t, J=7.33 Hz, 1 H) 7.62 (t, J=7.04 Hz, 1 H) 7.74 (d, J=7.33 Hz, 1 H) 7.83 (dd, J=8.21, 5.86 Hz, 1 H) 9.57 (d, J=7.92 Hz, 1 H) 10.68 (s, 1 H).

The following Example 135 was prepared using the experiment procedure described in Example 136, but with the appropriate reagent, reaction conditions and reactant substitutions that will be readily realized by those of ordinary skill in this art without the exercise of undue experimentation.

Example 135

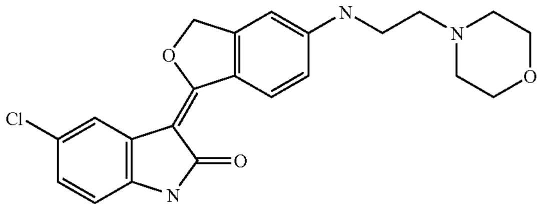

5-Chloro-3-[5-(2-morpholin-4-yl-ethylamino)-3H-isobenzofuran-1-ylidene]-1,3-dihydro-indol-2-one $^1$H NMR (500 MHz, DMSO-$d_6$) δ ppm 2.43 (br s, 4 H) 2.53 (t, J=6.59 Hz, 2 H) 3.28 (q, J=5.86 Hz, 2 H) 3.59 (t, J=4.39 Hz, 4 H) 5.67 (s, 2 H) 6.73 (s, 1 H) 6.76 (m, 2 H) 6.81 (t, J=5.37 Hz, 1 H) 7.03 (dd, J=8.05, 2.20 Hz, 1 H) 7.70 (d, J=2.44 Hz, 1 H) 9.33 (d, J=9.28 Hz, 1 H) 10.34 (s, 1 H).

Preparation 22

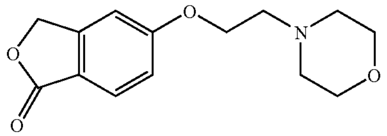

Preparation of 5-(2-Morpholin-4-yl-ethoxy)-3H-isobenzofuran-1-one

A mixture of 5-hydroxyphthalide (1.0 g, 6.66 mmol), 4-(2-chloroethyl)-morpholine hydrochloride (1.49 g, 8.01 mmol), potassium carbonate (2.3 g, 16.6 mmol) and sodium iodide (1.0 g, 6.67 mmol) in ethanol (40 ml) was stirred at reflux under nitrogen for 18 hours. The mixture was cooled to room temperature, and filtered through celite. The filtrate solution was evaporated to dryness. The residue was partitioned between EtOAc (75 ml) and 2M HCl solution (50 ml). The organic layer was extracted with 2M HCl (2×30 ml). The aqueous layers were combined, basified with NaOH aqueous solution, and extracted with $CHCl_3$ (3×50 ml). The organic layers were combined, dried over anhydrous $Na_2SO_4$, and evaporated to a light brown solid, which was triturated with $CHCl_3$/Hexanes to give 5-(2-morpholin-4-yl-ethoxy)-3H-isobenzofuran-1-one as white crystals (1.43 g, 82%).

$^1$H NMR (500 MHz, $CDCl_3$) δ ppm 2.74 (br s, 4 H) 2.98 (br s, 2 H) 3.83 (br s, 4 H) 4.31 (br s, 2 H) 5.25 (s, 2 H) 6.95 (s, 1 H) 7.05 (dd, J=8.54, 2.20 Hz, 1 H) 7.83 (d, J=8.30 Hz, 1 H).

Example 136

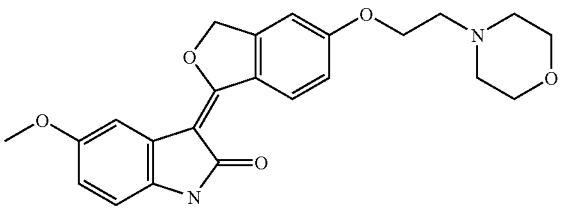

5-Methoxy-3-[5-(2-morpholin-4-yl-ethoxy)-3H-isobenzofuran-1-ylidene]-1,3-dihydro-indol-2-one To a stirred solution of 5-methoxyoxindole (197 mg, 1.21 mmol) in anhydrous THF (10 ml) under nitrogen was added 1.0M LiHMDS/THF solution (2.8 ml, 2.8 mmol). The mixture was stirred at room temperature for 10 minutes, and 5-(2-morpholin-4-yl-ethoxy)-3H-isobenzofuran-1-one (200 mg, 0.76 mmol) was added. After stirred at room temperature for 3.0 hours, the mixture was poured into a mixture of THF (5 ml) and 2M HCl aqueous solution (10 ml), and heated at 60° C. for 40 minutes. The mixture was cooled to room temperature, basified with 5M NaOH aqueous solution, and then poured into water (150 ml). The resulting solid was separated, rinsed with water, and dried to give 5-methoxy-3-[5-(2-morpholin-4-yl-ethoxy)-3H-isobenzofuran-1-ylidene]-1,3-dihydro-indol-2-one as a yellow solid (275 mg, 89%).

$^1$H NMR (500 MHz, DMSO-$d_6$) δ ppm 2.43 (br s, 4 H) 2.68 (t, J=5.61 Hz, 2 H) 3.53 (t, J=4.88 Hz, 4 H) 3.68 (s, 3 H) 4.16 (t, J=5.61 Hz, 2 H) 5.69 (s, 2 H) 6.63 (m, 2 H) 7.07 (dd, J=9.03, 2.20 Hz, 1 H) 7.17 (s, 1 H) 7.36 (d, J=2.44 Hz, 1 H) 9.52 (d, J=9.27 Hz, 1 H) 10.12 (s, 1 H).

The following Example 137 through 139 were prepared using the experiment procedure described in Example 136, but with the appropriate reagent, reaction conditions and reactant substitutions that will be readily realized by those of ordinary skill in this art without the exercise of undue experimentation Example 137

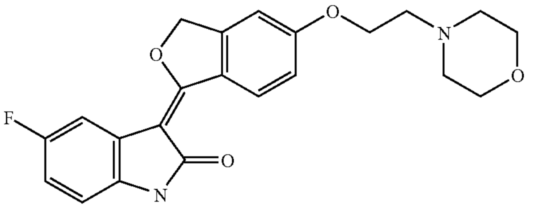

5-Fluoro-3-[5-(2-morpholin-4-yl-ethoxy)-3H-isobenzofuran-1-ylidene]-1,3-dihydro-indol-2-one

$^1$H NMR (500 MHz, DMSO-$d_6$) δ ppm 2.44 (br s, 4 H) 2.68 (t, J=5.61 Hz, 2 H) 3.53 (t, J=4.39 Hz, 4 H) 4.17 (t, J=5.61 Hz, 2 H) 5.72 (s, 2 H) 6.72 (dd, J=8.54, 4.64 Hz, 1 H) 6.84 (m, 1 H) 7.09 (dd, J=9.28, 2.44 Hz, 1 H) 7.20 (d, J=1.95 Hz, 1 H) 7.49 (dd, J=9.52, 2.68 Hz, 1 H) 9.50 (d, J=8.79 Hz, 1 H) 10.33 (s, 1 H).

Example 138

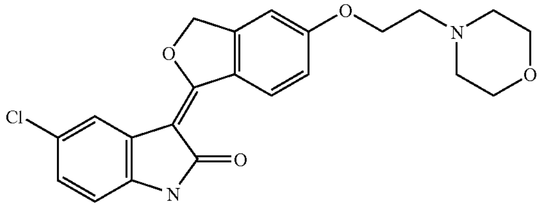

5-Chloro-3-[5-(2-morpholin-4-yl-ethoxy)-3H-isobenzofuran-1-ylidene]-1,3-dihydro-indol-2-one

$^1$H NMR (500 MHz, DMSO-$d_6$) δ ppm 2.44 (br s, 4 H) 2.68 (t, J=5.37 Hz, 2 H) 3.53 (t, J=4.39 Hz, 4 H) 4.17 (t, J=5.37 Hz, 2 H) 5.73 (s, 2 H) 6.75 (d, J=8.30 Hz, 1 H) 7.05 (dd, J=8.30, 1.95 Hz, 1 H) 7.10 (dd, J=8.79, 1.95 Hz, 1 H) 7.21 (s, 1 H) 7.71 (s, 1 H) 9.49 (d, J=8.79 Hz, 1 H) 10.45 (s, 1 H)

Preparation 23

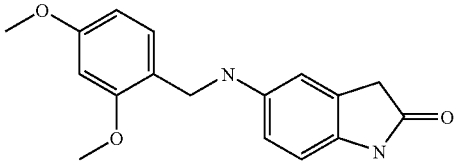

Preparation of 5-(2,4-Dimethoxy-benzylamino)-1,3-dihydro-indol-2-one

A mixture of 5-aminooxindole (1.0 g, 6.75 mmol), 3,5-dimethoxybenzaldehyde (1.35 g, 8.12 mmol), sodium triacetoxyborohydride (4.3 g, 20.3 mmol), and AcOH (0.5 ml) in DMF (15 ml) was stirred at room temperature for 3.5 hours. The mixture was partitioned between saturated $NaHCO_3$ solution (50 ml) and $CHCl_3$ (50 ml). The aqueous layer was extracted again with $CHCl_3$ (2×50 ml). The organic layers were combined, washed with saturated $NaHCO_3$ solution (50 ml), water (2×75 ml), dried over $Na_2SO_4$, and poured into $Et_2O$ (100 ml) with stirring. The resulting solid was filtered, washed with $Et_2O$ and dried to give 5-(2,4-dimethoxy-benzylamino)-1,3-dihydro-indol-2-one as a brown solid (1.02 g, 51%).

$^1$H NMR (500 MHz, DMSO-$d_6$) δ ppm 3.32 (s, 2 H) 3.72 (s, 3 H) 3.79 (s, 3 H) 4.06 (s, 2 H) 5.52 (br s, 1 H) 6.33 (dd, J=8.30, 1.95 Hz, 1 H) 6.44 (dd, J=8.30, 2.44 Hz, 1 H) 6.52 (m, 3 H) 7.12 (d, J=8.30 Hz, 1 H) 9.91 (s, 1 H).

Example 139

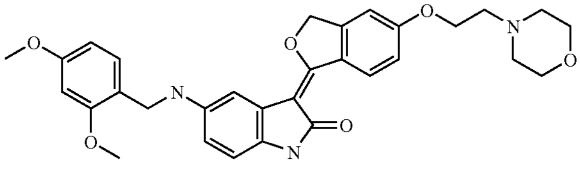

5-(2,4-Dimethoxy-benzylamino)-3-[5-(2-morpholin-4-yl-ethoxy)-3H-isobenzofuran-1-ylidene]-1,3-dihydro-indol-2-one $^1$H NMR (500 MHz, DMSO-$d_6$) δ ppm 2.48 (br s, 4 H) 2.73 (t, J=5.61 Hz, 2 H) 3.58 (t, J=4.39 Hz, 4 H) 3.72 (s, 3 H) 3.83 (s, 3 H) 4.11 (d, J=5.37 Hz, 2 H) 4.21 (t, J=5.86 Hz, 2 H) 5.47 (t, J=5.86 Hz, 1 H) 5.70 (s, 2 H) 6.28 (dd, J=8.30, 2.44 Hz, 1 H) 6.45 (dd, J=8.54, 2.20 Hz, 1 H) 6.51 (d, J=8.30 Hz, 1 H) 6.55 (d, J=2.44 Hz, 1 H) 7.10 (dd, J=8.79, 2.44 Hz, 1 H) 7.19 (dd, J=5.13, 3.17 Hz, 2 H) 7.24 (d, J=2.44 Hz, 1 H) 9.58.

The present invention is not to be limited in scope by the exemplified embodiments which are intended as illustrations of single aspects of the invention only. Indeed, various modifications of the invention in addition to those described herein will become apparent to those skilled in the art from the foregoing description. For example novel compounds of formula II, below may be utilized in the method of treating diseases described above.

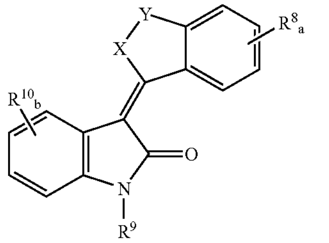

wherein X is O; Y is $[C(R^9)_2]_c$; $R^{10}$ is selected from the group consisting of halogen, nitro, hydroxy, hydrocarbyl, substituted hydrocarbyl, amide, thioamide, amine, thioether and sulfonyl; $R^8$ is selected from the group consisting of halogen, nitro, hydroxy, hydrocarbyl, substituted hydrocarbyl, amide, thioamide, amine, thioether and sulfonyl and phosphonic acid; $R^9$ is selected from the group consisting of hydrogen, hydrocarbyl and substituted hydrocarbyl; c is an integer of from 1 to 2; b is 0 or an integer from 1 to 3; a is 0 or an integer of from 1 to 3 and pharmaceutically acceptable salts thereof. Said hydrocarbyl and/or substituted hydrocarbyl may be alkyl, alkenyl, alkynyl, aryl (including carbocylic aryl and heterocyclic aryl) and alkaryl.

Such modifications are intended to fall within the scope of the appended claims.

All references cited herein are hereby incorporated by reference in their entirety.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

What is claimed:

1. A compound represented by the formula II

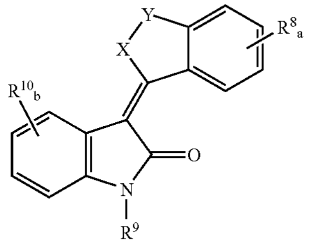

wherein X is O; Y is $[C(R^9)_2]_c$; $R^{10}$ is selected from the group consisting of halogen, nitro, hydroxy, hydrocarbyl, substituted hydrocarbyl, amide, thioamide, amine, thioether and sulfonyl; $R^8$ is amine, $R^9$ is selected from the group consisting of hydrogen, hydrocarbyl and substituted hydrocarbyl; c is an integer of from 1 to 2; b is 0 or an integer from 1 to 2; a is 0 or an integer of from 1 to 3 and pharmaceutically acceptable salts thereof.

2. The compound of claim 1 wherein said amine is a N(R")R'" group wherein R" and R'" are independently selected from the group consisting of a straight-chain, branched or cyclic saturated aliphatic hydrocarbon having from 1 to 12 carbons which may be optionally substituted with one or more substituents which substituents are selected from the group consisting of hydroxyl, cyano, alkoxy, =O, =S, $NO_2$, halogen, dimethyl amino and SH; aryl which may be optionally substituted with one or more substituents selected from the group consisting of halogen, trihalomethyl, hydroxyl, SH, OH, $NO_2$, amine, thioether, cyano, alkoxy, alkyl and amino and alkaryl.

3. The compound of claim 2 wherein R" and R'" are independently selected from the group consisting of alkyl having from 1 to 12 carbons.

* * * * *

UNITED STATES PATENT AND TRADEMARK OFFICE

CERTIFICATE OF CORRECTION

PATENT NO. : 7,060,844 B2
APPLICATION NO. : 10/405577
DATED : June 13, 2006
INVENTOR(S) : Andrews et al.

It is certified that error appears in the above-identified patent and that said Letters Patent is hereby corrected as shown below:

Col. Heading 25-38 should be corrected to read col. 23-38 as shown on the attached sheets Signed and Sealed this Nineteenth Day of September, 2006

JON W. DUDAS

*Director of the United States Patent and Trademark Office*

TABLE 4
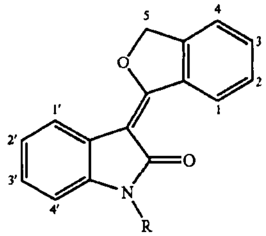
| Example Number | 1 | 2 | 3 | 4 | 5 | 1' | 2' | 3' | 4' | R |
|---|---|---|---|---|---|---|---|---|---|---|
| 43 | H | H | $NH_2$ | H | H, H | H | H | F | H | H |
| 44 | H | H | $NH_2$ | H | H, H | H | F | H | H | H |
| 45 | H | H | $NH(CH_2)_2Cl$ | H | H, H | H | H | H | H | H |
| 46 | H | H | $NH(CH_2)_2Cl$ | H | H, H | H | H | F | H | H |
| 47 | H | H | $NH(CH_2)_2Cl$ | H | H, H | H | F | H | H | H |
| 48 | H | H | 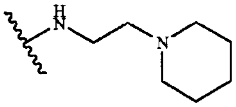 | H | H, H | H | H | H | H | H |
| 49 | H | H | 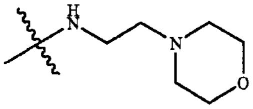 | H | H, H | H | H | H | H | H |
| 50 | H | H | 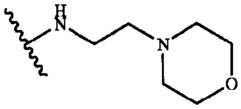 | H | H, H | H | H | F | H | H |
| 51 | H | H | 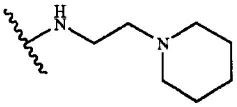 | H | H, H | H | H | F | H | H |
| 52 | H | H | 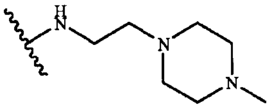 | H | H, H | H | H | H | H | H |
| 53 | H | H | 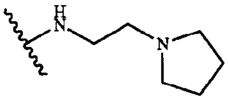 | H | H, H | H | H | H | H | H |
| 54 | H | H | 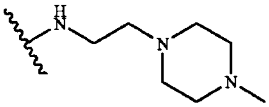 | H | H, H | H | H | F | H | H |
| 55 | H | H | 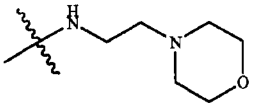 | H | H, H | H | F | H | H | H |

TABLE 4-continued
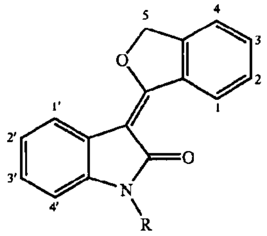
| Example Number | 1 | 2 | 3 | 4 | 5 | 1' | 2' | 3' | 4' | R |
|---|---|---|---|---|---|---|---|---|---|---|
| 56 | H | H | 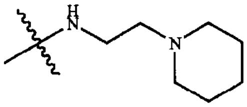 | H | H, H | H | F | H | H | H |
| 57 | H | H | 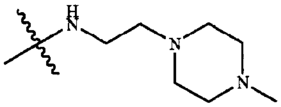 | H | H, H | H | F | H | H | H |
| 58 | H | H | 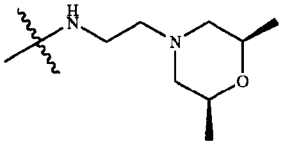 | H | H, H | H | H | H | H | H |
| 59 | H | H | 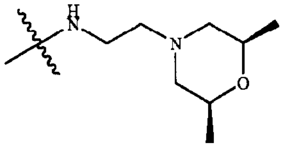 | H | H, H | H | F | H | H | H |
| 60 | H | H | 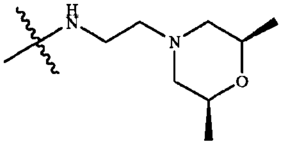 | H | H, H | H | H | F | H | H |
| 61 | H | H | 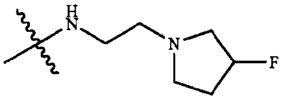 | H | H, H | H | H | H | H | H |
| 62 | H | H | 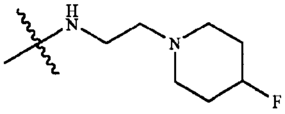 | H | H, H | H | H | H | H | H |
| 63 | H | H | 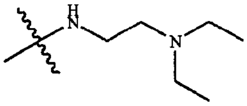 | H | H, H | H | F | H | H | H |

TABLE 4-continued
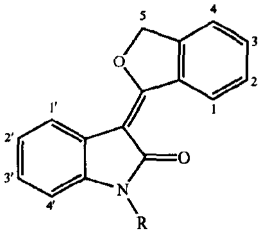
| Example Number | 1 | 2 | 3 | 4 | 5 | 1' | 2' | 3' | 4' | R |
|---|---|---|---|---|---|---|---|---|---|---|
| 64 | H | H | 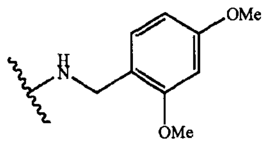 | H | H, H | H | H | H | H | H |
| 65 | H | H | 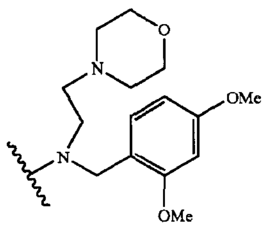 | H | H, H | H | H | H | H | H |
| 66 | H | H | 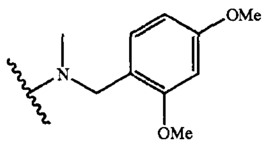 | H | H, H | H | H | F | H | H |
| 67 | H | H | 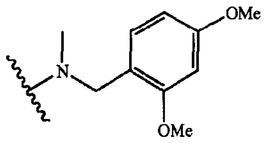 | H | H, H | H | H | H | H | H |
| 68 | H | H | 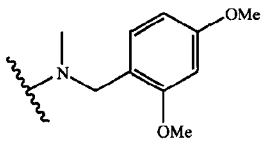 | H | H, H | H | Cl | H | H | H |
| 69 | H | H | 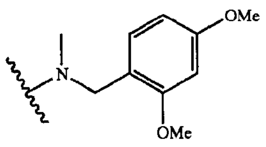 | H | H, H | H | H | H | F | H |
| 70 | H | H | 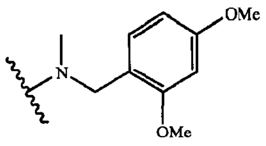 | H | H, H | H | F | H | H | H |

TABLE 4-continued
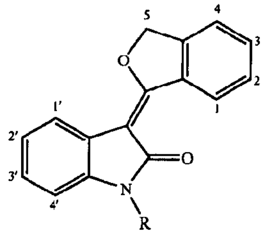
| Example Number | 1 | 2 | 3 | 4 | 5 | 1' | 2' | 3' | 4' | R |
|---|---|---|---|---|---|---|---|---|---|---|
| 71 | H | H | 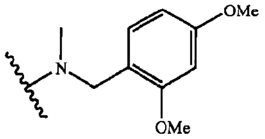 | H | H, H | H | H | Cl | H | H |
| 72 | H | H | $NHCH_3$ | H | H, H | H | H | F | H | H |
| 73 | H | H | $NHCH_3$ | H | H, H | H | F | H | H | H |
| 74 | H | H | $NHCH_3$ | H | H, H | H | Cl | H | H | H |
| 75 | H | H | $NHCH_3$ | H | H, H | H | H | Cl | H | H |
| 76 | H | H | $NHCH_3$ | H | H, H | H | H | H | F | H |
| 77 | H | H | $N(CH_3)_2$ | H | H, H | H | Cl | H | H | H |
| 78 | H | H | $NHC(C_6H_5)_3$ | H | H, H | H | Cl | H | H | H |
| 79 | H | H | $N(CH_2C_6H_5)_2$ | H | H, H | H | Cl | H | H | H |
| 80 | H | H | 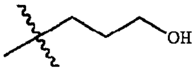 | H | H, H | H | H | H | H | H |
| 81 | H | H | 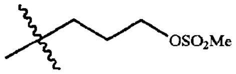 | H | H, H | H | H | H | H | H |
| 82 | H | H | 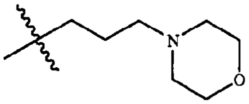 | H | H, H | H | H | H | H | H |
| 83 | H | H | 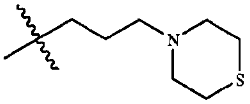 | H | H, H | H | H | H | H | H |
| 84 | H | H | 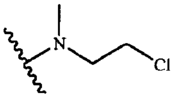 | H | H, H | H | H | H | H | H |
| 85 | H | H | 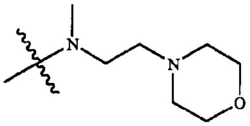 | H | H, H | H | H | H | H | H |
| 86 | H | H | 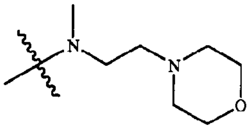 | H | H, H | H | F | H | H | H |

TABLE 4-continued
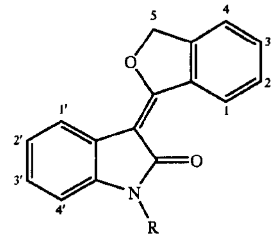
| Example Number | 1 | 2 | 3 | 4 | 5 | 1' | 2' | 3' | 4' | R |
|---|---|---|---|---|---|---|---|---|---|---|
| 87 | H | H | 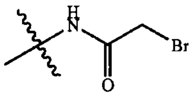 | H | H, H | H | Cl | H | H | H |
| 88 | H | H | 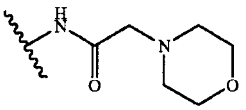 | H | H, H | H | Cl | H | H | H |
| 89 | H | H | 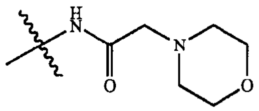 | H | H, H | H | H | H | H | H |
| 90 | H | H | 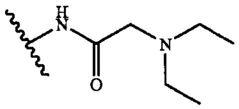 | H | H, H | H | Cl | H | H | H |
| 91 | H | H | 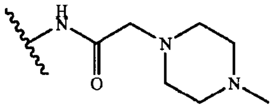 | H | H, H | H | Cl | H | H | H |
| 92 | H | H | 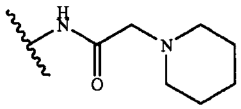 | H | H, H | H | Cl | H | H | H |
| 93 | H | H | $NH(CH_2)_2OH$ | H | H, H | H | H | H | H | H |
| 94 | H | H | $NH(CH_2)_2OH$ | H | H, H | H | H | F | H | H |
| 95 | H | H | $NH(CH_2)_2OCOCH_3$ | H | H, H | H | H | H | H | H |
| 96 | H | H | $NH(CH_2)_2OCOCH_3$ | H | H, H | H | H | F | H | H |
| 97 | H | H | 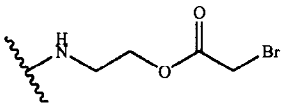 | H | H, H | H | H | H | H | H |

TABLE 4-continued
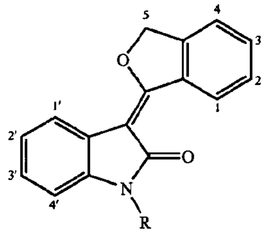
| Example Number | 1 | 2 | 3 | 4 | 5 | 1' | 2' | 3' | 4' | R |
|---|---|---|---|---|---|---|---|---|---|---|
| 98 | H | H | 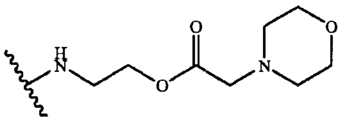 | H | H, H | H | H | H | H | H |
| 99 | H | H | 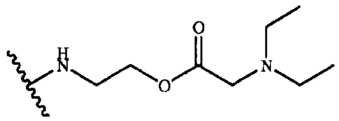 | H | H, H | H | H | H | H | H |
| 100 | H | H | 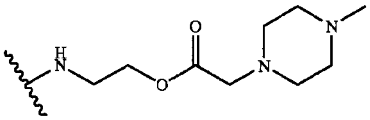 | H | H, H | H | H | H | H | H |
| 101 | H | H | 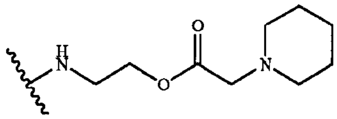 | H | H, H | H | H | H | H | H |
| 102 | H | H | Br | H | H, H | H | H | H | H | H |
| 103 | H | H | 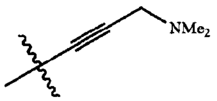 | H | H, H | H | H | H | H | H |
| 104 | H | H | 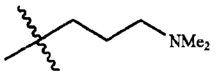 | H | H, H | H | H | H | H | H |
| 135 | H | H | 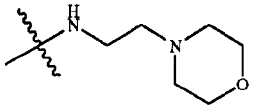 | H | H, H | H | Cl | H | H | H |

TABLE 5
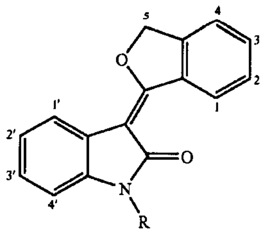
| Example Number | 1 | 2 | 3 | 4 | 5 | 1' | 2' | 3' | 4' | R |
|---|---|---|---|---|---|---|---|---|---|---|
| 105 | H | H | H | H | $—(CH_2)_2NH(CH_2)_2—$ | H | H | H | H | H |
| 106 | H | H | H | H | $—CH_2COOH$ | H | H | H | H | H |
| 107 | H | H | H | H | $—CH_2COOH$ | H | Cl | H | H | H |
| 108 | H | H | H | H | $—CH_2COOH$ | H | H | F | H | H |
| 109 | H | H | H | H | $—CH_2CH_2OH$ | H | H | H | H | H |
| 110 | H | H | H | H | $—(CH_2)_2OSO_2CH_3$ | H | H | H | H | H |
| 111 | H | H | H | H | 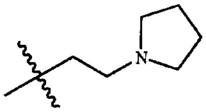 | H | H | H | H | H |
| 112 | H | H | H | H | 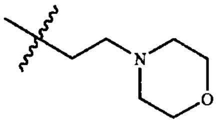 | H | H | H | H | H |
| 113 | H | H | H | H | 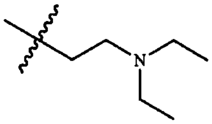 | H | H | H | H | H |
| 114 | H | H | H | H | 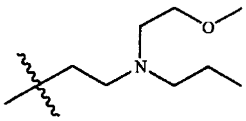 | H | H | H | H | H |
| 115 | H | H | H | H | 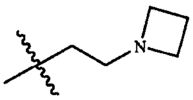 | H | H | H | H | H |
| 116 | H | H | H | H | $—CH_2N(CH_3)_2$ | H | H | H | H | H |
| 117 | H | H | H | H | $—CH_2NCO$ | H | H | H | H | H |
| 118 | H | H | H | H | $—CH_2NHCONH_2$ | H | H | H | H | H |
| 119 | H | H | H | H | $—CH_2NHCO_2C_2H_5$ | H | H | H | H | H |
| 120 | H | H | H | H | 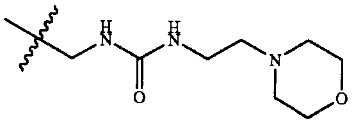 | H | H | H | H | H |
| 121 | H | H | H | H | 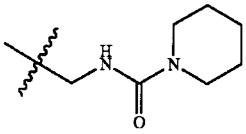 | H | H | H | H | H |

TABLE 5-continued
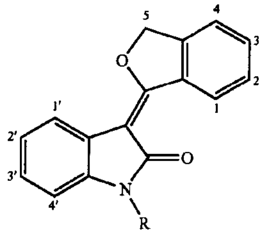
| Example Number | 1 | 2 | 3 | 4 | 5 | 1' | 2' | 3' | 4' | R |
|---|---|---|---|---|---|---|---|---|---|---|
| 122 | H | H | H | H | 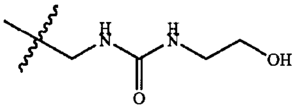 | H | H | H | H | H |
| 123 | H | H | H | H | 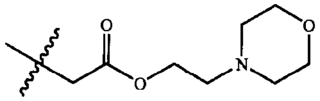 | H | H | H | H | H |
| 124 | H | H | H | H | 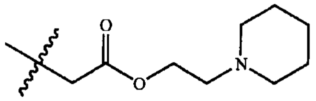 | H | H | F | H | H |
| 125 | H | H | H | H | $—CH_2CO_2CH_3$ | H | H | F | H | H |
| 126 | H | H | H | H | —COOH | H | H | H | H | H |
| 127 | H | H | H | H | 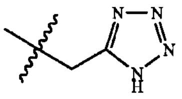 | H | H | H | H | H |
| 128 | H | H | H | H | $—CH_2CONH_2$ | H | H | H | H | H |
| 129 | H | H | H | H | Me | H | H | H | H | H |
| 130 | H | H | H | H | 2xMe | H | H | H | H | H |
| 131 | H | H | OMe | H | $—CH_2COOH$ | H | H | H | H | H |
| 132 | H | OMe | H | H | $—CH_2COOH$ | H | H | H | H | H |
| 133 | H | H | H | H | $—CH_2COONa$ | H | H | H | H | H |
| 134 | H | H | H | H | $—CH_2COONa$ | H | H | F | H | H |
TABLE 6
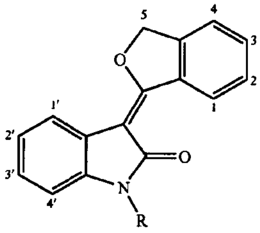
| Example Number | 1 | 2 | 3 | 4 | 5 | 1' | 2' | 3'4' | R | |
|---|---|---|---|---|---|---|---|---|---|---|
| 136 | H | H | 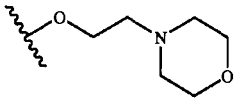 | H | H, H | H | OMe | F | H | H |